(12) United States Patent
Ozawa

(10) Patent No.: US 7,050,086 B2
(45) Date of Patent: May 23, 2006

(54) ELECTRONIC ENDOSCOPE SYSTEM WITH COLOR-BALANCE ALTERATION PROCESS

(75) Inventor: Ryo Ozawa, Saitama (JP)

(73) Assignee: PENTAX Corporation, Tokyo (JP)

( * ) Notice: Subject to any disclaimer, the term of this patent is extended or adjusted under 35 U.S.C. 154(b) by 651 days.

(21) Appl. No.: 10/178,534

(22) Filed: Jun. 25, 2002

(65) Prior Publication Data

US 2002/0196335 A1    Dec. 26, 2002

(30) Foreign Application Priority Data

| Jun. 26, 2001 | (JP) | ............... P2001-193134 |
| Jun. 29, 2001 | (JP) | ............... P2001-198274 |
| Jun. 29, 2001 | (JP) | ............... P2001-198584 |
| Oct. 31, 2001 | (JP) | ............... P2001-333880 |

(51) Int. Cl.
*H04N 9/47* (2006.01)
*H04N 13/00* (2006.01)
*H04N 7/18* (2006.01)

(52) U.S. Cl. ............... 348/70; 348/45; 348/65

(58) Field of Classification Search ............... 348/70, 348/650, 635; 382/274, 275; 600/101, 109, 600/112

See application file for complete search history.

(56) References Cited

U.S. PATENT DOCUMENTS

| 4,876,610 | A | * | 10/1989 | Ohsawa et al. ............ 358/443 |
| 4,941,190 | A | * | 7/1990 | Joyce ..................... 382/264 |
| 5,032,913 | A | * | 7/1991 | Hattori et al. ............. 348/70 |
| 5,068,746 | A | * | 11/1991 | Ohsawa et al. ............ 358/443 |
| 5,220,620 | A | * | 6/1993 | Nakano et al. ............ 382/167 |
| 5,243,967 | A | * | 9/1993 | Hibino .................... 600/109 |
| 5,473,439 | A | * | 12/1995 | Pappas .................... 358/3.27 |
| 5,555,324 | A | * | 9/1996 | Waxman et al. ........... 382/254 |
| 5,864,361 | A | | 1/1999 | Sekiya et al. |
| 5,929,899 | A | | 7/1999 | Takahashi et al. |
| 6,371,908 | B1 | | 4/2002 | Furusawa et al. |
| 6,879,339 | B1 | * | 4/2005 | Ozawa ..................... 348/71 |
| 6,882,754 | B1 | * | 4/2005 | Hayashi ................... 382/275 |
| 2004/0064016 | A1 | * | 4/2004 | Kobayashi et al. ......... 600/109 |

FOREIGN PATENT DOCUMENTS

JP          200125025          1/2001

OTHER PUBLICATIONS

English Language Translation for JP Appln. No. 2001-25025.

* cited by examiner

*Primary Examiner*—Vu Le
*Assistant Examiner*—Dave Czekaj
(74) *Attorney, Agent, or Firm*—Greenblum & Bernstein, P.L.C.

(57) ABSTRACT

In an electronic endoscope system including a video scope having a solid-state image sensor that successively produces a frame of red, green, and blue image-pixel signals, a difference value is calculated between a value of each of corresponding central red, green, and blue image-pixel signals and an average of values of circumferential image-pixel signals surrounding the central image-pixel signal. When the respective values of the central red and green image-pixel signals are smaller than the corresponding averages of values, they are decreased in proportion to the absolute values of the corresponding difference values. When the value of the central blue image-pixel signal is smaller than the corresponding average of values, it is increased in proportion to the absolute value of the corresponding difference value.

22 Claims, 28 Drawing Sheets

FIG. 2

| | Fst. LINE | Snd. LINE | Thd. LINE | | | | | | mth-LINE |
|---|---|---|---|---|---|---|---|---|---|
| | R1n | R2n | R3n | ............................ | | | | | Rmn |
| | ⋮ | ⋮ | ⋮ | | | | | | ⋮ |
| | R17 | R27 | R37 | R47 | R57 | R67 | R77 | | |
| | R16 | R26 | R36 | R46 | R56 | R66 | R76 | | |
| | R15 | R25 | R35 | R45 | R55 | R65 | R75 | | |
| | R14 | R24 | R34 | R44 | R54 | R64 | R74 | | |
| | R13 | R23 | R33 | R43 | R53 | R63 | R73 | ...... | Rm3 |
| | R12 | R22 | R32 | R42 | R52 | R62 | R72 | ...... | Rm2 |
| | R11 | R21 | R31 | R41 | R51 | R61 | R71 | ...... | Rm1 |

PIXEL-READING DIRECTION ↑

LINE-READING DIRECTION →

FIG. 5

| $R_{(i-3)(j-3)}$ | $R_{(i-3)(j-2)}$ | $R_{(i-3)(j-1)}$ | $R_{(i-3)j}$ | $R_{(i-3)(j+1)}$ | $R_{(i-3)(j+2)}$ | $R_{(i-3)(j+3)}$ |
|---|---|---|---|---|---|---|
| $R_{(i-2)(j-3)}$ | $R_{(i-2)(j-2)}$ | $R_{(i-2)(j-1)}$ | $R_{(i-2)j}$ | $R_{(i-2)(j+1)}$ | $R_{(i-2)(j+2)}$ | $R_{(i-2)(j+3)}$ |
| $R_{(i-1)(j-3)}$ | $R_{(i-1)(j-2)}$ | $R_{(i-1)(j-1)}$ | $R_{(i-1)j}$ | $R_{(i-1)(j+1)}$ | $R_{(i-1)(j+2)}$ | $R_{(i-1)(j+3)}$ |
| $R_{i(j-3)}$ | $R_{i(j-2)}$ | $R_{i(j-1)}$ | $R_{ij}$ | $R_{i(j+1)}$ | $R_{i(j+2)}$ | $R_{i(j+3)}$ |
| $R_{(i+1)(j-3)}$ | $R_{(i+1)(j-2)}$ | $R_{(i+1)(j-1)}$ | $R_{(i+1)j}$ | $R_{(i+1)(j+1)}$ | $R_{(i+1)(j+2)}$ | $R_{(i+1)(j+3)}$ |
| $R_{(i+2)(j-3)}$ | $R_{(i+2)(j-2)}$ | $R_{(i+2)(j-1)}$ | $R_{(i+2)j}$ | $R_{(i+2)(j+1)}$ | $R_{(i+2)(j+2)}$ | $R_{(i+2)(j+3)}$ |
| $R_{(i+3)(j-3)}$ | $R_{(i+3)(j-2)}$ | $R_{(i+3)(j-1)}$ | $R_{(i+3)j}$ | $R_{(i+3)(j+1)}$ | $R_{(i+3)(j+2)}$ | $R_{(i+3)(j+3)}$ |

FIG. 7

FACTOR-SETTING TABLE

| | DISTANCE | 1st. MODE | 2nd. MODE | 3rd. MODE | 4th. MODE | 5th. MODE | 6th. MODE | 7th. MODE | 8th. MODE |
|---|---|---|---|---|---|---|---|---|---|
| f01 | 0 | 1 | 1 | 1 | 1 | 1 | 1 | 1 | 1 |
| f02 | 1*d | -1/4 | 0 | 0 | 0 | 0 | 0 | 0 | 0 |
| f03 | 1.41*d | 0 | -1/4 | 0 | 0 | 0 | 0 | 0 | 0 |
| f04 | 2*d | 0 | 0 | -1/8 | -1/12 | 0 | 0 | 0 | 0 |
| f05 | 2.24*d | 0 | 0 | 0 | -1/12 | -1/12 | 0 | 0 | 0 |
| f06 | 2.83*d | 0 | 0 | 0 | 0 | -1/12 | -1/8 | 0 | 0 |
| f07 | 3*d | 0 | 0 | 0 | 0 | 0 | -1/8 | 0 | 0 |
| f08 | 3.16*d | 0 | 0 | 0 | 0 | 0 | 0 | -1/16 | 0 |
| f09 | 3.61*d | 0 | 0 | 0 | 0 | 0 | 0 | -1/16 | 0 |
| f10 | 4.24*d | 0 | 0 | 0 | 0 | 0 | 0 | 0 | -1/4 |

FIG. 8

FACTOR-SETTING-MODE SELECTION TABLE

| MAGNIFYING-POWER | 1 | 2 | 3 | 4 |
|---|---|---|---|---|
| VIDEO SCOPE 10' (M×N) | 1st. MODE | 3rd. MODE | 5th. MODE | 7th. MODE |
| VIDEO SCOPE 10 (m×n) | 2nd. MODE | 4th. MODE | 6th. MODE | 8th. MODE |

FIG. 27

FACTOR-SETTING-MODE SELECTION TABLE

| MAGNIFYING-POWER | 1>mp>1.5 | 1.5>mp>2.5 | 2.5>mp>3.5 | 3.5>mp>4 |
|---|---|---|---|---|
| VIDEO SCOPE 10' (M×N) | 1st. MODE | 3rd. MODE | 5th. MODE | 7th. MODE |
| VIDEO SCOPE 10 (m×n) | 2nd. MODE | 4th. MODE | 6th. MODE | 8th. MODE |

FIG. 30

FACTOR-SETTING-MODE SELECTION TABLE

| OPENING VALUE | $OV_{MIN} \leq ov < OV_1$ | $OV_1 \leq ov < OV_2$ | $OV_2 \leq ov < OV_2$ | $OV_2 \leq ov$ |
|---|---|---|---|---|
| VIDEO SCOPE 10' (M×N) | 1st. MODE | 3rd. MODE | 5th. MODE | 7th. MODE |
| VIDEO SCOPE 10 (m×n) | 2nd. MODE | 4th. MODE | 6th. MODE | 8th. MODE |

ELECTRONIC ENDOSCOPE SYSTEM WITH COLOR-BALANCE ALTERATION PROCESS

BACKGROUND OF THE INVENTION

1. Field of the Invention

The present invention relates to an electronic endoscope system in which an endoscope image is reproduced as a full color image on a TV monitor, and, in particular, to such an electronic endoscope system with a color-balance alteration process, which is constituted such that, for example, the endoscope image can be reproduced on the TV monitor as if it were sprayed with a dye-solution.

2. Description of the Related Art

As is well known, an electronic endoscope system includes a video scope that is inserted in an organ of a human body, and the video scope has a solid-state image sensor for capturing an organ image or endoscope image as a frame of image-pixel-signals. Also, the electronic endoscope system also includes an image-signal processing unit for producing a video signal based on the frames of image-pixel-signals successively read from the solid-state image sensor, and a TV monitor for reproducing the endoscope image as a motion picture based on the video signal fed from the image-signal processing unit.

Recently, it is usual to manufacture an electronic endoscope system such that the endoscope image is reproduced as a full color motion image on a TV monitor. Thus, a dye-spraying examination method was developed and has been used as a medical examination method in the medical field in which electronic endoscope systems are used. For example, when a subtle uneven surface of the mucous membrane of a stomach or a colon is examined, the dye-spraying medical method is utilized.

In particular, the mucous membrane surface of the stomach or the colon features a reddish orange tone as a whole, and thus it is very difficult to examine the subtle unevenness of the mucous membrane surface. In order that the subtle unevenness of the mucous membrane surface can be clearly and easily examined on a TV monitor, a bluish solution, such as an Indigo Carmine solution, is introduced into a forceps-insertion passage of the video scope, and is sprayed over the mucous membrane surface. The solution has a tendency toward gathering in fine recess areas on the mucous membrane surface, and it flows away from fine land areas on the mucous membrane surface. Namely, the fine recess areas on the mucous membrane surface are colored blue and clearly contrast with the reddish orange areas. Thus, it is possible to easily carry out an examination of the subtle unevenness of the mucous membrane surface.

However, there are various drawbacks in the dye-spraying medical examination method. For example, a dye must be harmless to a human body, and it is troublesome to develop harmless dyes. Also, the use of a dye-spraying medical examination method prolongs the medical examination time when using the electronic endoscope system, resulting in an increase in the patient's pain and discomfort. Further, once a dye-solution is sprayed, it is impossible to immediately reproduce an endoscope image without the sprayed dye-solution.

In order to resolve the above-mentioned problems, Japanese Laid-Open Patent Publication (KOKAI) No. 2001-25025 discloses an electronic endoscope system with a simulated dye-spraying process or color-balance alteration process for electronically processing an endoscope image as if it were sprayed with a blue-solution.

In particular, a full color endoscope image is formed based on a frame of three-primary color image-pixel-signals which is composed of a frame of red image-pixel-signals, a frame of green image-pixel-signals, and a frame of blue image-pixel-signals. In the color-balance alteration process, for example, a value of a central red image-pixel-signal is compared with an average of values of eight surrounding circumferential red image-pixel-signals.

If the value of the central red image-pixel-signal is lower than the average of the values of the circumferential red image-pixel-signals, the central red image-pixel-signal derives from a fine recess area on a mucous membrane surface of, for example, a stomach. However, if the value of the central red image-pixel-signal is higher than the average of the values of the circumferential red image-pixel-signals, the central red image-pixel-signal derives from a fine land area on the mucous membrane surface of the stomach. The same is true for the green image-pixel-signals and the blue image-pixel-signals.

Accordingly, for example, if the frame of three-primary color image-pixel-signals is processed such that the values of red and green image-pixel-signals, deriving from the fine recess areas, are lowered, an endoscope image can be reproduced as if it were sprayed with a bluish-solution.

Nevertheless, in the electronic endoscope system, as shown in the aforesaid KOKAI No. 2001-25025, there are drawbacks to be settled, as discussed hereinafter.

SUMMARY OF THE INVENTION

Therefore, an object of the present invention is to provide an electronic endoscope system with a color-balance alteration process, in which the conventional drawbacks can be overcome.

In accordance with a first aspect to the invention, there is provided an electronic endoscope system including a video scope having a solid-state image sensor that successively produces a frame of color image-pixel signals composed of two frames of first-type-single-color image-pixel signals and second-type-single-color image-pixel signals. In this electronic endoscope system, a calculation system calculates a first difference value between a first value of a central first-type-single-color image-pixel signal and a first average of values of circumferential first-type-single-color image-pixel signals surrounding the central first-type-single-color image-pixel signal, and a second difference value between a second value of a corresponding central second-type-single-color image-pixel signal and a second average of values of circumferential second-type-single-color image-pixel signals surrounding the central second-type-single-color image-pixel signal. A color-balance alteration system alters the first value when being smaller than the first average of values, and the second value when being smaller than the second average of values, such that one of the first and second values is increased in proportion to an absolute value of a corresponding one of the first and second difference values, and that the remaining one of the first and second values is decreased in proportion to an absolute value of the remaining corresponding one of the first and second difference values.

The electronic endoscope system may comprise a first video signal production system that produces a first type of video signal based on the frame of color image-pixel signals, a second video signal production system that produces a second type of video signal based the frame of color image-pixel signals processed by the color-balance alteration system, a monitor system that is capable of selectively displaying a first image and a second image based on the first and second types of video signals, respectively.

The electronic endoscope system may further comprise a display-mode selection system that selects either a first display mode or a second display mode, and a display control system that displays the first image on the monitor system based on the first type of video signal when the first display mode is selected by the display-mode selection system, and that displays the second image on the monitor system based on the second type of video signal when the second display mode is selected by the display-mode selection system. In this case, the electronic endoscope system preferably comprises a disablement system that disables the color-balance alteration system when the first display mode is selected by the display-mode selection system, and an enablement system that enables the color-balance alteration system when the second display mode is selected by the display-mode selection system.

According toe the first aspect of the invention, the frame of color image-pixel signals may be composed of a frame of third-type-single-color image-pixel signals. The calculation system further calculates a third difference value between a third value of a corresponding central third-type-single-color image-pixel signal and a third average of values of circumferential third-type-single-color image-pixel signals surrounding the central third-type-single-color image-pixel signal, and a color-balance alteration system alters the first value when being smaller than the first average of values, the second value when being smaller than the second average of values, and the third value when being smaller than the third average of values, such that two of the first, second, and third values are respectively increased in proportion to absolute values of corresponding ones of the first, second, and third difference values, and that the remaining one of the first, second, and third values is decreased in proportion to absolute values of the remaining corresponding one of the first, second, and third difference values.

In accordance with a second aspect of the invention, there is provided an electronic endoscope system including a video scope having a solid-state image sensor that successively produces a frame of color image-pixel signals. In this electronic endoscope system, a first video signal production system produces a first type of video signal based on the frame of color image-pixel signals. A calculation system calculates a difference value between a value of a central color image-pixel signal and an average of values of circumferential color image pixels surrounding the central color image-pixel signal. A color-balance alteration system alters the value of the central color image-pixel signal in accordance with the difference value calculated by the calculation system. A second video signal production system produces a second type of video signal based the frame of color image-pixel signals processed by the color-balance alteration system. A monitor system is capable of simultaneously displaying a first image and a second image based on the first and second types of video signals, respectively.

According to the second aspect of the invention, the electronic endoscope system may comprise a first storage system that stores the frame of color image-pixel signals, on which the production of the first type of video signal is based, and a second storage system that stores the frame of color image-pixel signals, processed by the color-balance alteration system, on which the production of the second type of video signal is based. The electronic endoscope system may further comprise a display-mode selection system that selects either a first display mode or a second display mode, and a display control system that displays the first image on the monitor system based on the first type of video signal when the first display mode is selected by the display-mode selection system, and that simultaneously displays the first and second images on the monitor system based on the first and second types of video signals when the second display mode is selected by the display-mode selection system.

According to a third aspect of the invention, an electronic endoscope system comprises a video scope having a solid-state image sensor that successively produces a first type frame of color image-pixel signals, an image-signal processing unit including a first video signal production system that produces a first type of video signal based on the first type frame of color image-pixel signals, and a first monitor system that displays a first image based on the first type of video signal. The electronic endoscope system also comprises a color-balance alteration process unit, which includes: a color image-pixel-signal production system that successively produces a second type frame of color image-pixel signals based on the first type of video signal; a calculation system that calculates a difference value between a value of a central color image-pixel signal, included in the second type frame, and an average of values of circumferential color image pixels surrounding the central color image-pixel signal; a color-balance alteration system that alters the value of the central color image-pixel signal in accordance with the difference value calculated by the calculation system, whereby the second type of color image-pixel signals is subjected to a color-balance alteration process by the color-balance alteration system; and a second video signal production system that produces a second type of video signal based on the second type frame of color image-pixel signals subjected to the color-balance alteration process. The electronic endoscope system further comprises a second monitor system that display a second image based on the second type of video signals.

According to the third aspect of the invention, the color-balance alteration process unit may further include a third video signal production system that produces a third type of video signal based on the second type frame of color image-pixel signals not subjected to the color-balance alteration process, and the second monitor system is capable selectively displaying a third image based on the third type of video signals.

According to the third aspect of the invention, the color-balance alteration unit may further includes a display-mode selection system that selects either a first display mode or a second display mode, and a display control system that displays the second image on the second monitor system based on the second type of video signal when the first display mode is selected by the display-mode selection system, and that displays the third image on the second monitor system based on the third type of video signal when the second display mode is selected by the display-mode selection system. Preferably, the color-balance alteration unit may further include a disablement system that disables the color-balance alteration system when the first display mode is selected by the display-mode selection system, and an enablement system that enables the color-balance alteration system when the second display mode is selected by the display-mode selection system.

According to the third aspect of the invention, the color-balance alteration unit may further include a clock-pulse generator that produces a series of clock pulses. In this case, the successive production of the second type frame of color image-pixel signals by the color image-pixel-signal production system, the calculation of the difference value by the calculation system, and the alteration of the central color image-pixel signal by the color-balance alteration system being performed based on the clock pulses. A clock-pulse-frequency change system changes a frequency of the clock pulses in accordance with a variation in a spatial frequency of the first image.

According to the third aspect of the invention, the color-balance alteration unit may further include a restriction system that restricts an area, to be subjected to the color-balance alteration process, on a display area of the second monitor system, such that character information, displayed on the display area of the second monitor system, is prevented from being subjected to the color-balance alteration process. Preferably, the color-balance alteration unit further includes a restriction-area change system that changes the area restricted by the restriction system.

In accordance with a fourth aspect of the invention, there is provided an electronic endoscope system including a video scope having a solid-state image sensor that successively produces a frame of color image-pixel signals composed of two frames of first-type-single-color image-pixel signals and second-type-single-color image-pixel signals. A calculation system calculates a difference value between a first value of a central first-type-single-color image-pixel signal and an average of values of circumferential first-type-single-color image-pixel signals surrounding the central first-type-single-color image-pixel signal, and a difference value between a value of a corresponding central second-type-single-color image-pixel signal and an average of values of circumferential second-type-single-color image-pixel signals surrounding the central second-type-single-color image-pixel signal. A comparison system compares the value of the central first-type-single-color image-pixel signal and the value of the central second-type-single-color image-pixel signals with each other, to thereby determine which values is smaller. A color-balance alteration system decreases only a smaller one of the two values in proportion to an absolute value of the corresponding difference value when it is smaller than the corresponding average of values.

According to the fourth aspect of the invention, the electronic endoscope system may further comprises a first video signal production system that produces a first type of video signal based on the frame of color image-pixel signals, a second video signal production system that produces a second type of video signal based the frame of color image-pixel signals processed by the color-balance alteration system, and a monitor system that is capable of selectively displaying a first image and a second image based on the first and second types of video signals, respectively.

According to the fourth aspect of the invention, the electronic endoscope system may further comprises a display-mode selection system that selects either a first display mode or a second display mode, and a display control system that displays the first image on the monitor system based on the first type of video signal when the first display mode is selected by the display-mode selection system, and that displays the second image on the monitor system based on the second type of video signal when the second display mode is selected by the display-mode selection system. Preferably, the electronic endoscope system further comprises a disablement system that disables the color-balance alteration system when the first display mode is selected by the display-mode selection system, and an enablement system that enables the color-balance alteration system when the second display mode is selected by the display-mode selection system.

According to the fourth aspect of the invention, the frame of color image-pixel signals is further composed of a frame of third-type-single-color image-pixel signals. In this case, the calculation system calculates a difference value between a value of a corresponding central third type-single-color image-pixel signal and an average of values of circumferential third-type-single-color image-pixel signals surrounding the central third-type-single-color image-pixel signal, and the comparison system compares the value of the central first-type-single-color image-pixel signal, the value of the central second-type-single-color image-pixel signals, and the value of the central second-type-single-color image-pixel signals with each other, to thereby determine a maximum one of the three values. Also, the color-balance alteration system decreases the respective two values, except for the maximum value, in proportion to absolute values of the corresponding difference values when each of the two values is smaller than the corresponding average of values.

BRIEF DESCRIPTION OF THE DRAWINGS

The object and other objects of the present invention will be better understood from the following description, referring to the accompanying drawings, in which:

FIG. 2 is a conceptual view showing a frame of red digital image-pixel signals stored in a m×n matrix manner in a frame memory used in the first embodiment of the electronic endoscope system;

FIG. 5 is a timing chart for explaining an operation of the color-balance alteration circuit shown in FIG. 3;

FIG. 7 is a flowchart of a display-mode-selection-monitoring routine executed in a system control circuit included in a modification of the first embodiment of the electronic endoscope system;

FIG. 8 is a schematic block diagram of a second embodiment of an electronic endoscope system according to the present invention;

FIG. 27 is a timing chart for explaining an operation of the signal-generating circuit shown in FIG. 26;

FIG. 30 is a schematic block diagram of a comparator circuit included in a color-balance alteration processor shown in FIG. 29;

DESCRIPTION OF THE PREFERRED EMBODIMENTS

First Embodiment

Figure 1:
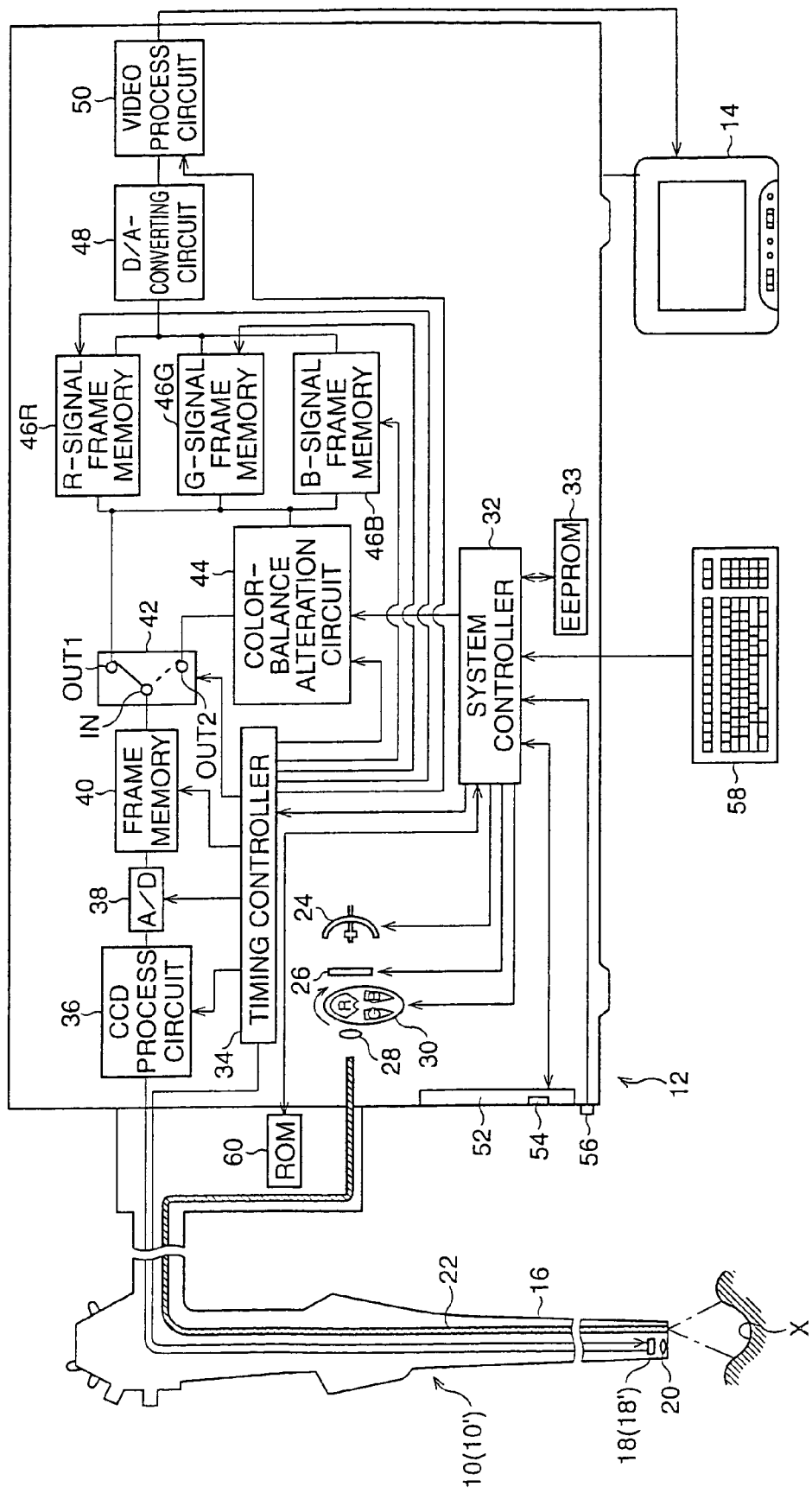
FIG. 1 is a schematic block diagram of a first embodiment of an electronic endoscope system according to the present invention.

Referring to FIG. 1, a first embodiment of an electronic endoscope system according to the present invention is shown as a block diagram. The electronic endoscope system comprises a video scope 10, an image-signal processing unit 12 to which the video scope 10 is detachably coupled, and a TV monitor 14 to which the image-signal processing unit 12 is connected. In this embodiment, at least two video scopes 10 use the image-signal processor 12 in common. This is because the scope 10 is detachably coupled to the image-signal processing unit 12.

The video scope 10 includes a flexible conduit 16 which is provided with a solid-state image sensor 18, such as a CCD (charge-coupled-device) image sensor, at the distal end thereof, and the CCD image sensor 18 is associated with an objective lens 20. When a connection is established between the video scope 10 and the image-signal processing unit 12, the CCD image sensor 18 is electrically connected to an image-signal processor provided in the image-signal processing unit 12.

Also, the video scope 10 includes a flexible optical light guide 22 which extends therethrough and which is formed as a bundle of optical fibers. The optical light guide 22 terminates with a light-radiating end face at the distal end of the flexible conduit 16, and is associated with a lighting lens system (not shown) provided thereat. When a connection is established between the video scope 10 and the image-signal processing unit 12, the proximal end of the optical light guide 22 is optically connected to a light source device provided in the image-signal processing unit 12, whereby the light, emitted from the light source device, radiates as an illuminating-light from the light-radiating end face of the optical light guide 22.

When the flexible conduit 16 of the video scope 10 is inserted in an organ of a patient, an illuminated object is focussed as an optical endoscope image on a light-receiving surface of the CCD image sensor 18, by the objective lens system 20 associated therewith. The focussed endoscope image is converted into a frame of analog image-pixel signals by the CCD image sensor 18, and the frame of analog image-pixel signals is sequentially read from the CCD image sensor 18. Then, the image-pixel signals are fed to an image-signal processor provided in the image-signal processing unit 12, and a video signal is produced based on the image-pixel signals, as discussed in detail hereinafter. Then, the video signal is fed from the image-signal processor to the TV monitor 14, and the endoscope image, sensed by the CCD image sensor 18, is reproduced as a motion picture on the TV monitor 14.

The light source device, provided in the image-signal processing unit 12, includes a white light lamp 24, such as a halogen lamp, a xenon lamp or the like, aligned with the proximal end of the light guide 22, a diaphragm 26 provided for adjusting an amount of light directed from the lamp 24 to the proximal end of the light guide 22, and a condenser lens 28 provided for focusing the light on the proximal end of the light guide 22.

In this embodiment, in order to reproduce an endoscope image as a full color motion picture on the TV monitor 14, an RGB field sequential-type color imaging method is used in the electronic endoscope system. To this end, the light source device further includes a rotary RGB color-filter 30 provided between the diaphragm 26 and the condenser lens 28, and the rotary RGB color-filter comprises a disk element having three sector-shaped color filters, i.e. red, green, and blue filters. These filters are circumferentially and uniformly arranged such that the three centers of the color filters are spaced at regular angular intervals of 120 degrees, and a sector area between the two adjacent color filters serves as a light-shielding area.

The rotary color-filter 30 is rotated at a given rotational frequency in accordance with a commonly used image-reproduction method, such as the NTSC method, the PAL method and so on. For example, in the NTSC method, the rotational frequency of the rotary color-filter 30 is 30 Hz, and, in the PAL method, the rotational frequency of the rotary color-filter 30 is 25 Hz.

Thus, during the rotation of the rotary color-filter 30, red, green, and blue lights are cyclically and sequentially made incident on the proximal end of the light guide 22, whereby the red, green, and blue lights are cyclically and sequentially emitted from the distal end face of the light guide 22. Namely, red, green, and blue endoscope images are sequentially and cyclically focused on the light-receiving surface of the CCD image sensor 18.

While the red, green, and blue endoscope images are cyclically focused on the light-receiving surface of the CCD image sensor 18 by the objective lens system 20, each of the red, green, and blue optical images is converted into a frame of monochromatic (red, green, blue) analog image-pixel signals by the CCD image sensor 18. Each frame of monochromatic analog image-pixel signals is read from the CCD image sensor 18 during the light-shielding time period which corresponds to the light-shielding area between two adjacent color filters of the rotary color-filter 30.

As shown in FIG. 1, the image-signal processing unit 12 is provided with a system control circuit 32 which controls the electronic endoscope system as a whole. The system control circuit 32 contains a microcomputer comprising a central processing unit (CPU), a read-only memory (ROM) for storing programs and constants, a random-access memory (RAM) for storing temporary data, and an input/output interface circuit (I/O). The image-signal processing unit 12 is further provided with a timing controller 34, which produces and outputs various series of clock pulses having given frequencies under the control of the system control circuit 32, thereby operating sequentially and systematically the aforesaid image-signal processor provided in the image-signal processing unit 12.

Note, as is apparent from FIG. 1, the turn-ON and turn-OFF of the lamp 24, the operation of the diaphragm 26, and the rotation of the rotary color-filter 30 are controlled by the system control circuit 32.

The image-signal processor, provided in the image-signal processing unit 12, includes a CCD process circuit 36. As shown in FIG. 1, when a connection is established between the video scope 10 and the image-signal processing unit 12, the CCD image sensor 18 is connected to the timing controller 34 and the CCD process circuit 36. The timing controller 34 produces and outputs a series of reading clock pulses to the CCD image sensor 18, whereby the three frames of monochromatic (red, green, and blue) analog image-pixel-signals are cyclically and sequentially read from the CCD image sensor 18. The read analog image-pixel-signals are fed to the CCD process circuit 36, in which the analog image-pixel-signals are subjected to various image-processings, such as gamma-correction, white-balance correction, profile-enhancing, noise-elimination, black-level-clamping and so on. For these various image-processings, the CCD process circuit 36 is operated in accordance with various series of clock pulses output from the timing controller 34.

The image-signal processor further includes an analog-to-digital (A/D) converter 38, a frame memory 40, a switching-circuit 42, a simulated dye-spraying process circuit or color-balance alteration circuit 44, an R-signal frame memory 46R, a G-signal frame memory 46G, a B-signal frame memory 46B, a digital-to-analog (D/A) converting circuit 48, and a video process circuit 50.

Each of the processed analog image-pixel signals is output from the CCD process circuit 36 to the A/D converter 38, in which the analog image-pixel signal concerned is converted into a digital image-pixel signal. The conversion of the analog image-pixel signal into the digital image-pixel signal is performed in accordance with a series of sampling clock pulses output from the timing controller 34.

Then, the digital image-pixel signal is temporarily stored in the frame memory 40. Namely, a frame of red digital image-pixel signals, a frame of green digital image-pixel signals, and a frame of blue image-pixel signals are cyclically stored in the frame memory 40 in accordance with a series of writing clock pulses output from the timing controller 34. While the digital image-pixel signals are successively stored in the frame memory 40, the digital image-pixel signals are read from the frame memory 40 in order, and the reading of the digital image-pixel signals from the frame memory 40 is performed in accordance with a series of writing clock pulses output from the timing controller 34 to the frame memory 40.

FIG. 2 conceptually shows, by way of example, a frame of red digital image-pixel signals $R_{11}, R_{12}, \ldots R_{m(n-1)}$, and $R_{mn}$, which are stored in a m×n matrix manner in the frame memory 40. Namely, a red image is formed by m lines, each of which includes n digital image-pixel signals. The red digital image-pixel signals $R_{11}, R_{12}, \ldots R_{m(n-1)}$, and $R_{mn}$ are read from the frame memory 40 in a line-reading direction and in a pixel-reading direction indicated by the arrows in FIG. 2, and are then fed to the switching-circuit 42. In this embodiment, each of the digital image-pixel signals $R_{11}, R_{12}, \ldots R_{m(n-1)}$, and $R_{mn}$ is composed of eight bits, and represents any one of 256 values. The same is true for the green digital image-pixel signals $G_{11}, G_{12}, \ldots G_{m(n-1)}$, and $G_{mn}$, and the blue digital image-pixel signals $B_{11}, B_{12}, \ldots B_{m(n-1)}$, and $B_{mn}$.

Note, the storage of the digital image-pixel signals in the frame memory 40 is performed in accordance with a series of writing-clock pulses output from the timing controller 34, and the reading of the digital image-pixel signals from the frame memory 40 is performed in accordance with a series of reading-clock pulses.

The switching-circuit 42 has an input terminal "IN", a first output terminal "OUT1", and a second output terminal "OUT 2". The switching of the connection of the input terminal "IN" from the first output terminal "OUT1" to the second output terminal "OUT2" and vice versa is performed by a switching pulse output from the timing controller 34.

In this embodiment, either a usual display mode or a simulated dye-spraying (SDS) display mode is selected. When the usual display mode is selected, the input terminal "IN" is connected to the first output terminal "OUT1", such that the digital image pixel-signal, read from the frame memory 40, is directly output from the first output terminal "OUT1" to any one of the R-signal, G-signal, and B-signal frame memories 46R, 46G, and 46B. Namely, when the digital image pixel-signal is red, it is stored in the R-signal frame memory 46R; when the digital image pixel-signal is green, it is stored in the G-signal frame memory 46G; and when the digital image pixel-signal is blue, it is stored in the B-signal frame memory 46B.

When the SDS display mode is selected, the input terminal "IN" is connected to the second output terminal "OUT2" such that the digital image-pixel signal, read from the frame memory 40, is fed to the color-balance alteration circuit 44, in which the digital image-pixel signal is subjected to a color-balance alteration process according to this invention, as explained in detail hereinafter. Then, the processed digital image-pixel signal is output from the color-balance alteration circuit 44 to any one of the R-signal, G-signal, and B-signal frame memories 46R, 46G, and 46B. Similar to the aforesaid case, when the processed digital image-pixel signal is red, it is stored in the R-signal frame memory 46R; when the processed digital image-pixel signal is green, it is stored in the G-signal frame memory 46G; and when the processed digital image-pixel signal is blue, it is stored in the B-signal frame memory 46B.

Note, the storage of the digital image-pixel signals in each frame memory (46R, 46G, 46B) is performed in accordance with a series of writing clock pulses output from the timing controller 34.

The red, green, and blue digital image-pixel signals are simultaneously read from the R-signal, G-signal, and B-signal frame memories 46R, 46G, and 46B, and are output to the D/A converting circuit 48. The D/A converting circuit 48 includes three digital-to-analog (D/A) converters, and the respective red, green, and blue digital image-pixel signals are simultaneously converted into red, green, and blue analog image signals by the three D/A converters.

Then, the red, green, and blue analog image signals are output from the D/A converting circuit 48 to the video process circuit 50. On the other hand, the timing controller 34 produces a composite synchronizing signal, and the composite synchronizing signal is output from the timing controller 34 to the video process circuit 50. Thus, the video process circuit 50 produces a component type video signal based on the red, green, and blue image signals output from the D/A converting circuit 48, and the synchronizing signal output from the timing controller 34.

In the video process circuit 50, the component type video signal is subjected to various image-processings, such as high frequency noise-elimination, profile-enhancing, and so on. Then, the processed component type video signal is fed from the video process circuit 50 to the TV video monitor 14. Thus, an optical endoscope image, successively captured by the CCD image sensor 18, is reproduced as a full color motion picture on the TV monitor 14.

While the usual display mode is selected, the endoscope image is reproduced on the TV monitor 14 with a given proper color balance. However, while the SDS display mode is selected, the endoscope image is observed on the TV monitor 14 as if it were sprayed with a blue-solution, due to the color-balance alteration process of the red and green digital image-pixel signals in the color-balance alteration circuit 44, as stated hereinafter.

Note, the video process circuit 50 may include a color encoder for producing various video signals, such as, a S-video signal, a composite type video signal and so on, based on the component type video signal.

In FIG. 1, reference 52 indicates a front panel attached to a front wall of a housing of the image-signal processing unit 12, and the front panel 52 includes various switches. A switch, which especially relates to the present invention, is a display-mode selection switch 54. Also, reference 56 indicates a power ON/OFF switch provided on the front wall of the housing of the image-signal processing unit 12.

The display-mode selection switch 54 is provided for selecting either the usual display mode or the SDS display mode. The display-mode selection switch 54 is constituted to alternately output a high-level signal or a low-level signal to the system control circuit 32 whenever it is operated. When the high-level signal is output from the display-mode selection switch 54, the system control circuit 32 recognizes that the SDS display mode is selected. When the low-level signal is output from the display-mode selection switch 54, the system control circuit 32 recognizes that the usual display mode is selected. In short, whenever the display-mode selection switch 54 is operated, the usual display mode and the SDS display mode are alternately selected.

When the power ON/OFF switch 56 is turned ON, the image-signal processing unit 12 is supplied with electric power from a commercial power source. Note, when the power ON/OFF switch 56 is turned ON, the low-level signal is output from the display-mode selection switch 54, and the usual display mode is forcibly selected.

As shown in FIG. 1, a keyboard 58 is connected to the system control circuit 32 of the image-signal processing unit 12 to input various commands and various data to the system control circuit 32. A function, pertaining to the display-mode selection switch 54, may be allocated to a function key on the keyboard 58. When the display-mode selection is performed by the function key on the keyboard 58, the display-mode selection switch 54 may be eliminated from the front panel 52.

Figure 3:
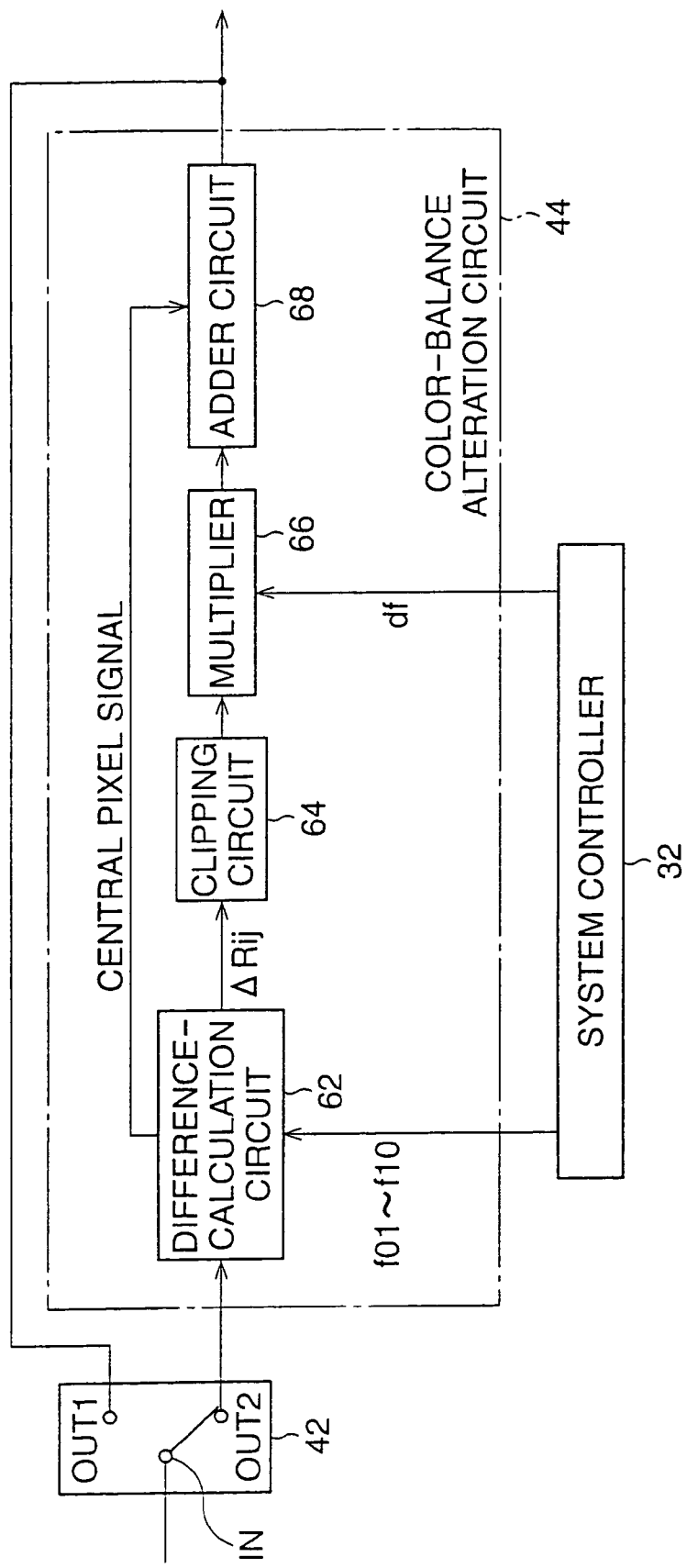
FIG. 3 is a schematic block diagram of a color-balance alteration circuit used as a simulated dye-spraying process circuit in the first embodiment of the electronic endoscope system.

FIG. 3 shows a block diagram of the color-balance alteration circuit 44. The color-balance alteration circuit 44 comprises a difference-calculation circuit, generally indicated by reference 60. The difference-calculation circuit 60 includes a delay circuit arrangement constituted by first and second one-line delay circuits LDL1 and LDL2, and first, second, third, fourth, fifth, and sixth one-pixel delay circuits PDL1, PDL2, PDL3, PDL4, PDL5, and PDL6, which are arranged as shown in FIG. 3. The difference-calculation circuit 60 also includes first, second, third, fourth, and fifth adders ADD1, ADD2, ADD3, ADD4, and ADD5 associated with the delay circuit arrangement as shown in FIG. 3. The difference-calculation circuit 60 is further provided with a multiplier circuit 62, and an adder circuit 64.

As mentioned above, when the SDS display mode is selected, the input terminal "IN" of the switching-circuit 42 is connected to the second output terminal "OUT2". Thus, a digital image-pixel signal, read from the frame memory 40, is input to the first one-line delay circuit LDL1, the first one-pixel delay circuit PDL1, and the first adder ADD1.

The first one-line delay circuit LDL1 outputs the input digital image-pixel signal after a time necessary for reading one line of digital image-pixel signals from the frame memory 40 has elapsed. Namely, the outputting of the digital image-pixel signal from the first one-line delay circuit LDL1 is delayed for the reading time of the one line of digital image-pixel signals. The same is true for the second one-line delay circuit LDL2.

On the other hand, the first one-pixel delay circuit PDL1 outputs the input digital image-pixel signal after a time necessary for reading one digital image-pixel signal from the frame memory 40 has elapsed. Namely, the outputting of the digital image-pixel signal from the first one-pixel delay circuit PDL1 is delayed for the reading time of the one digital image-pixel signal. The same is true for each of the remaining one-pixel delay circuits PDL2, PDL3, PDL4, PDL5, and PDL6.

Figure 4:
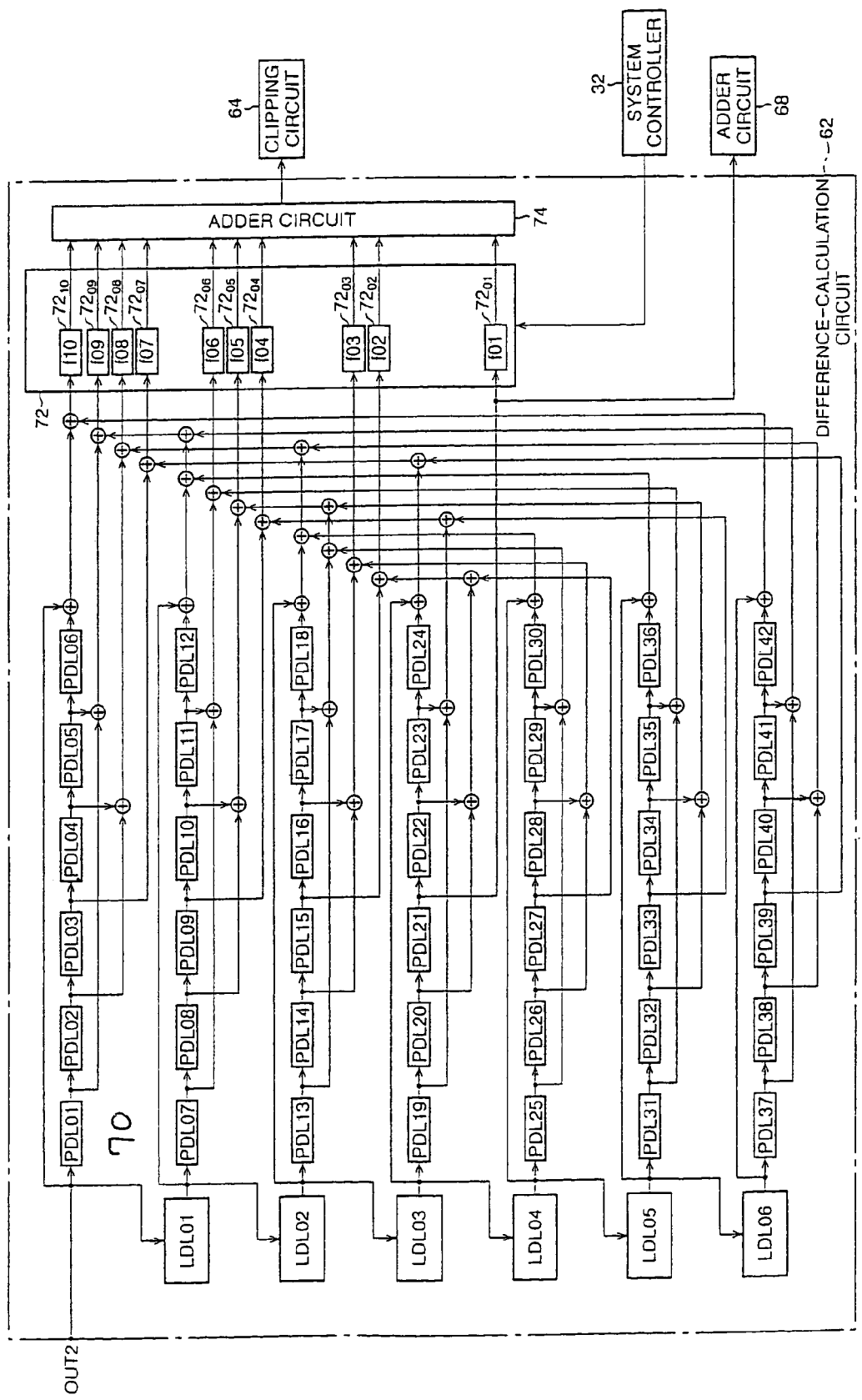
FIG. 4 is a conceptual view showing nine digital image-pixel signals in a 3×3 matrix, obtained in the color-balance alteration circuit.

Thus, while the red digital image-pixel signals $R_{11}$, $R_{12}$, ... $R_{m(n-1)}$, and $R_{mn}$ are successively fed one by one from the frame memory 40 to the color-balance alteration circuit 44, a set of nine red digital image-pixel signals $R_{(i-1)(j-1)}$, $R_{(i-1)j}$, $R_{(i-1)(j+1)}$, $R_{i(j-1)}$, $R_{ij}$, $R_{i(j+1)}$, $R_{(i+1)(j-1)}$, $R_{(i+1)j}$, and $R_{(i+1)(j+1)}$ is produced in the delay circuit arrangement 60 ($2 \leq i \leq (m-1)$, $2 \leq j \leq (n-1)$). Namely, these red digital image-pixel signals forms a 3×3 matrix in the delay circuit arrangement 60, as shown in FIG. 4.

In particular, when the pixel signal $R_{(i+1)(j+1)}$ is input to the delay circuit arrangement 60, the pixel signal $R_{(i-1)(i-1)}$ is output from the sixth one-pixel delay circuit PDL6; the pixel signal $R_{(i-1)j}$ is output from the fifth one-pixel delay circuit PDL5; the pixel signal $R_{(i-1)(j+1)}$ is output from the second one-line delay circuit LDL2; the pixel signal $R_{i(j-1)}$ is output from the fourth one-pixel delay circuit PDL4; the pixel signal $R_{ij}$ is output from the third one-pixel delay circuit PDL3; the pixel signal $R_{i(j+1)}$ is output from the second one-line delay circuit LDL1; the pixel signal $R_{(i+1)(j-1)}$ is output from the second one-pixel delay circuit PDL2; and the pixel signal $R_{(i+1)j}$ is output from the first one-pixel delay circuit PDL1. As shown in FIG. 4, the pixel signal $R_{ij}$ forms a central pixel signal surrounded by the remaining eight circumferential pixel signals $R_{(i-1)(j-1)}$, $R_{(i-1)j}$, $R_{(i-1)(j+1)}$, $R_{i(j-1)}$, $R_{i(j+1)}$, $R_{(i+1)(j-1)}$, $R_{(i+1)j}$, and $R_{(i+1)(j+1)}$.

For example, when the red digital image-pixel signal $R_{33}$ is input to the delay circuit arrangement 60, the red digital image-pixel signals $R_{32}$ and $R_{31}$ are respectively output from the first and second one-pixel delay circuits PDL1 and PDL2; the red digital image-pixel signals $R_{23}$, $R_{22}$, and $R_{21}$ are respectively output from the first one-line delay circuit LDL1 and the third and fourth one-pixel delay circuits PDL3 and PDL4; and the red digital image-pixel signals $R_{13}$, $R_{12}$, and $R_{11}$ are respectively output from the second one-line delay circuit LDL2 and the fifth and sixth one-pixel delay circuits PDL5 and PDL6. In this case, as shown in FIG. 2, the pixel signal $R_{22}$ ($R_{ij}$) or central pixel signal is surrounded by the other eight circumferential pixel signals $R_{11}$, $R_{12}$, $R_{13}$, $R_{21}$, $R_{23}$, $R_{31}$, $R_{32}$, and $R_{33}$.

As is apparent from FIG. 3, the red digital image-pixel signals $R_{11}$ and $R_{13}$ are input to the fifth adder ADD5, in which the values of the pixel signals $R_{11}$ and $R_{13}$ are summed, and then the sum of the values ($R_{11}+R_{13}$) is output to the first adder ADD1. Also, the red digital image-pixel signals $R_{31}$ and $R_{33}$ are input to the first adder ADD1. Thus, in the first adder ADD1, the values of the pixel signals $R_{11}$, $R_{13}$, $R_{31}$, and $R_{33}$ are summed.

On the other hand, the red digital image-pixel signals $R_{21}$ and $R_{23}$ are input to the fourth adder ADD4, in which the values of the pixel signals $R_{21}$ and $R_{23}$ are summed, and then the sum of the values ($R_{21}+R_{23}$) is output to the third adder ADD3. Also, the red digital image-pixel signal $R_{12}$ is input to the third adder ADD3, and thus the values of the pixel signals $R_{12}$, $R_{21}$, and $R_{23}$ are summed in the third adder ADD3. Then, the sum of the values ($R_{12}+R_{21}+R_{23}$) is output to the second adder ADD2. The red digital image-pixel signal $R_{32}$ is further input to the second adder ADD2. Thus, in the second adder ADD2, the values of the pixel signals $R_{12}$, $R_{21}$, $R_{23}$, and $R_{32}$ are summed.

As shown in FIG. 3, the multiplier circuit 62 has first, second, and third multipliers $62_1$, $62_2$, and $62_3$. A factor "$-\frac{1}{8}$" is previously set in each of the first and second multipliers $62_1$, and $62_2$, and a factor "1" is previously set in the third multiplier $62_3$. The sum of the values ($R_{11}+R_{13}+R_{31}+R_{33}$) is input from the first adder ADD1 to the first multiplier $62_1$, in which the sum of the values ($R_{11}+R_{13}+R_{31}+R_{33}$) is multiplied by the factor "$-\frac{1}{8}$". Also, the sum of the values ($R_{12}+R_{21}+R_{23}+R_{32}$) is input from the second adder ADD2 to the second multiplier $62_2$, in which the sum of the values ($R_{12}+R_{21}+R_{23}+R_{32}$) is multiplied by the factor "$-\frac{1}{8}$". The central pixel signal $R_{22}$ is directly input from the third one-pixel delay circuit PDL3 to the third multiplier $62_3$, in which the value of the pixel signal $R_{22}$ is multiplied by the factor "1".

The respective first, second and third multipliers $62_1$, $62_2$, and $62_3$ output the multiplied results $[-(R_{11}+R_{13}+R_{31}+R_{33})/8]$, $[-(R_{12}+R_{21}+R_{23}+R_{32})/8]$, and $[R_{22}]$ to the adder circuit 64, in which the following calculation is performed:

$$\Delta R_{22} = [R_{22} - (R_{11}+R_{12}+R_{13}+R_{21}+R_{23}+R_{31}+R_{32}+R_{33})/8]$$

Namely, by the difference-calculation circuit 60, a difference $\Delta R_{ij}$ between a value of a central digital image-pixel signal $R_{ij}$ and an average value of circumferential digital image-pixel signals $R_{(i-1)(j-1)}$, $R_{(i-1)j}$, $R_{(i-1)(j+1)}$, $R_{i(j-1)}$, $R_{i(j+1)}$, $R_{(i+1)(j-1)}$, $R_{(i+1)j}$, and $R_{(i+1)(j+1)}$ is successively calculated.

When the difference $\Delta R_{ij}$ is minus, the value of the central digital image-pixel signal $R_{ij}$ is lower than the average value of the circumferential digital image-pixel signals $R_{(i-1)(j-1)}$, $R_{(i-1)j}$, $R_{(i-1)(j+1)}$, $R_{i(j-1)}$, $R_{i(j+1)}$, $R_{(i+1)(j-1)}$, $R_{(i+1)j}$, and $R_{(i+1)(j+1)}$. This means that the central digital image-pixel signal $R_{ij}$ derives from a fine recess area X on a mucous membrane surface of, for example, a stomach or a colon, as shown conceptually and symbolically in FIG. 1, because the value of an image-pixel signal, deriving from the fine recess area X, is lower than the value of an image-pixel signal deriving from a land area surrounding the fine recess area X.

When the difference $\Delta R_{ij}$ is zero or plus, the value of the central digital image-pixel signal $R_{ij}$ is equal to or higher than the average value of the circumferential digital image-pixel signals $R_{(i-1)(j-1)}$, $R_{(i-1)j}$, $R_{(i-1)(j+1)}$, $R_{i(j-1)}$, $R_{i(j+1)}$, $R_{(i-1)(j-1)}$, $R_{(i+1)j}$, and $R_{(i+1)(j+1)}$. This means that the central digital image-pixel signal $R_{ij}$ derives from either a flat area or a land area on the mucous membrane surface of the stomach or the colon.

Of course, when the green digital image-pixel signals $G_{11}$, $G_{12}$, ... $G_{m(n-1)}$, and $G_{mn}$ are fed from the frame memory 40 to the difference-calculation circuit 60, a difference $\Delta G_{ij}$ between a value of a central digital image-pixel signal $G_{ij}$ and an average value of the eight circumferential digital image-pixel signals $G_{(i-1)(j-1)}$, $G_{(i-1)j}$, $G_{(i-1)(j+1)}$, $G_{i(j-1)}$, $G_{i(j+1)}$, $G_{(i+1)(j-1)}$, $G_{(i+1)j}$, and $G_{(i+1)(j+1)}$ is successively calculated. Also, when the blue digital image-pixel signals $B_{11}$, $B_{12}$, ... $B_{m(n-1)}$, and $B_{mn}$ are fed from the frame memory 40 to the difference-calculation circuit 60, a difference $\Delta B_{ij}$ between a value of a central digital image-pixel signal $B_{ij}$ and an average value of the eight circumferential digital image-pixel signals $B_{(i-1)(j-1)}$, $B_{(i-1)j}$, $B_{(i-1)(j+1)}$, $B_{i(j-1)}$, $B_{i(j+1)}$, $B_{(i+1)(j-1)}$, $B_{(i+1)j}$, and $B_{(i+1)(j+1)}$ is successively calculated.

The color-balance alteration circuit 44 further includes a clipping circuit 66, a multiplier circuit 68, a selector circuit 70, and an adder circuit 72.

The difference or value $\Delta R_{ij}$ is output from the adder circuit 64 to the clipping circuit 66, in which a zero is set as the clipping level. Namely, when the difference $\Delta R_{ij}$ is either zero or plus, it is output as a zero signal from the clipping circuit 66 to the multiplier circuit 68. On the other hand, when the difference $\Delta R_{ij}$ is minus, it is output as a minus signal from the clipping circuit 66 to the multiplier circuit 68. In short, only the minus differences ($\Delta R_{ij}$) included in a frame can pass through the clipping circuit 66 as they stand, and all the remaining differences ($\Delta R_{ij}$) included in a frame are output as zero signals from the clipping circuit 66.

The multiplier circuit 68 has a first multiplier 68$_1$ and a second multiplier 68$_2$, in which respective density factors "df1" and "df2" are set. Each of the density factors "df1" and "df2" can be varied by operating the keyboard 58. Namely, each of the density factors "df1" and "df2" is input to the system control circuit 32 by operating the keyboard 58, and then the input density factor (df1, df2) is set in a corresponding multiplier (68$_1$, 68$_2$) by the system control circuit 32. In this embodiment, a setting of a plus value, for example, "20" is given to the density factor "df1" in the first multiplier 681, and a setting of a minus value, for example, "–20" is given to the density factor "df2" in the second multiplier 68$_2$.

As is apparent from FIG. 3, the difference $\Delta R_{ij}$, output from the clipping circuit 66, is input to both the first and second multipliers 68$_1$ and 68$_2$, in which the respective differences $\Delta R_{ij}$ are multiplied by the density factors "df1" and "df2". Namely, the first and second multipliers 68$_1$ and 68$_2$ respectively output the products df1*$\Delta R_{ij}$ and df2*$\Delta R_{ij}$ as digital signals. Thus, the first multiplier 68$_1$ cyclically outputs a frame of red signals (df1*$\Delta R_{ij}$), a frame of green signals (df1*$\Delta G_{ij}$), and a frame of blue signals (df1*$\Delta B_{ij}$), and the second multiplier 68$_2$ cyclically outputs a frame of red signals (df2*$\Delta R_{ij}$), a frame of green signals (df2*$\Delta G_{ij}$), and a frame of blue signals (df2*$\Delta B_{ij}$), as indicated by items (a) and (b) in a timing chart of FIG. 5. Of course, each of the signals (df1*$\Delta R_{ij}$, df1*$\Delta G_{ij}$, df1*$\Delta B_{ij}$), output from the first multiplier 68$_1$, exhibits either zero or minus, and each of the signals (df2*$\Delta R_{ij}$, df2*$\Delta G_{ij}$, df2*$\Delta B_{ij}$), output from the second multiplier 68$_2$, exhibits either zero or plus.

Both the three frames of red, green, and blue digital signals (df1*$\Delta R_{ij}$, df1*$\Delta G_{ij}$, and df1$\Delta B_{ij}$) and the three frames of red, green, and blue digital signal (df2*$\Delta R_{ij}$, df2*$\Delta G_{ij}$, and df2*$\Delta B_{ij}$) are cyclically and correspondingly input to the selector circuit 70, and only one of two frames of digital signals (df1*$\Delta R_{ij}$ and df2*$\Delta R_{ij}$; df1*$\Delta G_{ij}$ and df2*$\Delta G_{ij}$; and df1*$\Delta B_{ij}$ and df2*$\Delta B_{ij}$), corresponding to each other, is output from the selector circuit 70. The selector circuit 70 is operated in accordance with a selecting-signal, indicated by item (c) in the timing chart of FIG. 5, output by the system control circuit 32. While the selecting-signal is at a high level "H", the selector circuit 70 outputs the frame of digital signals (df1*$\Delta R_{ij}$, df1*$\Delta G_{ij}$, df1*$\Delta B_{ij}$) obtained from the first multiplier 68$_1$, and, while the selecting-signal is at a low level "L", the selector circuit 70 outputs the frame of digital signals (df2*$\Delta R_{ij}$, df2*$\neq G_{ij}$, df2*$\Delta B_{ij}$) obtained from the second multiplier 68$_2$.

As is apparent from the timing chart of FIG. 5, while the frame of red signals (df1*$\Delta R_{ij}$) and the frame of green signals (df1*$\Delta G_{ij}$) are output from the first multiplier 68$_1$, the selecting-signal is maintained at the high level "H", and, while the frame of blue signals (df2*$\Delta B_{ij}$) is output from the second multiplier 68$_2$, the level of the selecting-signal is changed from the high level "H" to the low level "L". Thus, the frame of red signals (df1*$\Delta R_{ij}$), the frame of green signals (df1*$\Delta G_{ij}$), and the frame of blue signals (df2*$\Delta B_{ij}$) are cyclically output from the selector circuit 70, as indicated by item (d) in the timing chart of FIG. 5.

As is apparent from FIG. 3, when a digital signal (df1*$\Delta R_{ij}$, df1*$\Delta G_{ij}$, df2*$\Delta B_{ij}$) is input from the selector circuit 70 to the adder circuit 72, a corresponding central digital image-pixel signal ($R_{ij}$, $G_{ij}$, $B_{ij}$) is input to the adder circuit 72. Namely, while the three frames of red, green, blue signals (df1*$\Delta R_{ij}$, df1*$\Delta G_{ij}$, and df2*$\Delta B_{ij}$) are cyclically output from the selector circuit 70 to the adder circuit 72, the three frames of red, green, and blue image-pixel signals ($R_{ij}$, $G_{ij}$, and $B_{ij}$) are cyclically output from the third one-pixel delay circuit PDL3 to the adder circuit 72. In the adder circuit 72, the frame of red image-pixel signals ($R_{ij}$) is added to the frame of red signals (df1*$\Delta R_{ij}$); the frame of green image-pixel signals ($G_{ij}$) is added to the frame of green signals (df1*$\Delta G_{ij}$); and the frame of blue image-pixel signals ($B_{ij}$) is added to the frame of blue signals (df2*$\Delta B_{ij}$). Namely, in the adder circuit 72, the following calculations are performed:

$$R_{ij} = R_{ij} + df1 * \Delta R_{ij}$$

$$G_{ij} = G_{ij} + df1 * \Delta G_{ij}$$

$$B_{ij} = B_{ij} + df2 * \Delta B_{ij}$$

As mentioned above, if $\Delta R_{ij} \geq 0$, $\Delta R_{ij} = 0$. Thus, if $\Delta R_{ij} > 0$, the red image-pixel signal $R_{ij}$ is output from the adder circuit 72 as it stands. If $\Delta R_{ij} < 0$, the absolute value of the signal df1*$\Delta R_{ij}$ is subtracted from the value of the red image-pixel signal $R_{ij}$ (df1>0). Similarly, if $\Delta G_{ij} \geq 0$, the green image-pixel signal $G_{ij}$ is output from the adder circuit 72 as it stands. If $\Delta G_{ij} < 0$, the absolute value of the green signal df1*$\Delta G_{ij}$ is subtracted from the value of the green image-pixel signal $G_{ij}$ (df1>0).

If $\Delta B_{ij} \geq 0$, $\Delta B_{ij} = 0$. Namely, if $\Delta B_{ij} \geq 0$, the blue image-pixel signal $B_{ij}$ is output from the adder circuit 72 as it stands. However, if $\Delta B_{ij} < 0$, the absolute value of the blue signal df2*$\Delta B_{ij}$ is added to the value of the blue image-pixel signal $B_{ij}$ (df2<0).

Accordingly, when the differences $\Delta R_{ij}$, $\Delta G_{ij}$, and $\Delta B_{ij}$ are minus, i.e. when the color image-pixel signals $R_{ij}$, $G_{ij}$, and $B_{ij}$ are derived from the fine recess area X, the respective values of the red and green image-pixel signals $R_{ij}$ and $G_{ij}$ are decreased in proportion to the magnitude of the absolute values of the red and green signals df1*$\Delta R_{ij}$ and df1*$\Delta G_{ij}$, but the value of the blue image-pixel signal $B_{ij}$ is increased in proportion to the magnitude of the absolute values of the blue signal df2*$\Delta B_{ij}$. Therefore, when the SDS display mode is selected, a color image-pixel on the TV monitor 14, represented by the color image-pixel signals $R_{ij}$, $G_{ij}$, and $B_{ij}$, becomes bluish. Namely, a bluish endoscope image is observed on the TV monitor 14 as if an endoscope image, sensed by the CCD image sensor 18, were sprayed with a blue-solution.

In the simulated dye-spraying process disclosed in the aforesaid JPP(2001-25025), when the red, green, and blue image-pixel signals are derived from a fine recess area on a mucous membrane surface of the stomach or the colon, only the values of the red and green image-pixel signals are decreased, but the value of the blue image-pixel signal is unchanged.

In general, a luminance image-pixel signal is produced by summing the respective values of the red, green, and blue image-pixel signals at a 0.3:0.59:0.11 ratio. Thus, in the aforesaid JPP(2001-25025), when a simulated dye-spraying display mode is selected, the brightness of a reproduced endoscope image on a TV monitor is considerably lowered. However, according to the first embodiment of the present invention, a brightness of the reproduced endoscope image on the TV monitor 14 cannot be lowered in the SDS display mode, due to the increase in the value of the blue image-pixel signal $B_{ij}$ in proportion to the magnitude of the absolute values of the blue signal df2*$\Delta B_{ij}$.

In the first embodiment, although it is necessary to give the respective settings of plus and minus values to the density factors "df1" and df2 in the first and second multipliers 68₁ and 68₂, the absolute values of the density factors "df1" and "df2" do not necessarily have to be coincident with each other. Also, a value of each density factor (df1, df2) may be optionally and independently varied. Note, the varying of the value of the density factor (df1, df2) corresponds to use of a blue-dye solution having a different blue density.

Figure 6:
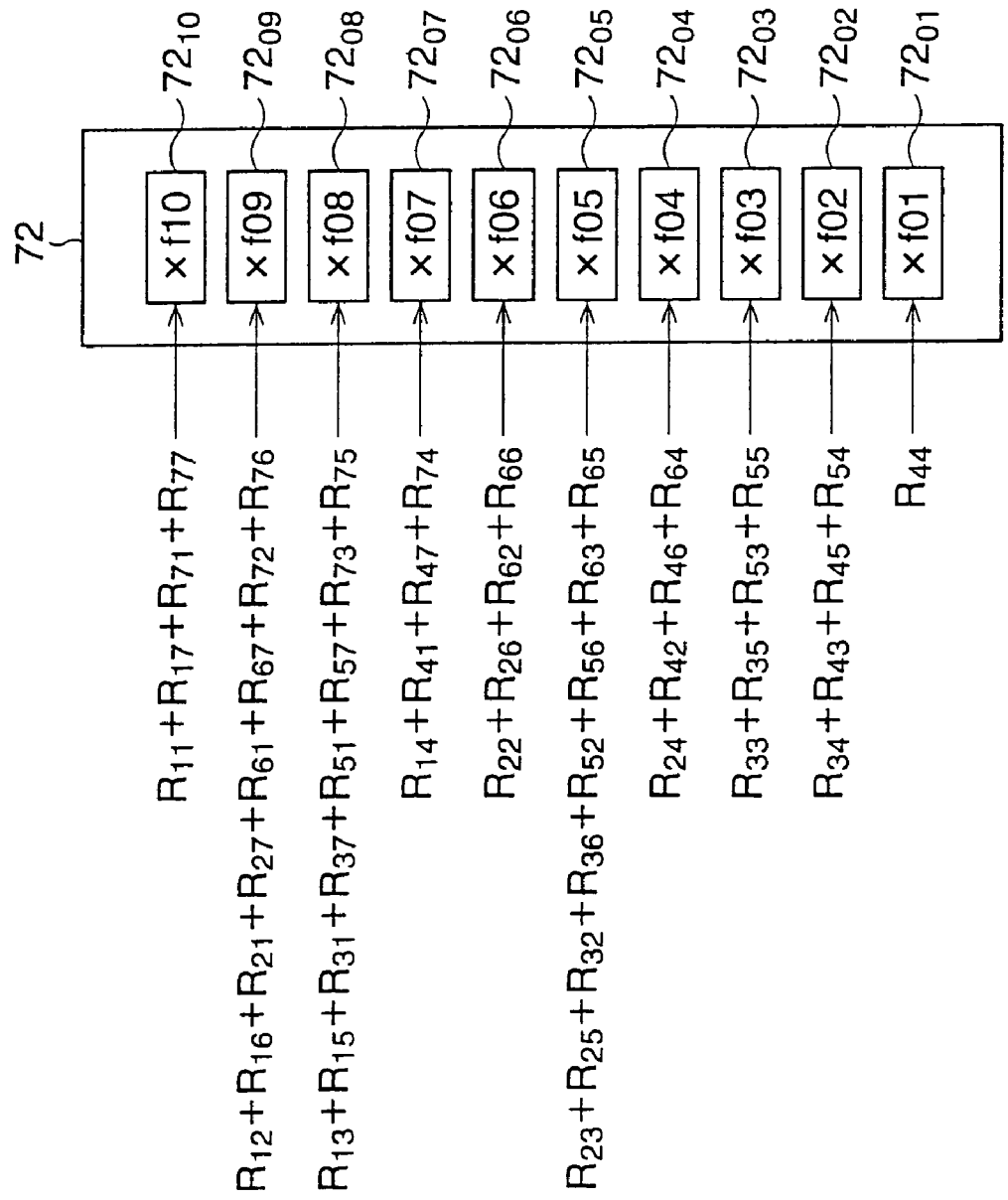
FIG. 6 is a flowchart of a display-mode-selection-monitoring routine executed in a system control circuit included in the first embodiment of the electronic endoscope system.

FIG. 6 shows a flowchart of a display-mode-selection-monitoring routine, which is formed as a time-interruption routine executed in the system control circuit 32 at regular suitable intervals of, for example, 20 ms. The execution of the routine is started after the power ON/OFF switch 56 is turned ON, and is repeated every 20 ms as long as the power ON/OFF switch 56 is turned ON.

At step 601, it is monitored whether either the usual display mode or the SDS display mode has been changed to the other display mode by operating either the display mode selection switch 54 or the function key concerned on the keyboard 58. When the change of the display mode is not confirmed, the routine immediately ends. Although the routine is repeatedly executed every 20 ms, there is no progress until the change of the display mode is confirmed.

At step 601, when it is confirmed that the display mode has been changed, the control proceeds to step 602, in which it is determined whether the usual display mode has been selected. When the selection of the usual display mode is confirmed, the control proceeds to step 603, in which the input terminal "IN" of the switching-circuit 42 is connected to the first output terminal "OUT1".

At step 602, when the selection of the usual display mode is not confirmed, i.e. when it is confirmed that the SDS display mode has been selected, the control proceeds from step 602 to step 604, in which the input terminal "IN" of the switching-circuit 42 is connected to the first output terminal "OUT2" thereof.

Note, as mentioned above, whenever the power ON/OFF switch 56 is turned ON, the usual display mode is forcibly selected, and thus the input terminal "IN" of the switching-circuit 42 is connected to the first output terminal "OUT1" thereof.

In the first embodiment, the switching-circuit 42 may be optionally omitted from the image-signal processor in the image-signal processing unit 12. In this case, the frames of red, green, and blue image-pixel signals ($R_{ij}$, $G_{ij}$, and $B_{ij}$) are cyclically fed from the frame memory 40 to the color-balance alteration circuit 44, regardless of the selection of either the usual display mode or the SDS display mode, provided that the setting of "0" is forcibly given to both the density factors "df1" and "df2" in the first and second multipliers 68₁, and 68₂ during the selection of the usual display mode. Namely, during the selection of the usual display mode, the frames of red, green, and blue image-pixel signals ($R_{ij}$, $G_{ij}$, and $B_{ij}$) can pass through the color-balance alteration circuit 44 without being subjected to any color-balance alteration process, due to the setting of "0" to the density factors "df1" and "df2" in the first and second multipliers 68₁, and 68₂.

Namely, when the density factors "df1" and "df2" are zero, all the digital color signals (df1*$\Delta R_{ij}$, df1*$\Delta G_{ij}$, and df2*$\Delta B_{ij}$) are output as the zero value from the selector circuit 70 to the adder circuit 72. Thus, the frames of red, green, and blue image-pixel signals ($R_{ij}$, $G_{ij}$, and $B_{ij}$) are output from the adder circuit 72 to the frame memories 46R, 46G, and 46B without being subjected to any color-balance alteration process.

FIG. 7 shows a flowchart of a display-mode-selection-monitoring routine, which is executed in the system control circuit 32 when the switching-circuit 42 is eliminated. This routine is also formed as a time-interruption routine executed at regular suitable intervals of, for example, 20 ms. The execution of the routine is started after the power ON/OFF switch 56 is turned ON, and is repeated every 20 ms as long as the power ON/OFF switch 56 is turned ON.

At step 701, it is monitored whether either the usual display mode or the SDS display mode has been changed to the other display mode by operating either the display mode selection switch 54 or the function key concerned on the keyboard 58. When the change of the display mode is not confirmed, the routine immediately ends. Although the routine is repeatedly executed every 20 ms, there in no progress until the change of the display mode is confirmed.

At step 701, when it is confirmed that the display mode has been changed, the control proceeds to step 702, in which it is determined whether the usual display mode has been selected. When the selection of the usual display mode is confirmed, the control proceeds to step 703, in which the setting of "0" is given to the density factors "df1" and "df2" in the first and second multipliers 68₁ and 68₂.

At step 702, when the selection of the usual display mode is not confirmed, i.e. when it is confirmed that the SDS display mode has been selected, the control proceeds from step 702 to step 704, in which the respective settings of "–20" and "20" are given to the density factors "df1" and "df2" in the first and second multipliers 68₁ and 68₂.

Note, since the usual display mode is forcibly selected whenever the power ON/OFF switch 56 is turned ON, the setting of "0" to both the density factors "df1" and "df2" is automatically performed after the turn-ON of the power ON/OFF switch 56.

Second Embodiment

Referring to FIG. 8, a second embodiment of an electronic endoscope system according to the present invention is shown as a block diagram. In this drawing, the features similar to those of FIG. 1 are indicated by the same references.

In the second embodiment, an on-chip color filter method (i.e., a simultaneous imaging method) is introduced to reproduce an endoscope image as a full color image on a TV monitor 14, instead of the RGB field sequential-type color imaging method, and a video scope 10 and an image-signal processing unit 12 are modified so as to conform to the on-chip color filter method.

In particular, a CCD image sensor 18 has a complementary color filter (not shown) provided on a light-receiving surface thereof. Also, a light source device, provided in the image-signal processing unit 12, is formed by a white light lamp 24, a diaphragm 26, and a condenser lens 28. Namely, the rotary color-filter 30 is eliminated from the light source device. Thus, white light is irradiated as an illuminating-light from a distal end face of an optical light guide 22. An illuminated object is focussed as an optical endoscope image on the light-receiving surface of the CCD image sensor 18 through the complementary color filter by an objective lens system 20, and the focussed endoscope image is converted into a frame of analog color image-pixel signals due to the existence of the complementary color filter.

In the second embodiment, the image-signal processing unit 12 is also provided with a system control circuit 32 which controls the electronic endoscope system as a whole, and a timing controller 34 which outputs various series of clock pulses having given frequencies under the control of the system control circuit 32, to thereby operate sequentially and systematically an image-signal processor provided in the image-signal processing unit 12.

In the second embodiment, the image-signal processor, provided in the image-signal processing unit 12, includes a CCD process circuit 36, an analog-to-digital (A/D) converter 38, a frame memory 40, an RGB-converting circuit 74, a first color-balance alteration circuit 76R, a second color-balance alteration circuit 76G, a third color-balance alteration circuit 76B, a digital-to-analog (D/A) converting circuit 48, and a video process circuit 50.

Similar to the first embodiment, when the connection between the video scope 10 and the image-signal processing unit 12 is established, the CCD image sensor 18 is connected to the timing controller 34 and the CCD process circuit 36. The timing controller 34 produces and outputs a series of reading clock pulses to the CCD image sensor 18, whereby the frame of analog color image pixel-signals is sequentially and successively read from the CCD image sensor 18. The read analog color image pixel-signals are fed to the CCD process circuit 36, in which the analog color image pixel-signals are subjected to various image-processings, such as gamma-correction, white-balance correction, profile-enhancing, noise-elimination, black-level-clamping and so on. For these various image-processings, the CCD process circuit 36 is operated in accordance with various series of clock pulses output from the timing controller 34.

Each of the processed analog image-pixel signals is output from the CCD process circuit 36 to the A/D converter 38, in which the analog image-pixel signal concerned is converted into a digital image-pixel signal. The A/D converter 38 successively outputs digital color image-pixel signals, which are temporarily stored in the frame memory 40. The digital color image-pixel signals are successively read from the frame memory 40, and are then fed to the RGB-converting circuit 74, in which the digital color image-pixel signals are processed to thereby produce a red digital image-pixel signal, a green digital image-pixel signal, and a blue digital image-pixel signal. The produced red, green, and blue digital image-pixel signals R, G, and B are simultaneously output from the RGB-converting circuit 74 to the respective first, second, and third color-balance alteration circuits 76R, 76G, and 76B.

Figure 9:
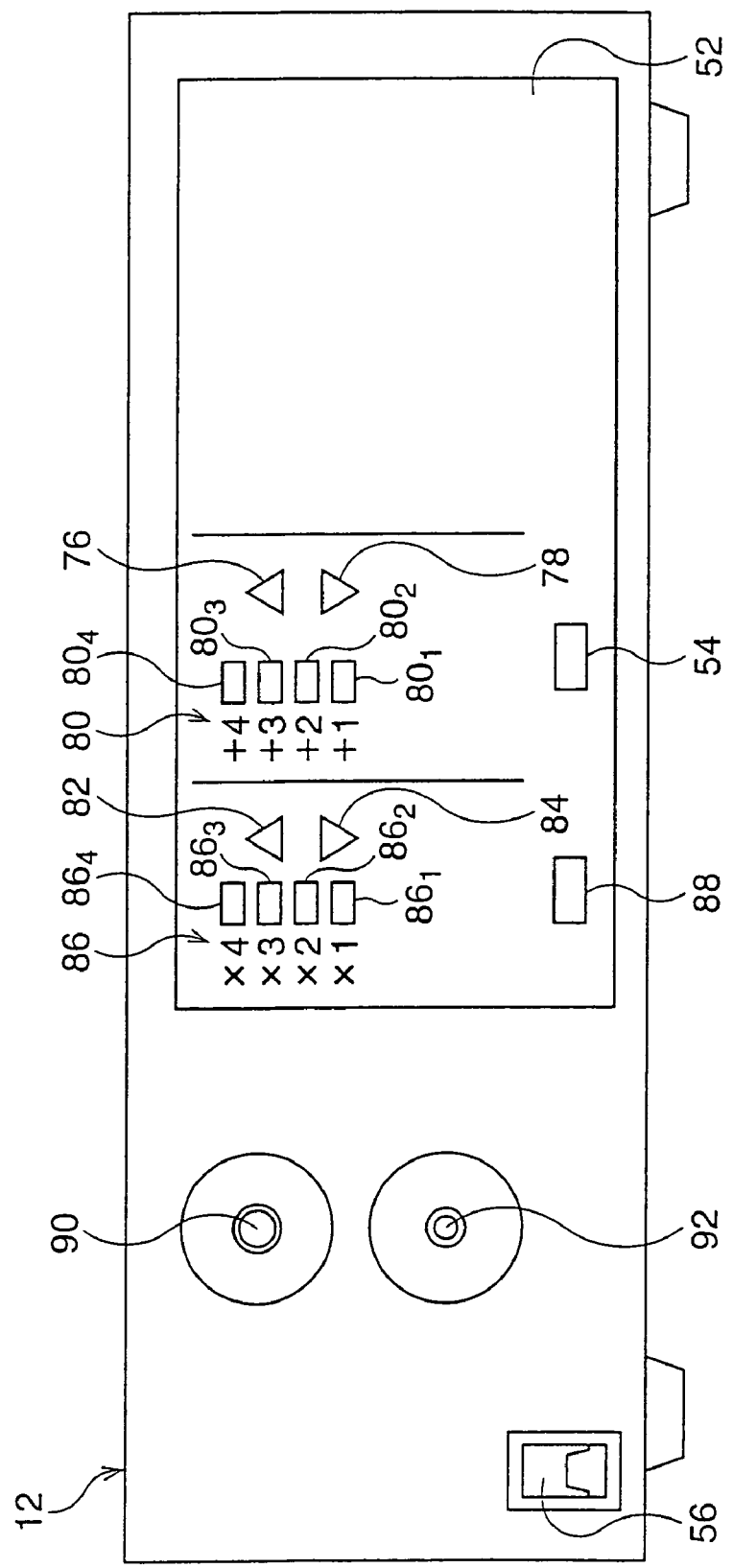
FIG. 9 is a schematic block diagram of a color-balance alteration circuit used as a simulated dye-spraying process circuit in the second embodiment of the electronic endoscope system.

The first, second, and third color-balance alteration circuits 76R, 76G, and 76B are substantially identical to each other. Referring to FIG. 9, the first color-balance alteration circuit 76R is representatively illustrated as a block diagram. As is apparent from this drawing, each of the color-balance alteration circuits 76R, 76G, and 76B is substantially identical to the color-balance alteration circuit 44, used in the first embodiment, except that a multiplier 78 is substituted for both the multiplier circuit 68 and the selector circuit 70 shown in FIG. 3. In both the first and second color-balance alteration circuits 76R and 76G, a density factor "df1" is set in the multiplier 78. In the color-balance alteration circuit 76B, a density factor "df2" is set in the multiplier 78. Note, in FIG. 8, the features similar to those of FIG. 3 are indicated by the same references.

When a simulated dye-spraying (SDS) display mode is selected, a setting of a plus value, for example, "20" is given to the density factor "df1" in the multiplier 78 of both the first and second color-balance alteration circuits 76R and 76G, and a setting of a minus value, for example, "–20" is given to the density factor "df2" in the multiplier 78 of the third color-balance alteration circuit 76B. Thus, during the selection of the SDS mode, the respective frames of color (red, green, and blue) digital image-pixel signals are subjected to color-balance alteration processes in the first, second, and third color-balance alteration circuits 76R, 76G, and 76B, in substantially the same manner as in the color-balance alteration circuit 44. On the other hand, when a usual display mode is selected, a setting of "0" is given to the density factors "df1" and "df2", and thus the respective frames of red, green and blue digital image-pixel signals can pass through the first, second, and third color-balance alteration circuits 76R, 76G, and 76B without being subjected to any color-balance alteration processes.

When the RGB field sequential-type color imaging method is introduced into the electronic endoscope system (FIG. 1), a frame of red image-pixel signals, a frame of green image-pixel signals, and a frame of blue image-pixel signals are sequentially and cyclically produced in accordance with the rotation of the rotary color-filter 30. Thus, it is possible to sequentially and cyclically process the frames of red, green, and blue image-pixel signals in the single color-balance alteration circuit 44. However, when the on-chip color filter method is introduced into the electronic endoscope system (FIG. 8), the frames of color (red, green, and blue) digital image-pixel signals are simultaneously produced in the RGB-converting circuit 74. Accordingly, it is necessary to provide the first, second, and third color-balance alteration circuits 76R, 76G, and 76B, before the frames of color (red, green, and blue) image-pixel signals can be simultaneously processed.

The processed red, green and blue digital image-pixel signals are simultaneously converted into red, green, and blue analog signals by the D/A converting circuit 48, and the red, green, and blue analog image signals are output to the video process circuit 50. On the other hand, the timing controller 34 produces a composite synchronizing signal, and the composite synchronizing signal is output from the timing controller 34 to the video process circuit 50. Thus, similar to the first embodiment, the video process circuit 50 produces a component type video signal based on the red, green, and blue analog image signals output from the D/A converting circuit 48, and the synchronizing signal output from the timing controller 34. Accordingly, during the selection of the usual display mode, an endoscope image, sensed by the CCD image sensor 18, is reproduced as a full color motion picture on the TV monitor 14 with a given proper color balance in accordance with the component type video signal. On the other hand, during the selection of the SDS display mode, the endoscope image is observed on the TV monitor 14 as if the object, sensed by the CCD image sensor 18, were sprayed with a blue-solution.

Note, in the second embodiment, a display-mode-selection-monitoring routine is executed in the system control circuit 32 for giving a setting of "0" to the density factors "df1" and "df2" during the selection of the usual display mode. In this case, of course, the density factor "df1" is set in the first and second color-balance alteration circuits 76R and 76G, and the density factor "df2" is set in the third color-balance alteration circuit 76B.

Third Embodiment

Figure 10:
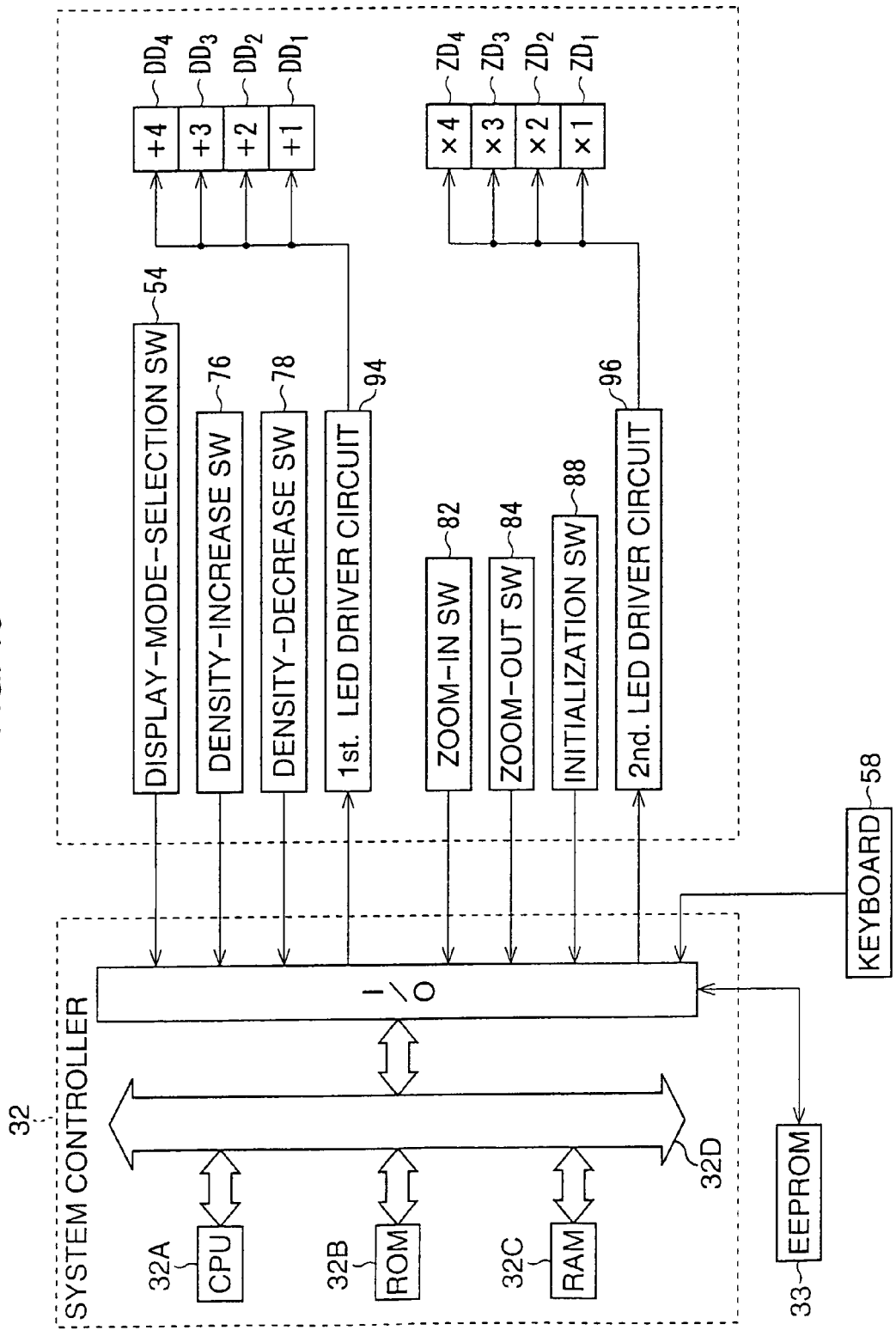
FIG. 10 is a schematic block diagram of a third embodiment of an electronic endoscope system according to the present invention.

Referring to FIG. 10, a third embodiment of an electronic endoscope system according to the present invention is shown as a block diagram. As is apparent from this drawing, the third embodiment is generally identical to the first embodiment shown in FIG. 1. In FIG. 10, the features similar to those of FIG. 1 are indicated by the same references. According to the third embodiment, the electronic endoscope system is constituted such that a simulated-dye-sprayed endoscope image is displayed together with a usual full color endoscope image on a TV monitor 14 while selecting a simulated dye-spraying (SDS) display mode, but only the usual full color endoscope image is displayed on the TV monitor 14 while selecting the usual display mode, similar to the first embodiment.

As shown in FIG. 10, in the third embodiment, a frame memory circuit 46 is substituted for the R-signal, G-signal, and B-signal frame memory 46R, 46G, and 46B, and includes a first R-signal frame memory 46R$_1$, a first G-signal frame memory 46G$_1$, a first B-signal frame memory 46B$_1$, a second R-signal frame memory 46R$_2$, a second G-signal frame memory 46G$_2$, and a second B-signal frame memory 46B$_2$. As is apparent from FIG. 10, the first R-signal, G-signal, and B-signal frame memories 46R$_1$, 46G$_1$, and 46B$_1$, and the second B-20 signal frame memory 46B$_2$ are directly connected to an output terminal of a frame memory 40. Also, the second R-signal and B-signal frame memories 46R$_2$ and 46G$_2$ are connected to the output terminal of the frame memory 40 through the intermediary of a switching-circuit 42' and a simulated dye-spraying process circuit or color-balance alteration circuit 44.

Figure 11:
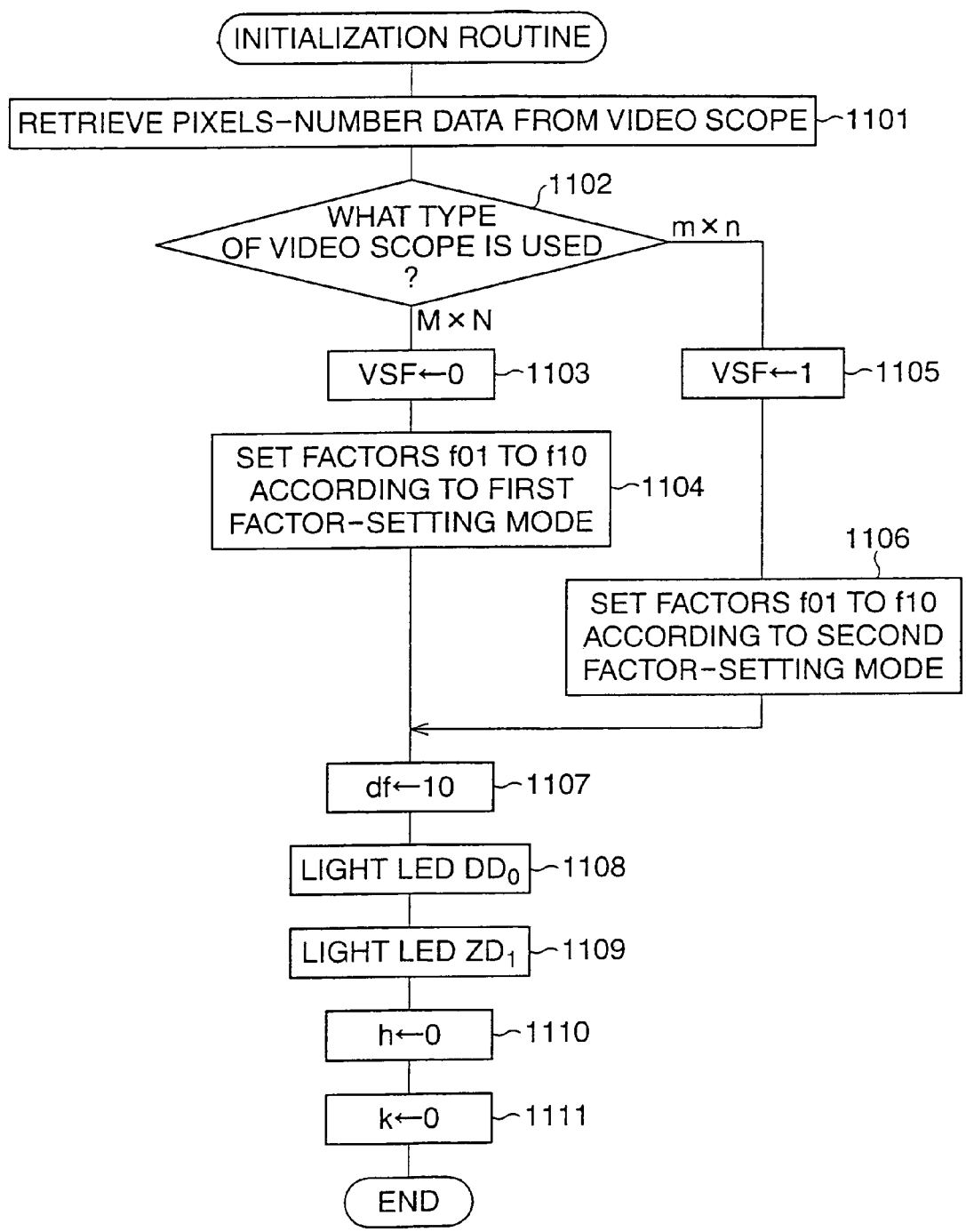
FIG. 11 is a schematic block diagram of a color-balance alteration circuit used as a simulated dye-spraying process circuit in the third embodiment of the electronic endoscope system.

Referring to FIG. 11, the color-balance alteration circuit 44, used in the third embodiment, is shown as a block diagram. As is apparent from the comparison of FIG. 11 with FIG. 3, the color-balance alteration circuit 44, used in the third embodiment, is arranged in substantially the same manner as that of the first embodiment, except that a multiplier 80 is substituted for both the multiplier circuit 68 and the selector circuit 70 shown in FIG. 3. In the third embodiment, a density factor "df" is set in the multiplier 80, and a setting of a suitable plus value, for example, "20" is given to the density factor "df". Similar to the first embodiment, the density factor "df" is variable by operating a keyboard 58. Namely, the density factor "df" is input to a system control circuit 32 by operating the keyboard 58, and then the input density factor "df" is set in the multiplier 80 by the system control circuit 32.

Figure 12:
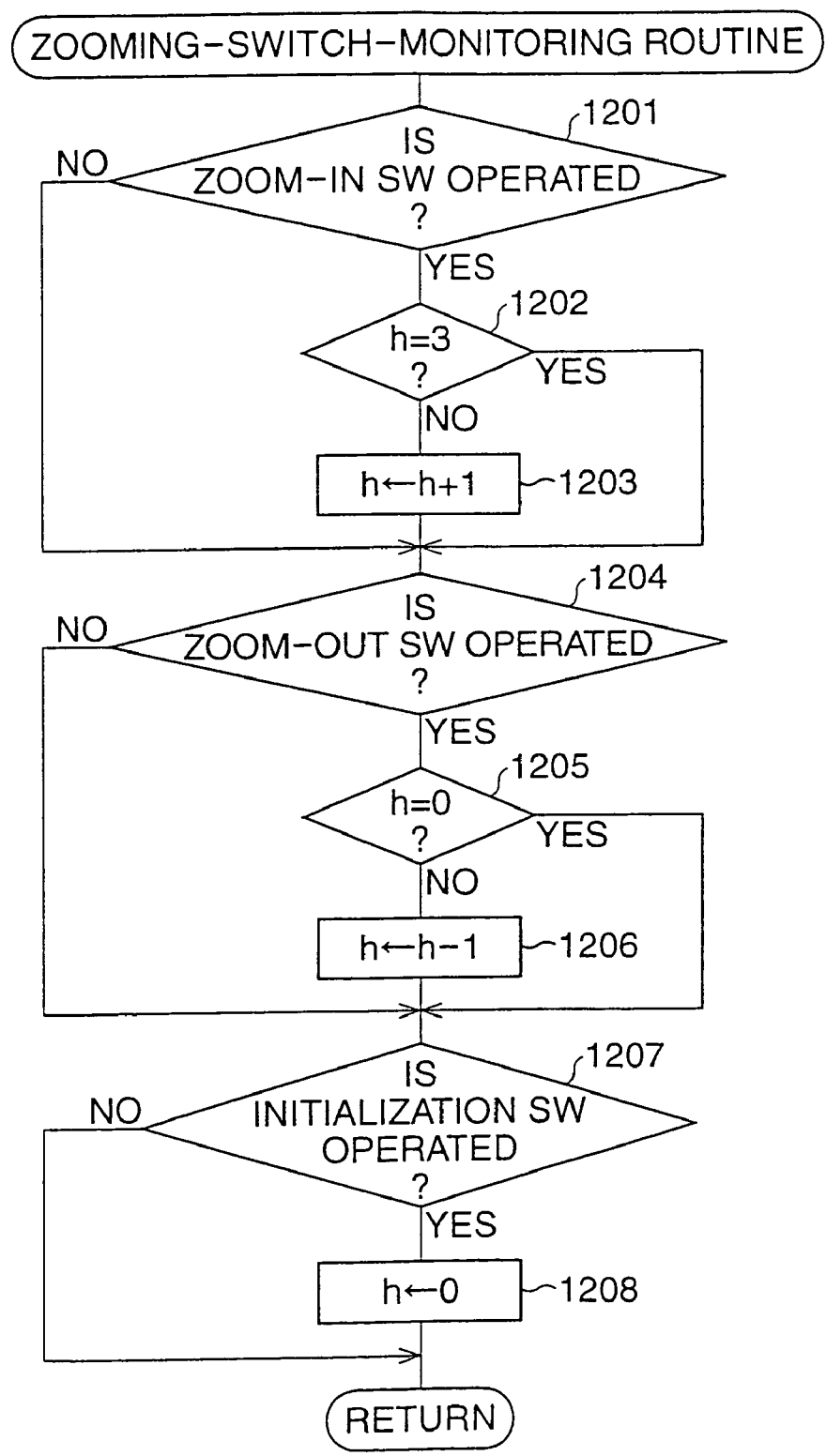
FIG. 12 is a timing chart for explaining an operation of the color-balance alteration circuit shown in FIG. 11.

Similar to the first embodiment, three frames of color (red, green, and blue) digital image-pixel-signals are cyclically and sequentially read from the frame memory 40, as indicated by item (a) in a timing chart of FIG. 12. In the third embodiment, regardless of the selection of either the usual display mode or the SDS display mode, the frame of red digital image-pixel signals is cyclically and sequentially written and stored in the first R-signal frame memory 46R$_1$, as indicated by item (b) in the timing chart of FIG. 12; the frame of green digital image-pixel signals is cyclically and sequentially written and stored in the first G-signal frame memory 46G$_1$, as indicated by item (c) in the timing chart of FIG. 12; and the frame of blue digital image-pixel signals is cyclically and sequentially written and stored in both the first B-signal frame memory 46B$_1$ and the second B-signal frame memory 46B$_2$, as indicated by items (d) and (h) in the timing chart of FIG. 12.

On the other hand, during the selection of the SDS display mode, the switching-circuit 42' is cyclically turned ON such that only the frame of red digital image-pixel signals and the frame of green digital image-pixel signals are fed from the frame memory 40 to the color-balance alteration circuit 44. Namely, in the third embodiment, only the frame of red digital image-pixel signals and the frame of green digital image-pixel signals are subjected to the color-balance alteration process. Note, during the selection of the usual display mode, the switching-circuit 42' is maintained at an OFF-state.

As stated above, since the setting of a plus value, for example, "20" is given to the density factor "df", when each of differences $\Delta R_{ij}$ and $\Delta G_{ij}$ is minus, i.e. when a corresponding color image-pixel signal ($R_{ij}$, $G_{ij}$) is derived from a fine recess area X (FIG. 10), the corresponding value of the image-pixel signal ($R_{ij}$, $G_{ij}$) is decreased in proportion to the magnitude of the absolute value of the signal (df*$\Delta R_{ij}$, df*$\Delta G_{ij}$), similar to the first embodiment. Namely, the frame of red digital image-pixel signals ($R_{ij}$) is processed by the color-balance alteration circuit 44, and the frame of processed red digital image-pixel signals ($R_{ij}$) is then written and stored in the second R-signal frame memory 46R$_2$, as indicated by item (f) in the timing chart of FIG. 12. Also, the frame of green digital image-pixel signals ($G_{ij}$) is processed by the color-balance alteration circuit 44, and the frame of processed green digital image-pixel signals ($G_{ij}'$) is then written and stored in the second G-signal frame memory 46G$_2$, as indicated by item (g) in the timing chart of FIG. 12.

Note, in items (f) and (g) of the timing chart of FIG. 12, a short time interval "t" corresponds to the time necessary to process the frame of digital image-pixel signals ($R_{ij}$, $G_{ij}$) in the color-balance alteration circuit 44. Namely, the writing of the processed red digital image-pixel signals ($R_{ij}'$) in the second R-signal frame memory 46R$_2$ is delayed for the short time interval "It" in comparison with the writing of the red digital image-pixel signals ($R_{ij}$) in the first R-signal frame memory 46R$_1$, and the writing of the processed green digital image-pixel signals ($G_{ij}'$) in the second G-signal frame memory 46G$_2$ is delayed for the short time interval "t" in comparison with the writing of the green digital image-pixel signals ($G_{ij}$) in the first G-signal frame memory 46G$_1$.

While the usual display mode is selected, only the red, green, and blue digital image-pixel signals ($R_{ij}$, $G_{ij}$, and $B_{ij}$) are simultaneously read from the first R-signal, G-signal, and B-signal frame memories 46R$_1$, 46G$_1$, and 46B$_1$, as indicated by item (e) in the timing chart of FIG. 12, and are output to a digital-to-analog (D/A) converting circuit 48 including three digital-to-analog (D/A) converters. Then, the read red, green, and blue digital image-pixel signals ($R_{ij}$, $G_{ij}$, and $B_{ij}$) are respectively converted into red, green, and blue analog image signals by the three D/A converters of the D/A converting circuit 48.

The red, green, and blue analog image signals are output from the D/A converting circuit 48 to a video process circuit 50. On the other hand, a timing controller 34 produces a composite synchronizing signal, and the composite synchronizing signal is output from the timing controller 34 to the video process circuit 50. The video process circuit 50 produces a first type of video signal $VS_1$, as indicated by item (a) in a timing chart of FIG. 13, based on the red, green, and blue analog image signals output from the D/A converting circuit 48, and the synchronizing signal component output from the timing controller 34.

Note, similar to the first embodiment, in the video process circuit 50, the first type of video signal $VS_1$ is subjected to various image-processings, such as profile-enhancing, noise-elimination, and so on.

Figure 14:
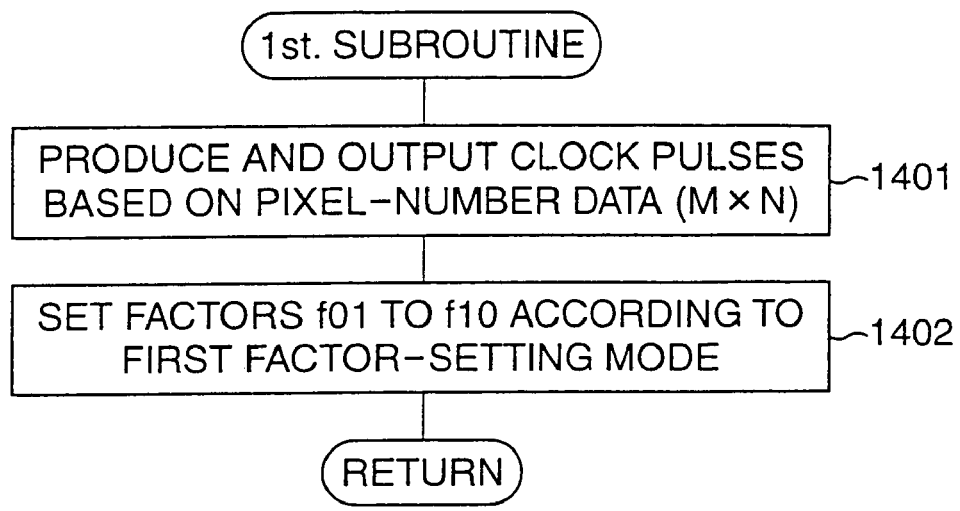
FIG. 14 is a conceptual view showing, by way of example, a usual full color endoscope image displayed on a screen of a TV monitor in accordance with the first type of video signal in the third embodiment.

The first type of video signal $VS_1$ is fed from the video process circuit 50 to the TV video monitor 14. Thus, a usual full color endoscope image is reproduced on the TV monitor 14 based on the first type of video signal $VS_1$. As shown in FIG. 14 by way of example, the usual full color endoscope image is displayed on a partial display area $DA_1$ on the screen of the TV monitor 14. This is because the CCD image sensor 18, used in a video scope 10, has a smaller size than that of a CCD image sensor used in a usual TV camera. Namely, the number of image pixels, included in one frame, obtained from the CCD image sensor 18, is less than the number of image pixels, included in one frame, obtained from the CCD image sensor used in a usual TV camera.

Figure 13:
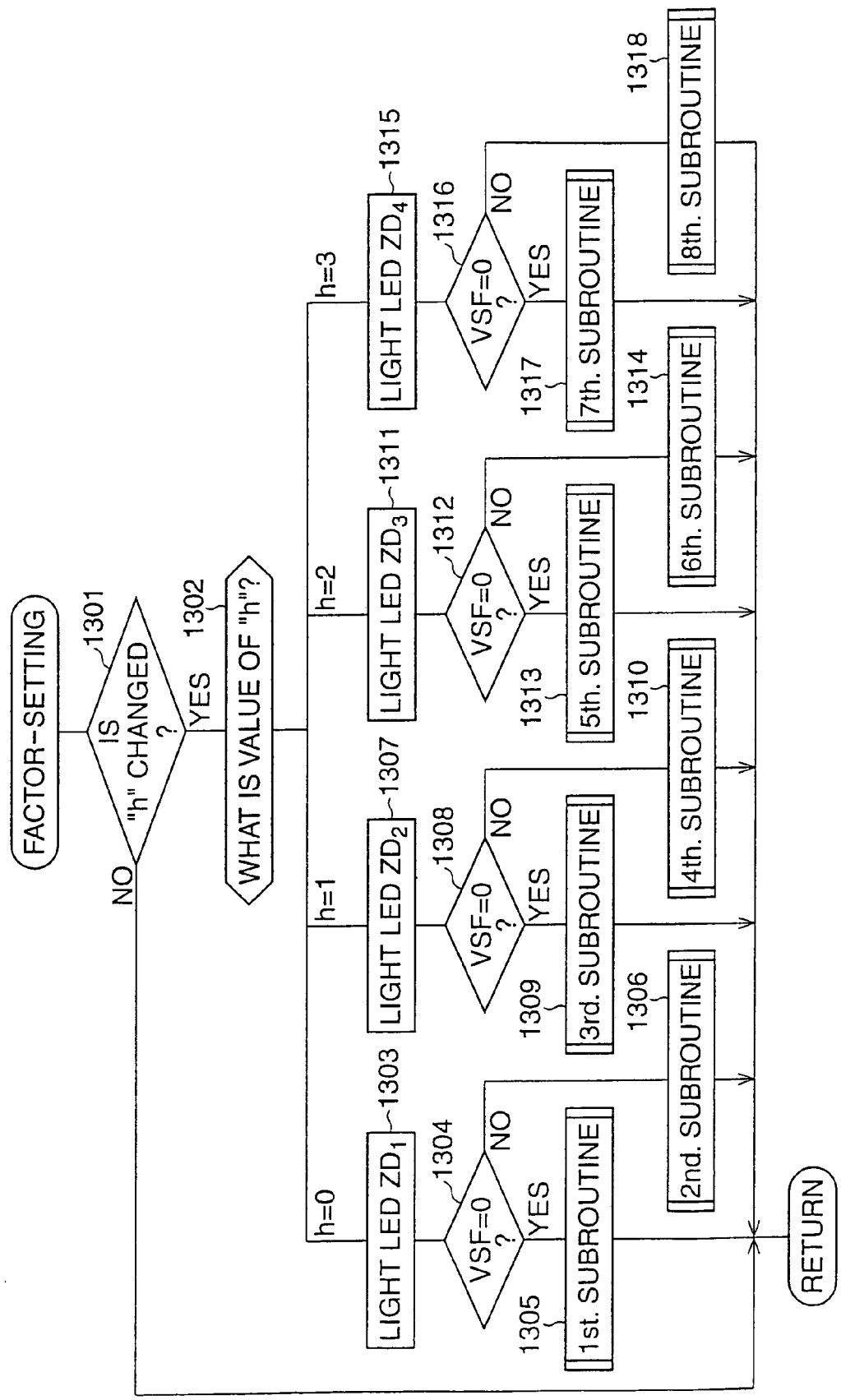
FIG. 13 is a timing chart for explaining a production of a first type of video signal and a second type of video signal in a video process circuit shown in FIG. 10.

Nevertheless, in the electronic endoscope system, the TV monitor 14 having a usual standard size is used, and the first type of video signal $VS_1$ is produced and prepared with respect to the overall area of the screen of the TV monitor 14, so as to exhibit a pedestal level over the remaining display area of the screen except for the display area $DA_1$ on which the endoscope image is reproduced and displayed, as indicated by item (a) in the timing chart of FIG. 13. In particular, as is apparent from item (a) of FIG. 13 and FIG. 14, in a single-scanning line of the first type of video signal $VS_1$, which traverses the partial display area $DA_1$, an image-signal extent IE ($R_{ij}+G_{ij}+B_{ij}$) lies between a first pedestal level extent $PE_1$ and a second pedestal level extent $PE_2$.

While the SDS display mode is selected, not only are the red, green, and blue digital image-pixel signals ($R_{ij}$, $G_{ij}$, and $B_{ij}$) simultaneously read from the first R-signal, G-signal, and B-signal frame memories $46R_1$, $46G_1$, and $46B_1$, but also the processed red and green digital image-pixel signals ($R_{ij}'$ and $G_{ij}'$) and the blue digital image-pixel signals ($B_{ij}$) are simultaneously read from the second R-signal, G-signal, and B-signal frame memories $46R_2$, $46G_2$, and $46B_2$, as indicated by items (e) and (i) in the timing chart of FIG. 12.

In particular, the red image-pixel signals ($R_{ij}$) and the processed red image-pixel signals ($R_{ij}'$) are alternately read from the first R-signal frame memory $46R_1$ and the second R-signal frame memory $46R_2$; the green image-pixel signals ($G_{ij}$) and the processed green image-pixel signals ($G_{ij}'$) are alternately read from the first G-signal frame memory $46G_1$ and the second G-signal frame memory $46G_2$; and both the blue image-pixel signals ($B_{ij}$) are alternately read from the first B-signal frame memory $46B_1$ and the second B-signal frame memory $46B_2$. The read red digital image-pixel signals ($R_{ij}$ and $R_{ij}'$), the read green digital image-pixel signals ($G_{ij}$ and $G_{ij}'$), and both the read blue digital image-pixel signals ($B_{ij}$ and $B_{ij}$) are output to the D/A converting circuit 48. Then, the read red digital image-pixel signals ($R_{ij}$ and $R_{ij}'$), the read green digital image-pixel signals ($G_{ij}$ and $G_{ij}'$), and both the read blue digital image-pixel signals ($B_{ij}$ and $B_{ij}$) are respectively converted into red, green, and blue analog image signals by the three D/A converters of the D/A converting circuit 48.

The red, green, and blue analog image signals are output from the D/A converting circuit 48 to the video process circuit 50, and the composite synchronizing signal is also output from the timing controller 34 to the video process circuit 50. The video process circuit 50 produces a second type of video signal $VS_2$, as indicated by item (b) in the timing chart of FIG. 13, based on the red, green, and blue analog image signals output from the D/A converting circuit 48, and the synchronizing signal component output from the timing controller 34.

Figure 15:
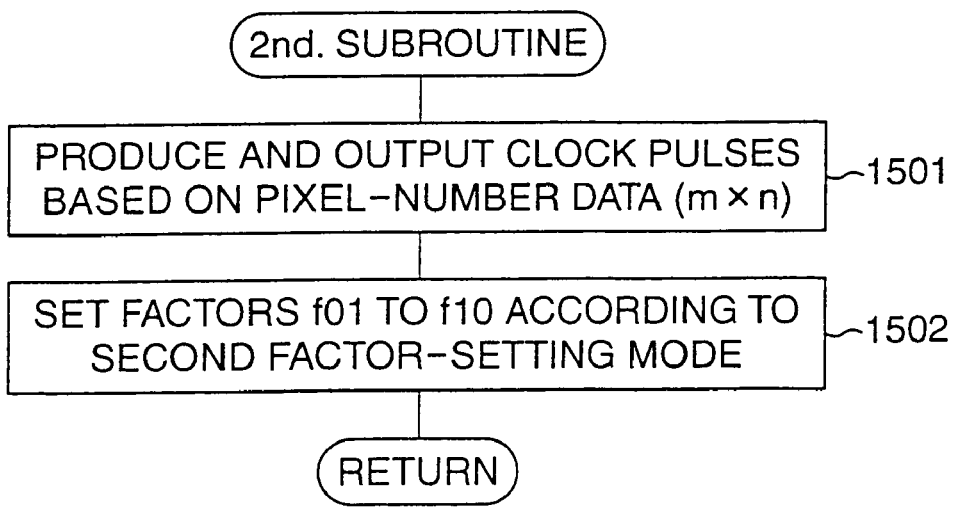
FIG. 15 is a conceptual view showing, by way of example, a usual full color endoscope image and a simulated-dye-sprayed endoscope image displayed on the screen of the TV monitor in accordance with the first and second types of video signals in the third embodiment.

The second type of video signal $VS_2$ is fed from the video process circuit 50 to the TV video monitor 14. Thus, both a usual full color endoscope image and a simulated-dye-sprayed endoscope image are reproduced on the TV monitor 14 based on the second type of video signal $VS_2$. As shown in FIG. 15 by way of example, the usual full color endoscope image is displayed on the aforesaid partial display area $DA_1$ on the screen of the TV monitor 14, and the simulated-dye-sprayed endoscope image is display on another partial display area $DA_2$ adjacent to the partial display area $DA_1$. As is apparent from item (b) of FIG. 13 and FIG. 15, in a single-scanning line of the second type of video signal $VS_2$, which crosses the partial display areas $DA_1$ and $DA_2$, both an image-signal extents $IE_1$ ($R_{ij}+G_{ij}+B_{ij}$) and an image-signal extents $IE_2$ ($R_{ij}'+G_{ij}'+B_{ij}$) lie between a first pedestal level extent $PE_1$ and a second pedestal level extent $PE_2$.

Thus, according to the third embodiment, it is possible to simultaneously observe both the usual full color endoscope image and the simulated-dye-sprayed endoscope image on the TV monitor 14, if necessary.

Figure 16:
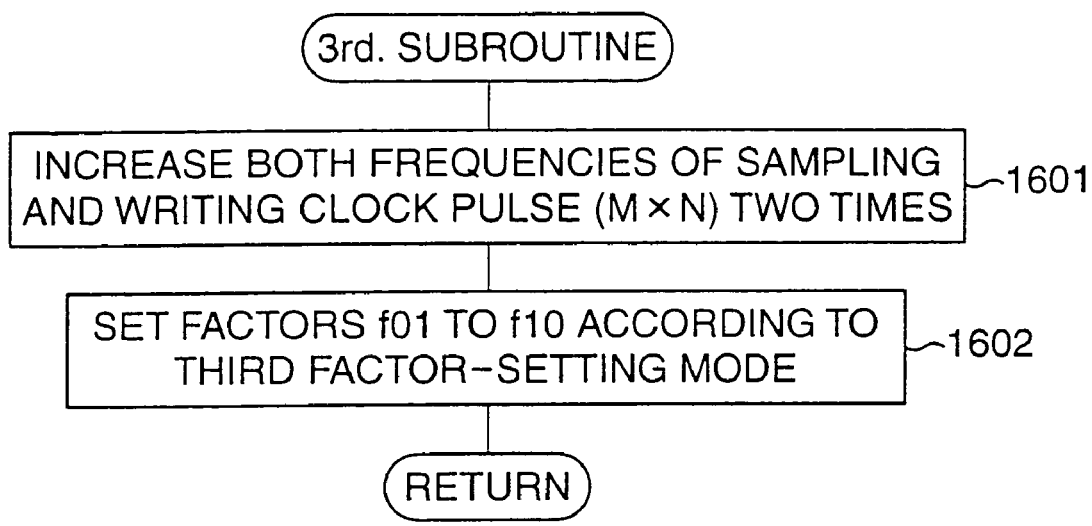
FIG. 16 is a flowchart of a display-mode-selection-monitoring routine executed in a system control circuit included in the third embodiment of the electronic endoscope system.

FIG. 16 shows a flowchart of a display-mode-selection-monitoring routine, which is executed in the system control circuit 32, used in the third embodiment (FIG. 10). This routine is also formed as a time-interruption routine executed at regular suitable intervals of, for example, 20 ms. The execution of the routine is started after a power ON/OFF switch 56 is turned ON, and is repeated every 20 ms as long as the power ON/OFF switch 56 is turned ON.

At step 1601, it is monitored whether either the usual display mode or the SDS display mode has been changed to the other display mode by operating either the display mode selection switch 54 or the function key concerned on the keyboard 58. When a change in the display mode is not confirmed, the routine immediately ends. Although the routine is repeatedly executed every 20 ms, there in no progress until a change in the display mode is confirmed.

At step 1601, when it is confirmed that the display mode has been changed, the control proceeds to step 1602, in which it is determined whether the usual display mode has been selected. When the selection of the usual display mode is confirmed, the control proceeds to step 1603, in which only the reading of red, green, and blue digital image-pixel signals ($R_{ij}$, $G_{ij}$, and $B_{ij}$) from the first R-signal, G-signal, and B-signal frame memories $46R_1$, $46G_1$, and $46B_1$ is performed.

At step 1602, when the selection of the usual display mode is not confirmed, i.e. when it is confirmed that the SDS display mode has been selected, the control proceeds from step 1602 to step 1604, in which both the reading of red, green, and blue digital image-pixel signals ($R_{ij}$, $G_{ij}$, and $B_{ij}$) from the first R-signal, G-signal, and B-signal frame memories $46R_1$, $46G_1$, and $46B_1$ and the reading of red, green, and blue digital image-pixel signals ($R_{ij}'$, $G_{ij}'$, and $B_{ij}$) from the second R-signal, G-signal, and B-signal frame memories $46R_2$, $46G_2$, and $46B_2$ is performed, as mentioned above.

Note, whenever the power ON/OFF switch 56 is turned ON, the usual display mode is forcibly selected, and thus only the reading of red, green, and blue digital image-pixel signals ($R_{ij}$, $G_{ij}$, and $B_{ij}$) from the first R-signal, G-signal, and B-signal frame memories $46R_1$, $46G_1$, and $46B_1$ is performed.

Fourth Embodiment

Figure 17:
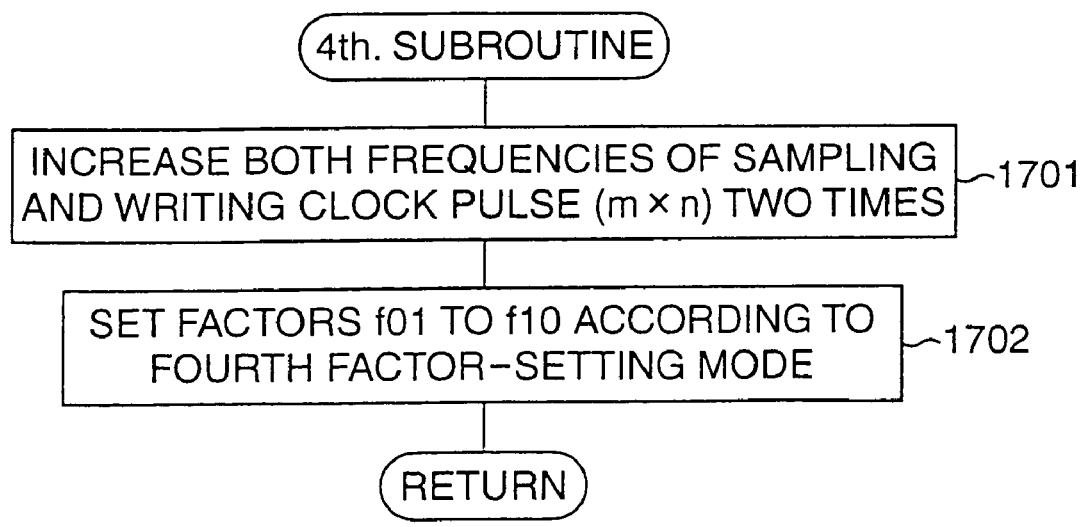
FIG. 17 is a schematic block diagram of a fourth embodiment of an electronic endoscope system according to the present invention.

Referring to FIG. 17, a fourth embodiment of an electronic endoscope system according to the present invention is shown as a block diagram. In this drawing, the features similar to those of FIGS. 1, 8, and 10 are indicated by the same references.

In the fourth embodiment, similar to the second embodiment, the on-chip color filter method is introduced to reproduce an endoscope image as a full color image on a TV monitor 14, and thus a video scope 10 and an image-signal processing unit 12 are modified so as to conform to the on-chip color filter method, as explained with reference to FIG. 8.

According to the fourth embodiment, in an image-signal processor, provided in the image-signal processing unit 12, an RGB-converting circuit 74, a first color-balance alteration circuit 44R, a second color-balance alteration circuit 44G, and a frame memory circuit 46 are arranged, as shown in FIG. 17. Each of the first and second color-balance alteration circuits 44R and 76G is substantially identical to the color-balance alteration circuit 44 (FIG. 11) used in the third embodiment. The frame memory circuit 46 includes first and second R-signal frame memories $46R_1$ and $46R_2$, first and second G-signal frame memories $46G_1$ and $46G_2$, and first and second B-signal frame memories $46B_1$ and $46B_2$, which are arranged, as shown in FIG. 17.

Similar to the second embodiment, the RGB-converting circuit 74 simultaneously outputs a red digital image-pixel signal $R_{ij}$), a green digital image-pixel signal ($G_{ij}$) and a blue digital image-pixel signal ($B_{ij}$). The output red digital image-pixel signals ($R_{ij}$) are input to both the first R-signal frame memory $46R_1$ and the first color-balance alteration circuit 44R; the output green digital image-pixel signals ($G_{ij}$) are input to both the first G-signal frame memory $46G_1$ and the second color-balance alteration circuit 44G; and the output blue digital image-pixel signals ($B_{ij}$) are input to both the first and second B-signal frame memories $46B_1$, and $46B_2$.

In particular, the red image-pixel signal ($R_{ij}$) is directly written and stored in the first R-signal frame memory $46R_1$. Also, the red image-pixel signal ($R_{ij}$), input to the first color-balance alteration circuit 44R, is processed in substantially the same manner as explained with reference to FIG. 11, and then the processed red image-pixel signal ($R_{ij}'$) is written and stored in the second R-signal frame memory $46R_2$. Similarly, the green image-pixel signal ($G_{ij}$) is directly written and stored in the first G-signal frame memory $46G_1$. The green image-pixel signal ($G_{ij}$), input to the second color-balance alteration circuit 44G, is processed in substantially the same manner as explained with reference to FIG. 11, and then the processed green image-pixel signal ($G_{ij}'$) is written and stored in the second G-signal frame memory $46G_2$. Also, the blue image-pixel signal ($B_{ij}$) is directly written and stored in the first and second B-signal frame memories $46B_1$ and $46B_2$.

Figure 18:
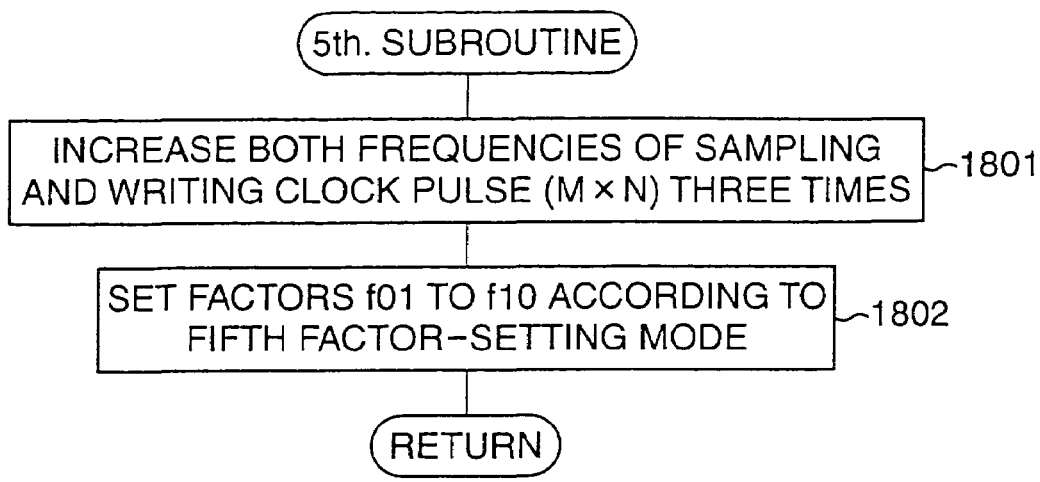
FIG. 18 is a timing chart for explaining an operation of a color-balance alteration circuit shown in FIG. 17.

In short, the frames of red, green, and blue digital image pixel signals ($R_{ij}$, $G_{ij}$ and $B_{ij}$) are respectively stored in the first R-signal, G-signal, and B-signal frame memories $46R_1$, $46G_1$ and $46B_1$, as indicated by item (a) in a timing chart of FIG. 18. Also, the frames of processed red and green digital image-pixel signals ($R_{ij}'$ and $G_{ij}'$) and the frame of blue digital image pixel signals ($B_{ij}$) are respectively stored in the second R-signal, G-signal, and B-signal frame memories $46R_2$, $46G_2$ and $46B_2$, as indicated by item (c) in the timing chart of FIG. 18.

Note, in item (c) of the timing chart of FIG. 18, the short time interval "t" corresponds to the time necessary to process the frame of digital image-pixel signals ($R_{ij}$, $G_{ij}$) in the color-balance alteration circuit 44.

Similar to the third embodiment, while a usual display mode is selected, only the red, green, and blue digital image-pixel signals ($R_{ij}$, $G_{ij}$, and $B_{ij}$) are simultaneously read from the first R-signal, G-signal, and B-signal frame memories $46R_1$, $46G_1$, and $46B_1$, as indicated by item (b) in the timing chart of FIG. 18, and are output to a digital-to-analog (D/A) converting circuit 48. Then, the read red, green, and blue digital image-pixel signals ($R_{ij}$, $G_{ij}$, and $B_{ij}$) are respectively converted into red, green, and blue analog image signals by the D/A converting circuit 48.

The red, green, and blue analog image signals are output from the D/A converting circuit 48 to a video process circuit 50. On the other hand, a timing controller 34 produces a composite synchronizing signal, and the composite synchronizing signal is output from the timing controller 34 to the video process circuit 50. Thus, similar to the aforesaid third embodiment, the video process circuit 50 produces a first type of video signal ($VS_1$), as indicated by item (a) in the timing chart of FIG. 13, based on the red, green, and blue analog image signals output from the D/A converting circuit 48, and a synchronizing signal component output from a timing controller 34, whereby a usual full color endoscope image is displayed on a TV monitor in accordance with the first type of video signal ($VS_1$), as shown in FIG. 14.

On the other hand, while a simulated dye-spraying display (SDS) mode is selected, the red image-pixel signals ($R_{ij}$) and the processed red image-pixel signals ($R_{ij}'$) are alternately read from the first R-signal frame memory $46R_1$ and the second R-signal frame memory $46R_2$; the green image-pixel signals ($G_{ij}$) and the processed red image-pixel signals ($G_{ij}'$) are alternately read from the first G-signal frame memory $46G_1$ and the second G-signal frame memory $46G_2$; and the blue image-pixel signals ($B_{ij}$) are alternately read from the first B-signal frame memory $46B_1$ and the second B-signal frame memory $46B_2$, as indicated by items (b) and (d) in the timing chart of FIG. 18.

The read red digital image-pixel signals ($R_{ij}$ and $R_{ij}'$), the read green digital image-pixel signals ($G_{ij}$ and $G_{ij}'$) and both the read blue digital image-pixel signals ($B_{ij}$ and $B_{ij}$) are respectively converted into red, green, and blue analog image signals by the D/A converting circuit 48. Then, the red, green, and blue analog image signals are output from the D/A converting circuit 48 to the video process circuit 50. Thus, similar to the aforesaid third embodiment, the video process circuit 50 produces a second type of video signal ($VS_2$), as indicated by item (b) in the timing chart of FIG. 13, based on the red, green, and blue analog image signals output from the D/A converting circuit 48, and the synchronizing signal component output from the timing controller 34, whereby a simulated-dye-sprayed endoscope image is displayed together with a usual full color endoscope image on the TV monitor in accordance with the second type of video signal ($VS_2$), as shown in FIG. 15.

Thus, similar to the third embodiment, in the fourth embodiment, it is possible to simultaneously observe both the usual full color endoscope image and the simulated-dye-sprayed endoscope image on the TV monitor 14, if necessary.

Also, in the fourth embodiment, by using the flowchart of display-mode-selection-monitoring routine, as shown in FIG. 16, it is possible to select either the reading of the red, green, and blue digital image-pixel signals ($R_{ij}$, $G_{ij}$, and $B_{ij}$) from the first frame memories $46R_1$, $46G_1$, and $46B_1$ or the alternate reading of the red, green, and blue digital image-pixel signals ($R_{ij}$ and $R_{ij}'$; $G_{ij}$ and $G_{ij}'$; and $B_{ij}$ and $B_{ij}$) from the first and second frame memories $46R_1$, $46G_1$, and $46B_1$; and $46R_2$, $46G_2$, and $46B_2$ in accordance with the selection of either the usual display mode or the SDS display mode.

Fifth Embodiment

Figure 19:
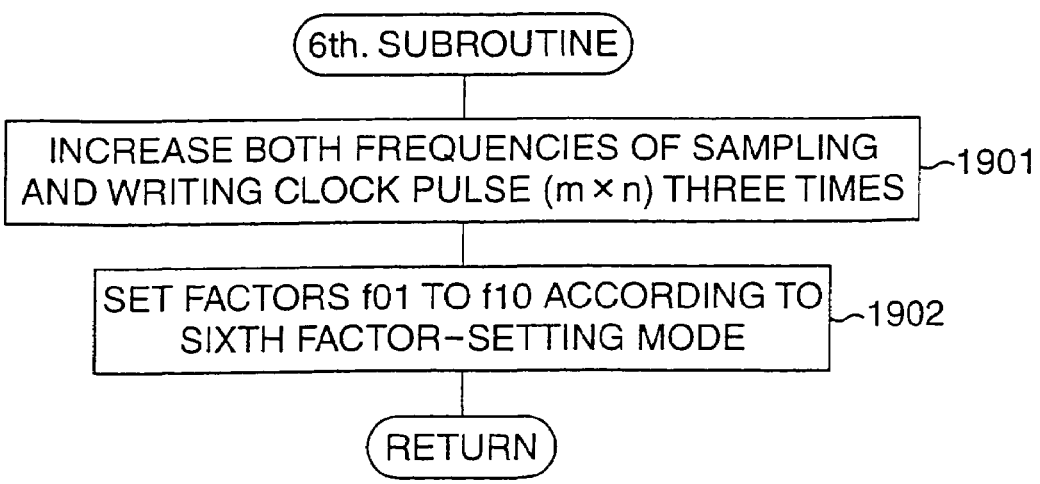
FIG. 19 is a schematic block diagram of a fifth embodiment of an electronic endoscope system according to the present invention.

Referring to FIG. 19, a fifth embodiment of an electronic endoscope system according to the present invention is shown as a block diagram. In this drawing, the features similar to those of FIG. 1 are indicated by the same references.

In the fifth embodiment, the electronic endoscope system includes a video scope 10, an image-signal processing unit 12, a color-balance alteration process unit or simulated dye-spraying process unit 82, a first TV monitor 84, and a second monitor 86. In this system, since the RGB field sequential-type color imaging method is used, the video scope 10 is constituted in substantially the same manner as in the first embodiment, and a light source device (24, 26, 28, and 30), provided in the image-signal processing unit 12, is also constituted in substantially the same manner as in the first embodiment.

The image-signal processing unit 12 is provided with a system controller 88, and an image-signal processor 90. The system controller 88 includes a system control circuit and a timing controller, as indicated by references 32 and 34 in FIG. 1. The image-signal processor 90 is arranged in substantially the same manner as in the first embodiment, except that the switching-circuit 42 and the color-balance alteration circuit 44 are eliminated therefrom. In short, the image-signal processor 90 is constituted so as to produce a component type video signal, composed of a red video signal component (R), a green video signal component (G), a blue video signal component (B), and a composite synchronizing signal component (S), based on frames of red, green, and blue analog image signals obtained from the video scope 10.

As shown in FIG. 19, the simulated dye-spraying process unit 82 includes a system control circuit 92 and a timing controller 94, and a color-balance alteration processor, generally indicated by reference 95.

The system control circuit 92 contains a microcomputer comprising a central processing unit (CPU), a read-only memory (ROM) for storing programs and constants, a random-access memory (RAM) for storing temporary data, and an input/output interface circuit (I/O). The timing controller 94 produces and outputs various series of clock pulses having given frequencies, under the control of the system control circuit 92, to thereby operate sequentially and systematically various electronic elements included in the color-balance alteration processor 95, as stated hereinafter.

The color-balance alteration processor 95 includes three analog-to-digital (A/D) converters 96R, 96G, and 96B, three frame memories 98R, 98G, and 98B, a delay circuit 100, a first color-balance alteration circuit 102R, a second color-balance alteration circuit 102G, two frame memories 104R and 104G, three digital-to-analog (D/A) converters 106R, 106G, and 106B, and a video process circuit 108. Note, in FIG. 9, although connecting lines are not shown, in order to avoid an overly complex illustration, the various electronic elements are connected to the timing controller 94.

As shown in FIG. 19, the component type video signal (R, G, B, and S) is fed from the image-signal processor 90 to the simulated dye-spraying process unit 82, such that the red video signal component (R), the green video signal component (G), the blue video signal component (B), and the composite synchronizing signal component (S) are respectively input to the A/D converters 96R, 96G, and 96B, and the delay circuit 100.

Note, as is apparent from FIG. 19, the component type video signal (R, G, B, and S) is also fed from the image-signal processor 90 to the TV monitor 84 through the intermediary of the simulated dye-spraying process unit 82, and thus an endoscope image is reproduced as a usual full color image on the TV monitor 84 in accordance with the component type video signal (R, G, B, and S)

The A/D converter 96R successively outputs a red digital image-pixel signal in accordance with the inputting of the red video signal component (R), and the red digital image-pixel signal is successively written and stored in the frame memory 98R. Also, the A/D converter 96G successively outputs a green digital image-pixel signal in accordance with the inputting of the green video signal component (G), and the green digital image-pixel signal is successively written and stored in the frame memory 98G. Further, the A/D converter 96B successively outputs a blue digital image-pixel signal in accordance with the inputting of the blue video signal component (B), and the blue digital image-pixel signal is successively written and stored in the frame memory 98B. In each of the frame memories 98R, 98G, and 98B, a frame of digital image-pixel signals ($R_{ij}$, $G_{ij}$, $B_{ij}$) is stored in a m×n matrix manner, as explained with reference to FIG. 2. On the other hand, the delay circuit 100 is provided for outputting the composite synchronizing signal component (S) as a composite synchronizing signal delayed for a predetermined time, as stated in detail hereinafter.

Note, the outputting of the digital image-pixel signals from each A/D converter (96A, 96G, 96B) is performed in accordance with a series of sampling clock pulses output from the timing controller 94, and the writing of the digital image-pixel signals in each frame memory (98A, 98G, 98B) is performed in accordance with a series of writing clock pulses output from the timing controller 94.

Figure 20:
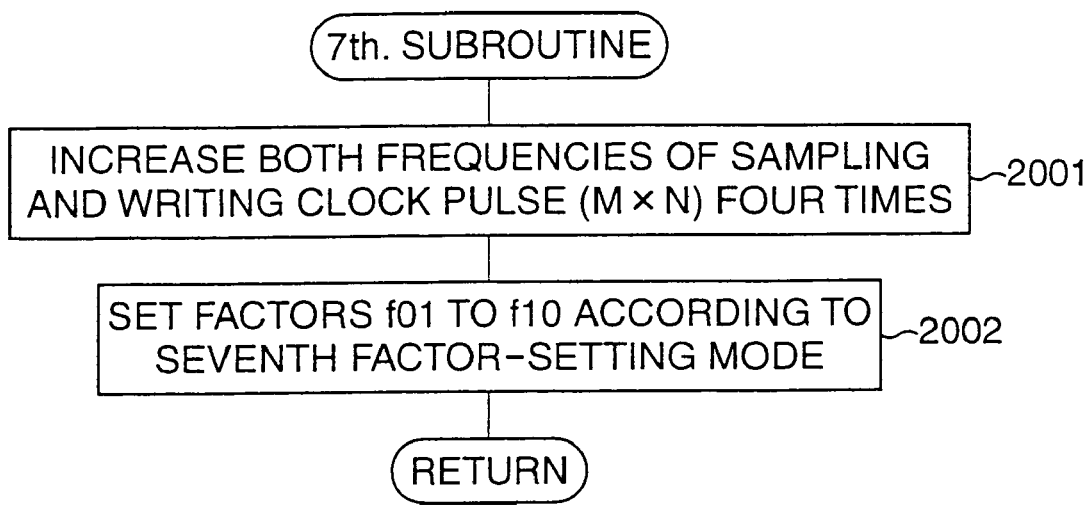
FIG. 20 is a schematic block diagram of a color-balance alteration circuit used as a simulated dye-spraying process circuit in the fifth embodiment of the electronic endoscope system.

The first and second color-balance alteration circuits 102R and 102G are identical to each other, and are operated under the control of the system control circuit 92. Referring to FIG. 20, the color-balance alteration circuit 102R is representatively shown as a block diagram. As is apparent from FIG. 20, the first color-balance alteration circuit 102R is essentially identical to that of FIG. 11. Thus, in FIG. 20, the features similar to those of FIG. 11 are indicated by the same references.

In the simulated dye-spraying process unit 82, either a usual display mode or a simulated dye-spraying (SDS) display mode is manually selected, as stated hereinafter. While the SDS display mode is selected, a setting of a suitable plus value, for example, "20" is given to a density factor "df", which is set in a multiplier 80 of each color-balance alteration circuit (102R, 102G). While the usual display mode is selected, a setting of "0" is forcibly given to the density factor "df".

The red digital image-pixel signals ($R_{ij}$) are read from the frame memory 98R, as explained with respect to FIG. 2, and each of the read digital image-pixel signals ($R_{ij}$) is successively fed to the first color-balance alteration circuit 102R. Thus, during the selection of the SDS display mode, the red digital image-pixel signal ($R_{ij}$) is subjected to a color-balance alteration process, due to the setting of "20" for the density factor "df", as already explained. The processed red digital image-pixel signal ($R_{ij}'$) is successively written and stored in the frame memory 104R. The same is true for the green digital image-pixel signal read from the frame memory 98G, and thus the green digital image pixel signal ($G_{ij}'$), processed by the second color-balance alteration circuit 102G, is successively written and stored in the frame memory 104G.

Note, the reading of the digital image-pixel signals from each frame memory (98R, 98G) is performed in accordance with a series of reading clock pulses output from the timing controller 94, and the writing of the digital image-pixel signals in each frame memory (104R, 104G) is performed in accordance with a series of writing clock pulses output from the timing controller 94.

The processed red digital image-pixel signal ($R_{ij}'$) the processed green digital image-pixel signal ($G_{ij}'$), and the blue digital image-pixel signal ($B_{ij}$) are simultaneously read from the frame memories 104R, 104G, and 98B, respectively. Namely, the reading of the blue digital image-pixel signals ($B_{ij}$) is delayed in comparison with the reading of the red and green digital image-pixel signal from the frame memory 98R and 98G, by a time necessary to process the red and green digital image-signal ($R_{ij}$ and $R_{ij}$) in the first and second color-balance alteration circuits 102R and 102G. The read digital image-pixel signals ($R_{ij}'$, $G_{ij}'$, and $B_{ij}$) are input to the D/A converters 106R, 106G, and 106B, respectively, and thus the red, green, and blue digital image-pixel signals ($R_{ij}'$, $G_{ij}'$, and $B_{ij}$) are respectively converted into red, green, and blue analog image signals by the D/A converters 106R, 106G, and 106B.

Note, the reading of the blue digital image signal ($B_{ij}$) from the frame memory 98B is performed in accordance with a series of reading clock pulses output from the timing controller 94, the reading of the processed red and green image-pixel signals ($R_{ij}'$ and $G_{ij}'$) from the frame memories 104R and 104G is performed in accordance with a series of reading clock pulses output from the timing controller 94, and the conversion of the digital image-pixel signals ($R_{ij}'$, $G_{ij}'$, and $B_{ij}$) into the analog image signals by the D/A converters 106R, 106G, 106B in accordance with a series of sampling clock pulses output from the timing controller 94.

The converted red, green, and blue analog image signals are simultaneously output from the D/A converters 106R, 106G, and 106B to the video process circuit 108. On the other hand, the composite synchronizing signal is further output from the delay circuit 100 to the video process circuit 108 in synchronization with the outputting of the red, green, and blue analog image signals from the D/A converters 106R, 106G, and 106B to the video process circuit 108. Namely, the delay circuit 100 delays the outputting of the composite synchronizing signal by a time necessary to process the red and green digital image-signals ($R_{ij}$ and $G_{ij}$) in the first and second color-balance alteration circuits 102R and 102G, the frame memories 104R and 104G, and the D/A converters 106R and 106G.

The video process circuit 108 produces a component type video signal based on the red, green, and blue analog image signals output from the D/A converters 106R, 106G, and 106B, and the composite synchronizing signal output from the delay circuit 100. In the fifth embodiment, the video process circuit 108 includes a color encoder for producing various video signals, such as, an S-video signal, a composite type video signal, and so on, based on the component type video signal. For example, the composite type video signal is from the video process circuit 108 fed to the TV monitor 86, and thus an endoscope image is reproduced on the TV monitor 86 in accordance with the composite type video signal. Of course, while the SDS display mode is selected, the reproduced endoscope image is observed as if it were sprayed with a blue solution.

Thus, according to the fifth embodiment, it is possible to simultaneously observe both the usual full color endoscope image and the simulated-dye-sprayed endoscope image on the TV monitors 84 and 86. Note, during the selection of the usual display mode, of course, the endoscope image is reproduced as a usual full color image on the TV monitor 86.

As shown in FIG. 19, the simulated dye-spraying process unit 82 has a front panel 110, on which a manual switch 112 is provided to thereby select either the usual display mode or the SDS display mode. Further, the simulated dye-spraying process unit 82 has a pedal switch 114, which is also provided for selecting either the usual display mode or the SDS display mode. The manual switch 112 is intended to be manually operated by an assistant, such as a nurse, whereas the pedal switch 114 is intended to be operated by a foot of a video-scope manipulator, such as a doctor.

Each of the manual and pedal switches 112 and 114 is constituted to alternately output a high-level signal or a low-level signal to the system control circuit 92 whenever it is operated. When the high-level signal is output from either the manual switch 112 or the pedal switch 114, the system control circuit 92 recognizes that the SDS display mode is selected. When the low-level signal is output from the either the manual switch 112 or the pedal switch 114, the system control circuit 92 to recognizes that the usual display mode is selected. In short, whenever either the manual switch 112 or the pedal switch 114 is operated, the usual display mode and the SDS display mode are alternately selected.

Also, in the fifth embodiment, a rotary digital switch may be provided on the front panel 110 to vary the value of the density factor "df". For example, the rotary digital switch is constituted so as to produce two-bit data [00], [01], [10], and [11], which respectively represent values of "10", "20", "40", and "80" for the density factor "df". When the rotary digital switch is manually operated, the two-bit data are selectively output from the rotary digital switch to the system control circuit 92. Namely, for example, when the two-bit data [01] is selected by manually operating the rotary digital switch, the setting of "20" is given to the density factor "df" by the system control circuit 92. Also, when the two-bit data [11] is selected by the rotary digital switch, the setting of "80" is given to the density factor "df" by the system control circuit 92.

Figure 21:
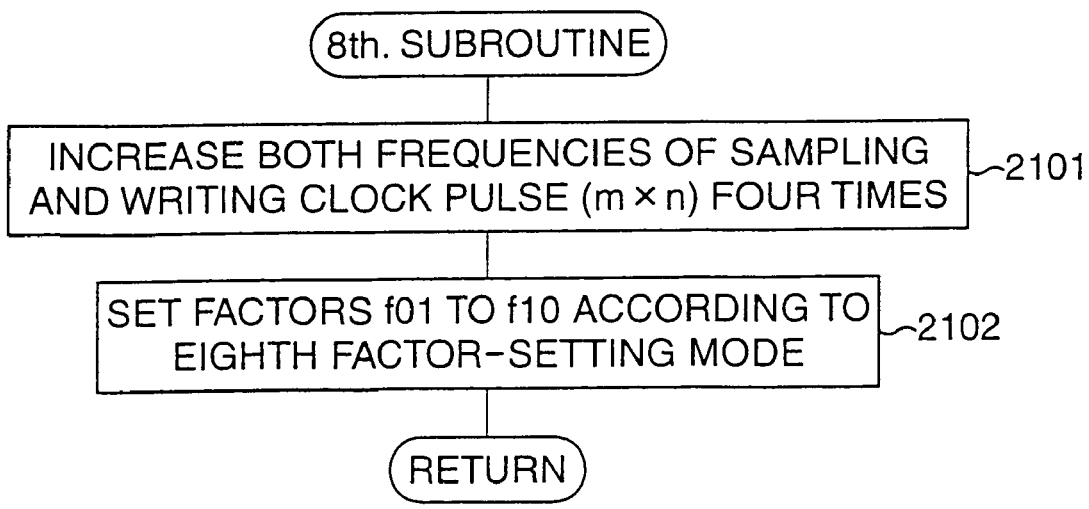
FIG. 21 is a flowchart of a display-mode-selection-monitoring routine executed in a system control circuit included in the fifth embodiment of the electronic endoscope system.

FIG. 21 shows a flowchart of a display-mode-selection-monitoring routine, which is formed as a time-interruption routine executed in the system control circuit 92 at regular suitable intervals of, for example, 20 ms. The execution of the routine is started after a power ON/OFF switch (not shown) of the simulated dye-spraying process unit 82 is turned ON, and is repeated every 20 ms as long as the power ON/OFF switch is turned ON.

At step 2101, it is monitored whether either the usual display mode or the SDS display mode has been changed to the other display mode by operating either the manual switch 112 or the pedal switch 114. When a change in the display mode is not confirmed, the routine immediately ends. Although the routine is repeatedly executed every 20 ms, there in no progress until a change in the display mode is confirmed.

At step 2101, when it is confirmed that the display mode has been changed, the control proceeds to step 2102, in which it is determined whether the usual display mode has been selected. When the selection of the usual display mode is confirmed, the control proceeds to step 2103, in which the setting of "0" is given to the density factor "df" in the multiplier 80.

At step 2102, when the selection of the usual display mode is not confirmed, i.e. when it is confirmed that the SDS display mode has been selected, the control proceeds from step 2102 to step 104, in which the setting of a plus value, for example, "20" is given to the density factor "df" in the multiplier 80.

Note, in the fifth embodiment, the SDS display mode is forcibly selected whenever the power ON/OFF switch is turned ON, the setting of "20" is automatically given to the density factor "df" after the turn-ON of the power ON/OFF switch.

In the fifth embodiment, although both the video scope 10 and the image-signal processing unit 12 are constituted so as to be in conformity with the RGB field sequential-type color imaging method, the on-chip color filter method may be used in both the video scope 10 and the image-signal processing unit 12.

Sixth Embodiment

Figure 22:
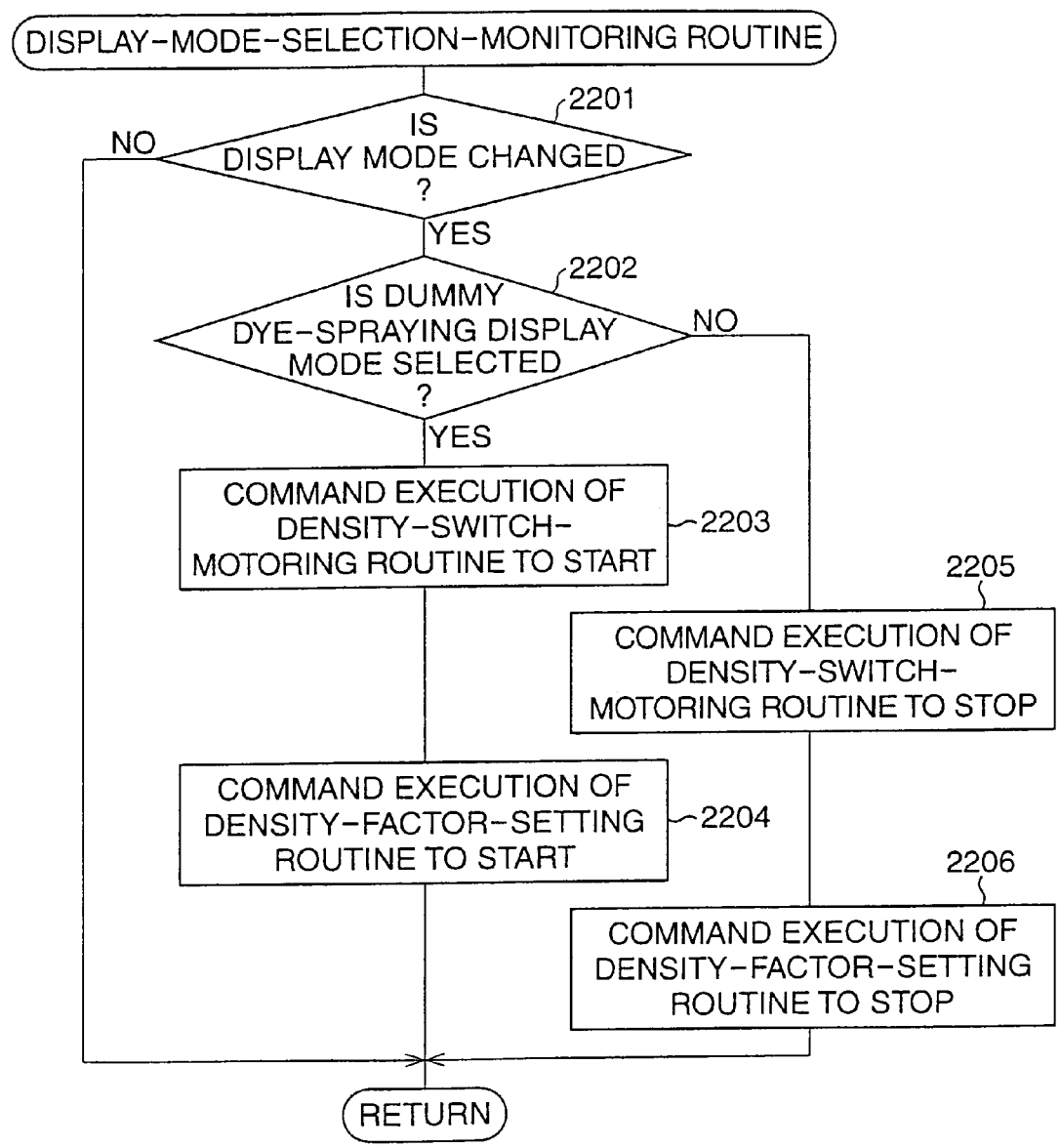
FIG. 22 is a schematic block diagram of a sixth embodiment of an electronic endoscope system according to the present invention.

Referring to FIG. 22, a sixth embodiment of an electronic endoscope system according to the present invention is shown as a block diagram, and the sixth embodiment is similar to the fifth embodiment. In this drawing, the features similar to those of FIG. 19 are indicated by the same references.

In the sixth embodiment, the electronic endoscope system also includes a video scope 10, an image-signal processing unit 12, a color-balance alteration process unit or simulated dye-spraying process unit 82, a first TV monitor 84, and a second monitor 86. Similar to the fifth embodiment, in the sixth embodiment, the RGB field sequential-type color imaging method is used, and thus the video scope 10 is constituted in substantially the same manner as in the first embodiment, and a light source device (24, 26, 28, and 30), provided in the image-signal processing unit 12, is also constituted in substantially the same manner as in the first embodiment.

In the sixth embodiment, the image-signal processing unit 12 is also provided with a system controller 88, and an image-signal processor 90. Similar to fifth embodiment, the system controller 88 includes a system control circuit and a timing controller, as indicated by references 32 and 34 in FIG. 1, and the image-signal processor 90 produces a component type video signal, composed of a red video signal component (R), a green video signal component (G), a blue video signal component (B), and a composite synchronizing signal component (S), based on frames of red, green, and blue analog image-pixel signals obtained from the video scope 10.

As shown in FIG. 22, in the sixth embodiment, the component type video signal (R, G, B, and S) is directly fed from the image-signal processor 90 to the TV monitor 84, and an endoscope image is reproduced as a usual full color image on the TV monitor 84 in accordance with the component type video signal (R, G, B, and S).

In the six embodiment, a character-generating circuit 116 is provided in the image-signal processing unit 12, and is operated under the control of the system controller 88. The character-generating circuit 116 produces character pattern signals based on code data which are input by operating a keyboard 58, and the character pattern data represent, for example, a patient's name, a patient's ID number, an examination date, a doctor's brief comments, and so on. The character pattern signals are output from the character-generating circuit 116 to the image-signal processor 90, and are added to the component type video signal (R, G, B, and S). Thus, character information, representing the patient's name, the patient's ID number, the examination date, and so on, is displayed together with a full color endoscope image on the TV monitor 84.

In the sixth embodiment, it is intended that two other types of video scopes 10' and 10" are selectively substituted for the video scope 10. The video scope 10' has a CCD image sensor 18', and the video scope 10" has a CCD image sensor 18". Note, in FIG. 22, references 10' and 10" are put in brackets adjacent to reference 10, and references 18' and 18" are put in brackets adjacent to reference 18.

As is apparent from the foregoing, the CCD image sensor 18 of the video scope 10 is constituted so as to produce a frame of m×n image pixel-signals. On the other hand, the CCD image sensor 18' is constituted so as to produce a frame of m'×n' image pixel-signals which is more than the number of m×n image pixel-signals (m'>m, n'>n), and the CCD image sensor 18" of the video scope 10" is constituted so as to produce a frame of m"×n" image pixel-signals which is less than the number of m×n image pixel-signals (m"<m, n"<n). In this case, a pixel pitch of the CCD image sensor 18 is larger than that of the CCD image sensor 18', and is smaller than that of the CCD image sensor 18".

As stated above, a frame of image-pixel signals, which is successively read from a CCD image sensor (18, 18', 18"), must be processed in the image-signal processor 90 in accordance with various series of clock pulses having given frequencies, before a video signal, such as a component type video signal, can be properly produced based on the processed image-pixel signals. For example, when the image-pixel signals are successively converted into digital image-pixel signals by an analog-to-digital (A/D) converter, the A/D converter must be operated in accordance with a series of sampling clock pulses having a given frequency, which is determined by the pixel-pitch of the CCD image sensor (18, 18', 18") used. Thus, the system controller 88 must recognize what type of video scope is connected to the image-signal processing unit 12.

To this end, the video scope (10, 10', 10") is provided with a read-only memory (ROM) 118 for storing pixel-number data, which represent any one of the number of m×n image pixel-signals, the number of m'×n' image pixel-signals, and the number of m"×n" image pixel-signals. When a connection is established between the video scope (10, 10', 10") and the image-signal processing unit 12, the ROM 118 is connected to the system controller 88, as shown in FIG. 22, whereby the pixel-number data is retrieved from the ROM 118 by the system controller 88. Thus, the system controller 88 can recognize what type of video scope (10, 10', 10") is used, whereby various series of clock pulses, having given frequencies based on the pixel number-data, are output from the system controller 88 to the image-signal processor 90. Thus, for example, when the video scope 10 is used, the frame of m×n image pixel-signals can be processed in the image-signal processor 90 at a proper timing.

As shown in FIG. 22, the simulated dye-spraying process unit 82 is provided with a system controller 120 including a system control circuit and a timing controller indicated by references 92 and 94 in FIG. 19. Also, a color-balance alteration processor 95 is arranged in substantially the same manner as that of the fifth embodiment. Thus, while a simulated dye-spraying (SDS) display mode is selected by operating either a manual switch 112 on a front panel 110 or a pedal switch 114, by feeding the component type video signal (R, G, B, S) to the simulated dye-spraying process unit 82, a simulated-dye-sprayed endoscope image can be reproduced on the TV monitor 86 in substantially the same manner as in the fifth embodiment.

When an uneven surface of the mucous membrane of a stomach or a colon is displayed as an endoscope image on the TV monitor 84, the displayed endoscope image exhibits a specific spatial frequency in accordance with the unevenness of the mucous membrane surface, and the spatial frequency varies according to the type of video scope (10, 10', 10") used. Namely, the spatial frequency is determined by a pixel pitch of a CCD image sensor (18, 18', 18").

Thus, the component type video signal (R, G, B, S) must be processed in the color-balance alteration processor 95 in accordance with the spatial frequency (and therefore, the pixel-pitch of the CCD image sensor (18, 18', 18")) of an endoscope image to be reproduced, before the color-balance alteration process can be properly performed in the first and second color-balance alteration circuits 102R and 102G. In other words, the color-balance alteration processor 95 must be operated in accordance with various series of clock pulse having given frequencies, which are determined by the pixel-pitch of the CCD image sensor (18, 18', 18"). Thus, the system controller 120 must recognize from what type of video scope (10, 10', 10") the component type video signal is derived.

To this end, the system controller 88 of the image-signal processing unit 12 is connected to the system controller 120 of the simulated dye-spraying process unit 82 such that the system controller 120 receives the pixel-number data (retrieved from the ROM 118) from the system controller 88. Thus, it is possible for the system controller 120 to recognize from what type of video scope (10, 10', 10") the component type video signal is derived.

Figure 23:
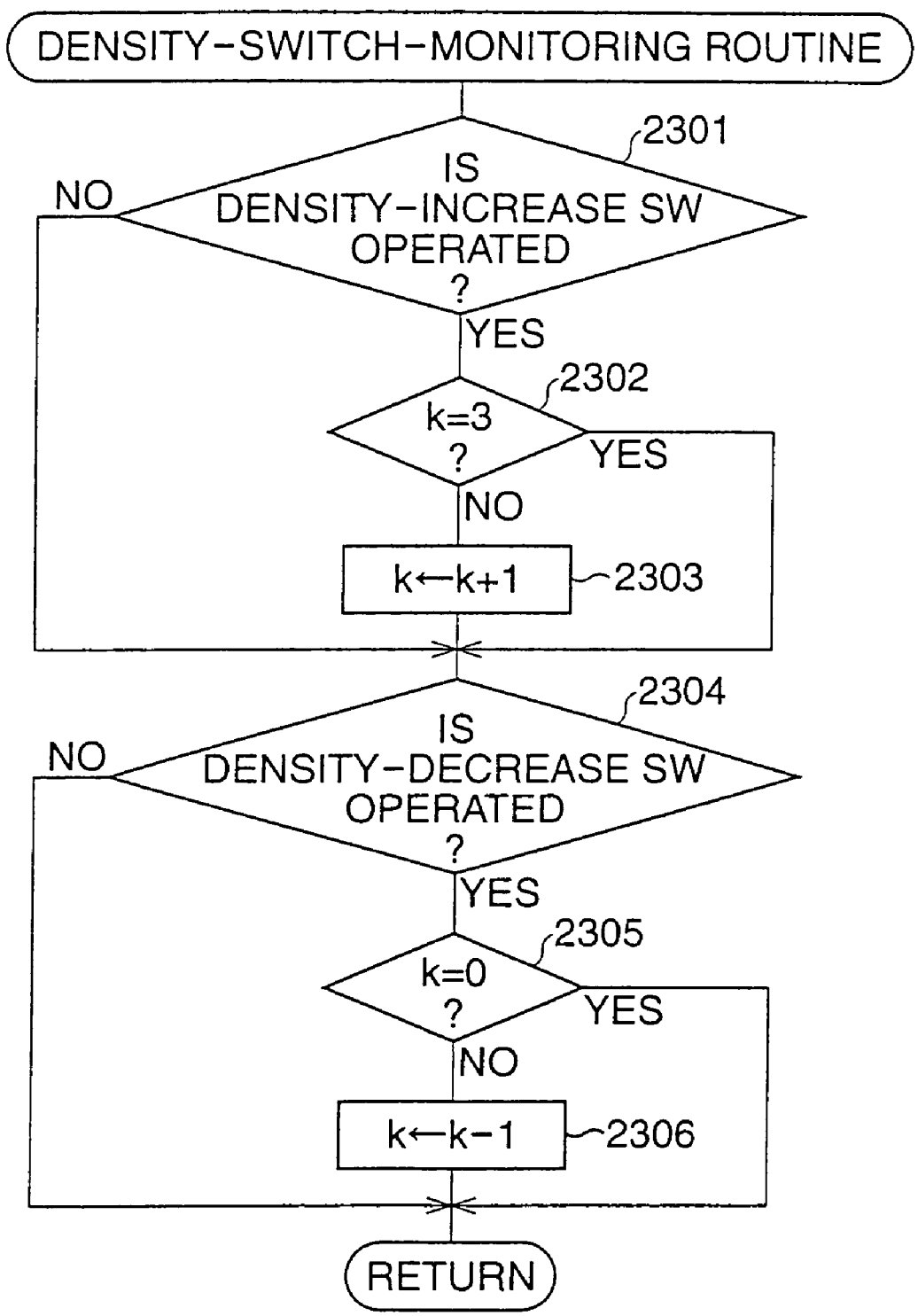
FIG. 23 is a schematic block diagram of a signal-generating circuit included in a system controller of a color-balance alteration process unit used in the sixth embodiment.

The system controller 120 includes a signal-generating circuit 122, as shown in FIG. 23, and the signal-generating circuit 122 is operated based on the pixel-signal data (fed from the system controller 88) under the control of the system control circuit included in the system controller 120.

As shown in FIG. 23, the signal-generating circuit 122 is provided with a first clock-pulse generator $124_1$, a second clock-pulse generator $124_2$, a third clock-pulse generator $124_3$, and a switching-circuit 126 associated with the first, second, and third clock pulse generators $124_1$, $124_2$, and $124_3$. Each of the first, second, and third clock-pulse generators $124_1$, $124_2$, and $124_3$ produces a series of clock pulses, having a given frequency, based on the composite synchronizing signal component (S) input to the system controller 120 (FIG. 22), and the series of clock pulses is output from each clock pulse generator ($124_1$, $124_2$, $124_3$) in synchronization with the composite synchronizing signal component (S). The clock pulses, output from the first clock-pulse generator $124_1$, have a suitable frequency for processing the component type video signal (R, G, B, S) derived from the video scope 10. Also, the clock pulses, output from the second clock-pulse generator $124_2$, have a higher frequency than that of the clock pulses output from the first clock-pulse generator $124_1$, and are suitable for processing the component type video signal (R, G, B, and S) derived from the video scope 10'. Further, the clock pulses, output from the third clock-pulse generator $124_3$, have a lower frequency than that of the clock pulses output from the first clock-pulse generator $124_1$, and are suitable for processing the component type video signal (R, G, B, and S) derived from the video scope 10".

On the other hand, the system control circuit, included in the system controller 120, produces any one of control signals ($AS_1$, $AS_2$, and $AS_3$) based on the pixel-number data received from the system controller 88 of the image-signal processing unit 12, and outputs the produced control signal ($AS_1$, $AS_2$, $AS_3$) to the switching-circuit 126. Namely, when the pixel-number data are derived from the video scope 10, the control signal $AS_1$ is output; when the pixel-number data are derived from the video scope 10', the control signal $AS_2$ is output; and, when the pixel-number data are derived from the video scope 10", the control signal $AS_3$ is output.

The switching-circuit 126 has an output terminal "OUT", and three input terminals "IN1", "IN2", and "IN3". When the control signal ($AS_1$) is input to the switching-circuit 126, a connection is established between the input terminal "IN1" and the output terminal "OUT". Also, when the control signal ($AS_2$) is input to the switching-circuit 126, a connection is established between the input terminal "IN2" and the output terminal "OUT". Further, when the control signal ($AS_3$) is input to the switching-circuit 126, a connection is established between the input terminal "IN3" and the output terminal "OUT".

Namely, when the video scope 10 is used, the first clock-pulse generator $124_1$ is selected by the switching-circuit 126; when the video scope 10' is used, the second clock-pulse generator $124_2$ is selected by the switching-circuit 126; and, when the video scope 10" is used, the third clock-pulse generator $124_3$ is selected by the switching-circuit 126. The clock pulses, output from the switching-circuit 126, are input to the timing controller of the system controller 120, and the timing controller produces and outputs various series of clock pulses to thereby operate the color-balance alteration processor 95.

As is apparent from the foregoing, in the sixth embodiment, the component type video signal (R, G, B, and S) contains the character information, representing, for example, the patient's name, the patient's ID number, the examination date, and so on, and thus the character information is displayed together with the simulated-dye-sprayed endoscope image on the TV monitor 86. In this case, the character pattern signals, carrying the character information, should be prevented from being subjected to the simulated dye-spraying process in the first and second color-balance alteration circuits 102R and 102G, because the patient's name, the patient's ID number, the examination date, and so on would not be properly displayed on the TV monitor 86 when the character pattern signals are subjected to the simulated dye-spraying process.

In particular, the patient's name, the patient's ID number, the examination date, and so on are usually displayed in white on the TV monitor 86. However, when the character pattern signals are subjected to the simulated dye-spraying process, a proper color balance of the character pattern signals may be broken.

In order to resolve the aforesaid problem, according to the sixth embodiment, only a desired area of an endoscope image, in which the patient's name, the patient's ID number, the examination date, and so on are not included, is reproduced on the TV monitor 86 as if it were sprayed with a blue solution. Namely, an area to be subjected to the simulated dye-spraying process is restricted on a display area of the TV monitor 86 for displaying the endoscope image, such that the patient's name, the patient's ID number, the examination date are not subjected to the simulated dye-spraying process.

Figure 24:
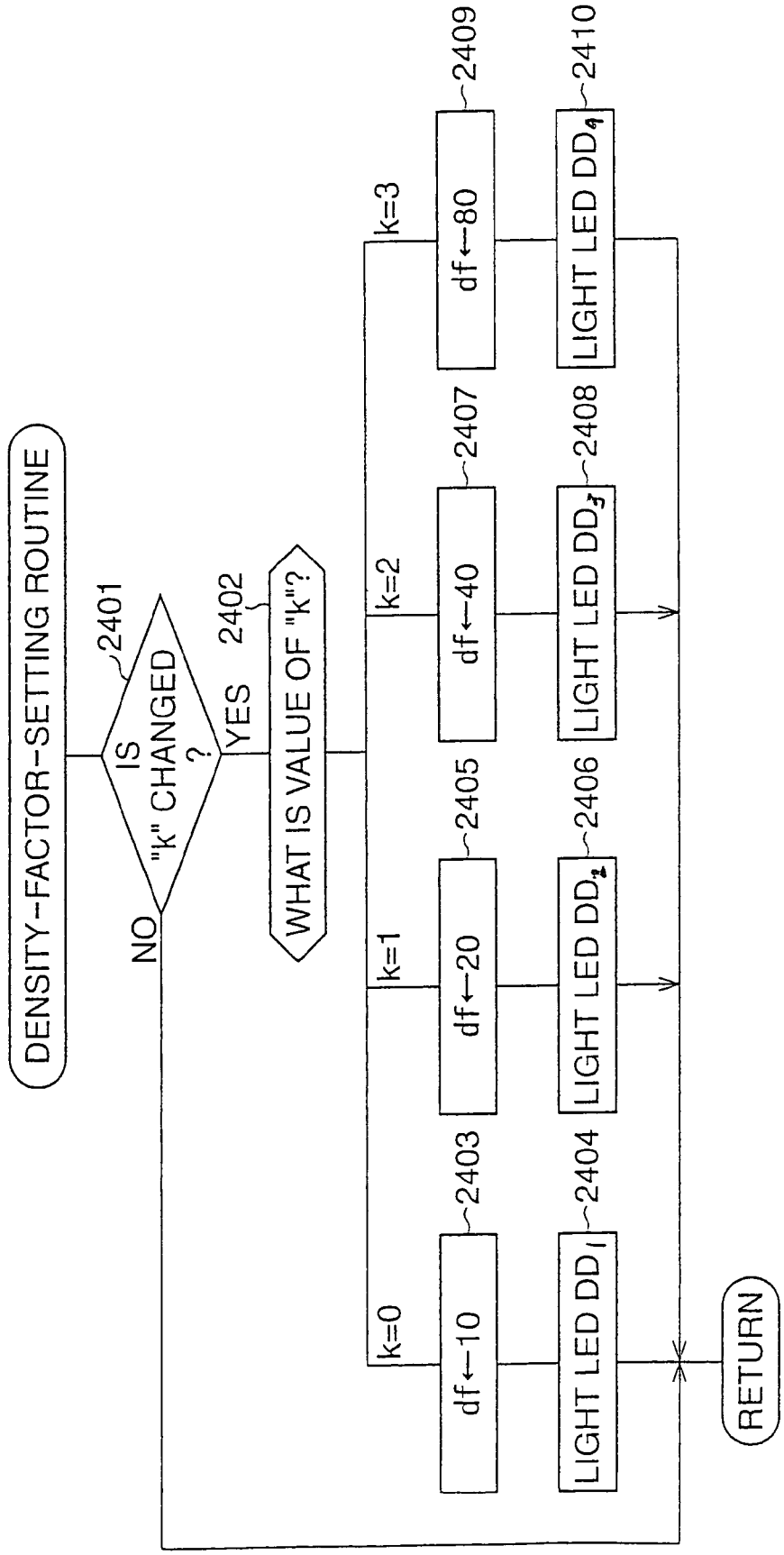
FIGS. 24(A), 24(B), and 24(C) are conceptual views showing first, second, and third display examples of how an area to be subjected to a simulated dye-spraying process is restricted on a display area of a TV monitor in the sixth embodiment.

FIGS. 24(A), 24(B), and 24(C) conceptually show first, second, and third display examples of how an area to be subjected to a simulated dye-spraying process is restricted on the display area of the TV monitor 86. In the drawings, reference DA indicates a display area for displaying the endoscope image; reference NA indicates an area for displaying a patient's name; reference IA indicates an area for displaying a patient's ID number; reference EA indicates an area for displaying an examination date, and reference CA indicates an area for displaying a doctor's brief comments.

In the first display example of FIG. 24(A), reference SIM1 indicates the area to be subjected to the simulated dye-spraying process. In this example, since the comment area CA is not defined on the display area DA, the area SIMI is defined as a maximum area on the display area DA. The character display areas NA, IA, and EA are not encompassed by the area SIMI, and thus the character information (NA, IA and EA) can be displayed in proper white on the TV monitor 86.

Note, in FIG. 24(A), reference $W_{1D}$ indicates a width between n upper boundary of the display area DA and an upper boundary of the area SIM1; reference $W_{1p}$ indicates a width between a lower boundary of the display area DA and a lower boundary of the area SIM1; reference $w_{1D}$ indicates a width between a left side boundary of the display area DA and a left side boundary of the area SIM1; and reference $w_{1p}$ indicates a width between a right side boundary of the display area DA and a right side boundary of the area SIM1.

In the second display example of FIG. 24(B), reference SIM2 indicates the area to be subjected to the simulated dye-spraying process. The area SIM2 is smaller than the area SIM1, due to the addition of the comment area CA on the display area DA, and thus the character display areas NA, IA, EA and CA are not encompassed by the area SIM2, and thus the character information (NA, IA, EA and CA) can be displayed in proper white on the TV monitor 86.

Note, in FIG. 24(B), reference $W_{2D}$ indicates a width between an upper boundary of the display area DA and an upper boundary of the area SIM2; reference $W_{2P}$ indicates a width between a lower boundary of the display area DA and a lower boundary of the area SIM2; reference $w_{2D}$ indicates a width between a left side boundary of the display area DA and a left side boundary of the area SIM2; and reference $w_{2P}$ indicates a width between a right side boundary of the display area DA and a right side boundary of the area SIM2.

In the third display example of FIG. 24(C), reference SIM3 indicates the area to be subjected to the simulated dye-spraying process. The third display example is substantially the same as the second display example, except that the area SIM3 is smaller than the area SIM2, and that the comment area CA is defined at a different location with respect to the second display example. Of course, the character information (NA, IA, EA and CA) can be displayed in proper white on the TV monitor 86, because the character display areas NA, IA, EA and CA are not encompassed by the area SIM3.

Note, in FIG. 24(C), reference $W_{3D}$ indicates a width between an upper boundary of the display area DA and an upper boundary of the area SIM3; reference $W_{3P}$ indicates a width between a lower boundary of the display area DA and a lower boundary of the area SIM3; reference $w_{3D}$ indicates a width between a left side boundary of the display area DA and a left side boundary of the area SIM3; and reference $W_3P$ indicates a width between a right side boundary of the display area DA and a right side boundary of the area SIM3.

In the sixth embodiment, any of the areas SIM1, SIM2, and SIM3 is manually selected by operating the keyboard 58. Namely, the selection of the areas SIM1, SIM2, and SIM3 are allocated to three function keys: the first, second, and third function keys on the keyboard 58, which respectively correspond to the areas SIM1, SIM2, and SIM3.

In particular, when the first function key is operated, a first selection signal (indicated by reference $SS_1$ in FIG. 26) is produced in the system controller 88 of the image-signal processing unit 12, and is then fed to the system controller 120 of the simulated dye-spraying process unit 82, whereby the selection of the area SIM1 is recognized by the system controller 120. When the second function key is operated, a second selection signal (indicated by reference $SS_2$ in FIG. 26) is produced in the system controller 88, and is then fed to the system controller 120, whereby the selection of the area SIM2 is recognized by the system controller 120. Further, when the third function key is operated, a third selection signal (indicated by reference $SS_3$ in FIG. 26) is produced in the system controller 88, and is then fed to the system controller 120, whereby the selection of the area SIM3 is recognized by the system controller 120.

Figure 25:
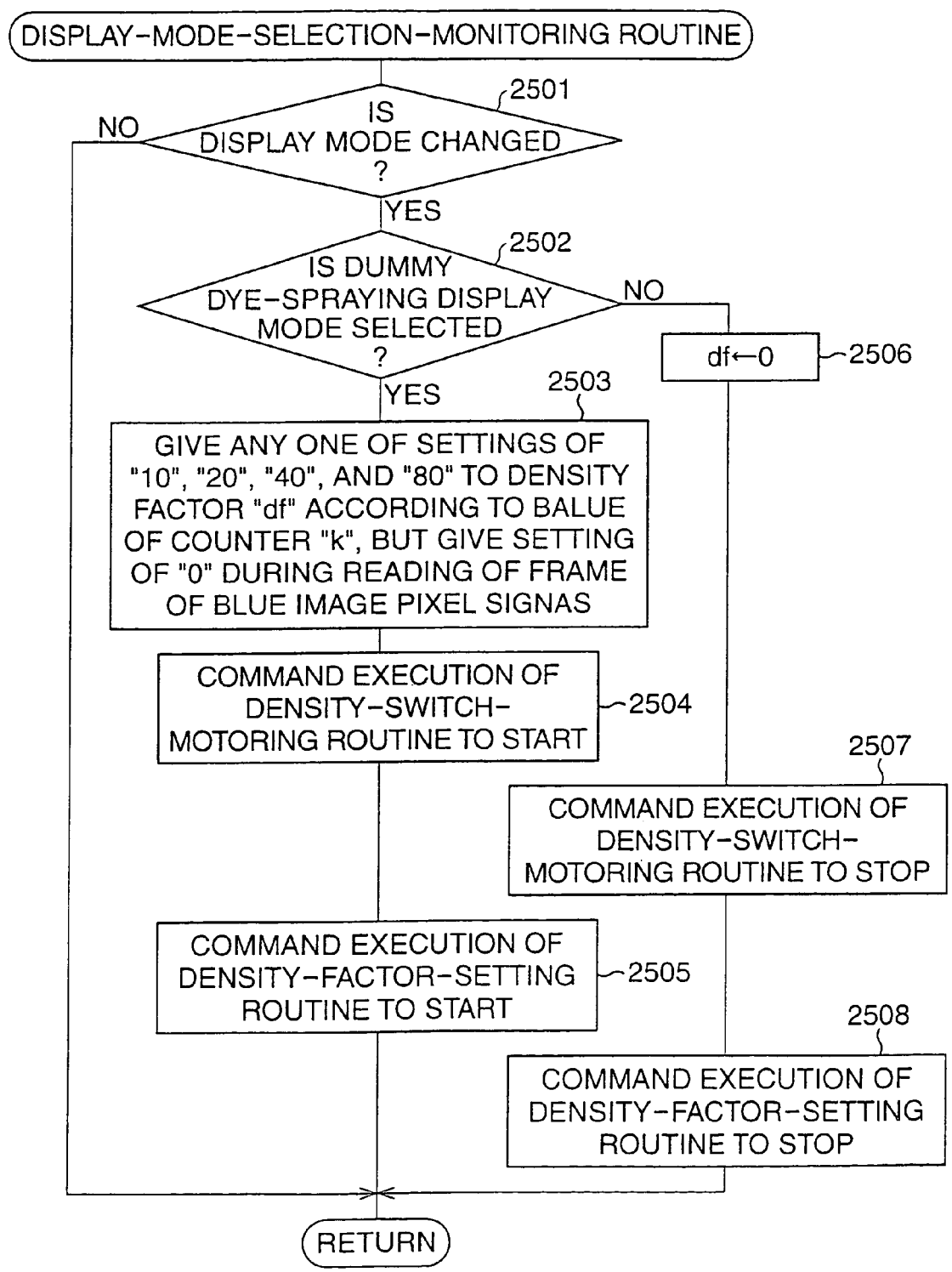
FIG. 25 is a schematic block diagram of a color-balance alteration circuit used as a simulated dye-spraying process circuit in the sixth embodiment of the electronic endoscope system.

In the sixth embodiment, in order that an area (SIM1, SIM2, SIM3) to be subjected to a simulated dye-spraying process can be restricted on the display area DA on the TV monitor 96, each of the first and second color-balance alteration circuits 102R and 102G is arranged, as shown in FIG. 25. As is apparent from this drawing, each color-balance alteration circuit (102R, 102G) is essentially identical to that of FIG. 20 except that an AND-logic circuit 128 intervenes between a multiplier 80 and an adder 72.

The AND-logic circuit 128 includes a set of eight AND-gates, and a digital signal (df*$\Delta R_{ij}$, df*$\Delta G_{ij}$), output from the multiplier 80, is input to the eight AND-gates in a set. Note, as already stated above, a digital image-pixel ($R_{ij}$, $G_{ij}$) is composed of eight bits. When the digital signal (df*$\Delta R_{ij}$, df*$\Delta G_{ij}$) concerned corresponds to an image pixel encompassed by the restricted area (SIM1, SIM2, SIM3), a high-level signal (i.e., "$b_1$") is output from the system controller 120 to the eight AND-gates in a set, such that the digital signal (df*$\Delta R_{ij}$, df*$\Delta G_{ij}$) passes through the AND-logic circuit 128 as it stands. On the other hand, when the digital signal (df*$\Delta R_{ij}$, df*$\Delta G_{ij}$) concerned corresponds to an image pixel not encompassed by the restricted area (SIM1, SIM2, SIM3), a low-level signal (i.e., "0") is output from the system controller 120 to the eight AND-gates in a set, such that the digital signal (df*$\Delta R_{ij}$, df*$\Delta G_{ij}$) is output as a zero signal from the AND-logic circuit 128. Thus, only an image section, encompassed by the restricted area (SIM1, SIM2, SIM3), is reproduced on the TV monitor 86 as if it were sprayed with a blue solution, and thus it is possible to display the character information in proper white on the TV monitor 86.

Figure 26:
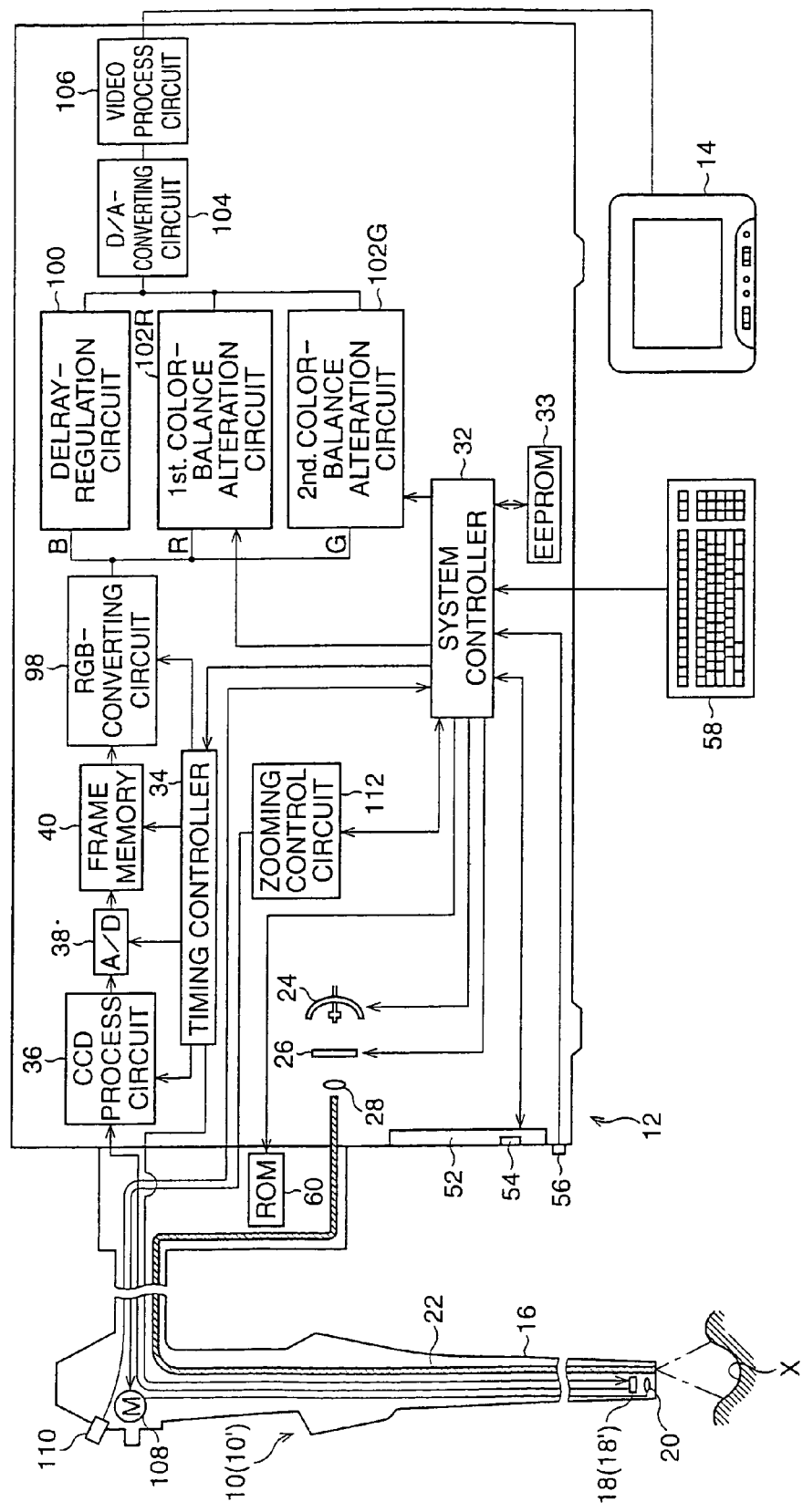
FIG. 26 is a schematic block diagram of another signal-generating circuit included in the system controller of the color-balance alteration process unit used in the sixth embodiment.

Referring to FIG. 26, a signal-generating circuit 130 for controlling the AND-logic circuit 128 is shown as a block diagram, and is contained in the system controller 120. As shown in this drawing, the signal-generating circuit 130 includes a first set of a first frame-control-signal generator $130F_1$, a first line-control-signal generator $130L_1$, and a first AND-gate $130A_1$; a second set of a second frame-control-signal generator $130F_2$, a second line-control-signal generator $130L_2$, and a second AND-gate $130A_2$; a third set of a third frame-control-signal generator $130F_3$, a third line-control-signal generator $130L_3$, and a third AND-gate $130A_3$; and a switching-circuit 130S associated with the first, second, and third AND-gates $130A_1$, $130A_2$, and $130A_3$.

As shown in FIG. 26, the switching-circuit 130S has an output terminal "OUT", and three input terminals "IN1", "IN2", and "IN3", and the respective output terminals of the first, second, and third AND-gates $130A_1$, $130A_2$, and $130A_3$ are connected to the input terminals "IN1", "IN2", and "IN3". When the aforesaid first selection signal ($SS_1$) is fed from the system controller 88 of the image-signal processing unit 12 to the switching-circuit 130S though the system controller 120, a connection is established between the input terminal "IN1" and the output terminal "OUT". Also, when the aforesaid second selection signal ($SS_2$) is fed from the system controller 88 to the switching-circuit 130S through the system controller 120, a connection is established between the input terminal "IN2" and the output terminal "OUT". Further, when the aforesaid third selection signal ($SS_3$) is input from the system controller 88 to the switching-circuit 130S through the system controller 120, a connection is established between the input terminal "IN3" and the output terminal "OUT".

While the multiplier 80 successively outputs a frame of red or green digital signals (df*$\Delta R_{ij}$ or df*$\Delta G_{ij}$), as indicated by item (a) of a timing chart of FIG. 27, the first frame-control-signal generators $130F_1$ produces and outputs a first frame-control signal, as indicated by item (b) of the timing chart of FIG. 27. Namely, the first frame-control signal changes from a low-level to a high-level at a delay time $T_{1D}$ with respect to the outputting of a leading digital signal (df*$\Delta R_{11}$ or df*$\Delta G_{11}$), included in each frame, from the multiplier 80, and changes from the high-level to the low-level at a premature time $T_{1P}$ with respect to the outputting of a trailing digital signal (df*$\Delta R_{mn}$ or df*$\Delta G_{mn}$), included in each frame, from the multiplier 80. Note, the respective delay time $T_{1D}$ and premature time $T_{1P}$ correspond to the widths $W_{1D}$ and $W_{1P}$ shown in FIG. 24(A).

Figure 28:
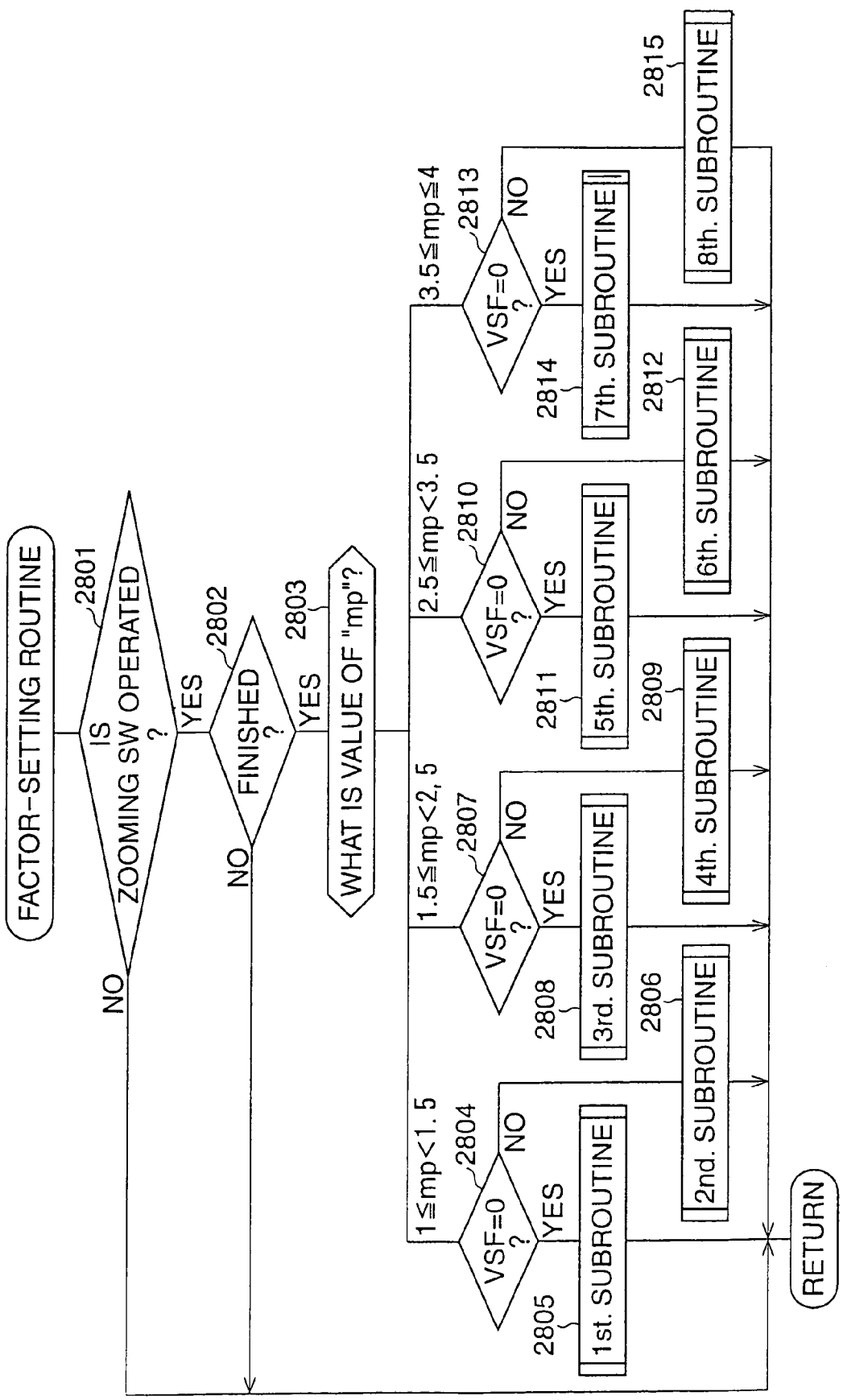
FIG. 28 is another timing chart for explaining the operation of the signal-generating circuit shown in FIG. 26.

On the other hand, while the multiplier 80 successively outputs a line of red or green digital signals ($df^*\Delta R_{ij}$ or $df^*\Delta G_{ij}$), as indicated by item (a) of a timing chart of FIG. 28. The first line-control-signal generator 130L$_1$ produces and outputs a first line-control signal, as indicated by item (b) of the timing chart of FIG. 28. Namely, the first line-control signal changes from a low-level to a high-level at a delay time $t_{1D}$ with respect to the outputting of a leading digital signal ($df^*\Delta R_{k1}$ or $df^*\Delta G_{k1}$)($1 \leq k \leq m$), included in each line, from the multiplier 80, and changes from the high-level to the low-level at a premature time $t_{1P}$ with respect to the outputting of a trailing digital signal ($df^*\Delta R_{kn}$ or $df^*\Delta G_{kn}$), included in each line, from the multiplier 80. Note, the respective delay time $t_{1D}$ and premature time $t_{1P}$ correspond to the widths $w_{1D}$ and $w_{1P}$ shown in FIG. 24(A).

Thus, only while the multiplier 80 outputs the digital signals ($df^*\Delta R_{mn}$ or $df^*66 G_{mn}$) corresponding to the image pixels encompassed by the area SIM1, does the first AND-gate 130A$_1$ output the high-level signal. When the area SIM1 is selected as an area to be subjected to a simulated dye-spraying process on the TV monitor 86, i.e. when the connection is established between the input terminal "IN1" and the output terminal "OUT" in the switching-circuit 130S, the high-level signal, output from the first AND-gate 130A$_1$, is input to the AND-logic circuit 128. Thus, only the image section, encompassed by the area SIM1 is reproduced on the TV monitor 86 as if it were sprayed with a blue solution.

The second frame-control-signal generators 130F$_2$ produces and outputs a second frame-control signal, as indicated by item (c) of the timing chart of FIG. 27. Namely, the second frame-control signal changes from a low-level to a high-level at a delay time $T_{2D}$ with respect to the outputting of a leading digital signal ($df^*\Delta R_{11}$ or $df^*\Delta G_{11}$), included in each frame, from the multiplier 80, and changes from the high-level to the low-level at a premature time $T_{2P}$ with respect to the outputting of a trailing digital signal ($df^*\Delta R_{mn}$ or $df^*\Delta G_{mn}$), included in each frame, from the multiplier 80. Note, the respective delay time $T_{2D}$ and premature time $T_{2P}$ correspond to the widths $W_{2D}$ and $W_{2P}$ shown in FIG. 24(B).

The second line-control-signal generator 130L$_2$ produces and outputs a second line-control signal, as indicated by item (c) of the timing chart of FIG. 28. Namely, the second line-control signal changes from a low-level to a high-level at a delay time $t_{2D}$ with respect to the outputting of a leading digital signal ($df^*\Delta R_{k1}$ or $df^*\Delta G_{k1}$)($1 \leq k \leq m$), included in each line, from the multiplier 80, and changes from the high-level to the low-level at a premature time $t_{2P}$ with respect to the outputting of a trailing digital signal ($df^*\Delta R_{kn}$ or $df^*\Delta G_{kn}$), included in each line, from the multiplier 80. Note, the respective delay time $t_{2D}$ and premature time $t_{2P}$ correspond to the widths $w_{2D}$ and $w_{2P}$ shown in FIG. 24(B).

Thus, only while the multiplier 80 outputs the digital signals ($df^*\Delta R_{mn}$ or $df^*\Delta G_{mn}$) corresponding to the image pixels encompassed by the area SIM2, does the second AND-gate 130A$_2$ output the high-level signal. When the area SIM2 is selected as an area to be subjected to a simulated dye-spraying process on the TV monitor 86, i.e. when the connection is established between the input terminal "IN2" and the output terminal "OUT" in the switching-circuit 130S, the high-level signal, output from the second AND-gate 130A$_2$, is input to the AND-logic circuit 128. Thus, only the image section, encompassed by the area SIM2 is reproduced on the TV monitor 86 as if it were sprayed with a blue solution.

The third frame-control-signal generators 130F$_3$ produces and outputs a third frame-control signal, as indicated by item (d) of the timing chart of FIG. 27. Namely, the third frame-control signal changes from a low-level to a high-level at a delay time $T_{3D}$ with respect to the outputting of a leading digital signal ($df^*\Delta R_{11}$ or $df^*\Delta G_{11}$), included in each frame, from the multiplier 80, and changes from the high-level to the low-level at a premature time $T_{3P}$ with respect to the outputting of a trailing digital signal ($df^*\Delta R_{mn}$ or $df^*\Delta G_{mn}$), included in each frame, from the multiplier 80. Note, the respective delay time $T_{3D}$ and premature time $T_{3P}$ correspond to the widths $W_{3D}$ and $W_{3P}$ shown in FIG. 24(C).

The third line-control-signal generator 130L$_2$ produces and outputs a third line-control signal, as indicated by item (d) of the timing chart of FIG. 28. Namely, the third line-control signal changes from a low-level to a high-level at a delay time $t_{3D}$ with respect to the outputting of a leading digital signal ($df^*\Delta R_{k1}$ or $df^*\Delta G_{k1}$)($1 \leq k \leq m$), included in each line, from the multiplier 80, and changes from the high-level to the low-level at a premature time $t_{3P}$ with respect to the outputting of a trailing digital signal ($df^*\Delta R_{kn}$ or $df^*\Delta G_{kn}$), included in each line, from the multiplier 80. Note, the respective delay time $t_{3D}$ and premature time $t_{3P}$ correspond to the widths $w_{3D}$ and $W_{3P}$ shown in FIG. 24(C).

Thus, only while the multiplier 80 outputs the digital signals ($df^*\Delta R_{mn}$ or $df^*\Delta G_{mn}$) corresponding to the image pixels encompassed by the area SIM3, does the third AND-gate 130A$_3$ output the high-level signal. When the area SIM3 is selected as an area to be subjected to a simulated dye-spraying process on the TV monitor 86, i.e. when the connection is established between the input terminal "IN3" and the output terminal "OUT" in the switching-circuit 130S, the high-level signal, output from the third AND-gate 130A$_3$, is input to the AND-logic circuit 128. Thus, only the image section, encompassed by the area SIM3 is reproduced on the TV monitor 86 as if it were sprayed with a blue solution.

Similar to the fifth embodiment, in the sixth embodiment, although both the video scope (10, 10', 1") and the image-signal processing unit 12 are constituted so as to be in conformity with the RGB field sequential-type color imaging method, the on-chip color filter method may be used in both the video scope (10, 10', 10") and the image-signal processing unit 12.

Seventh Embodiment

Figure 29:
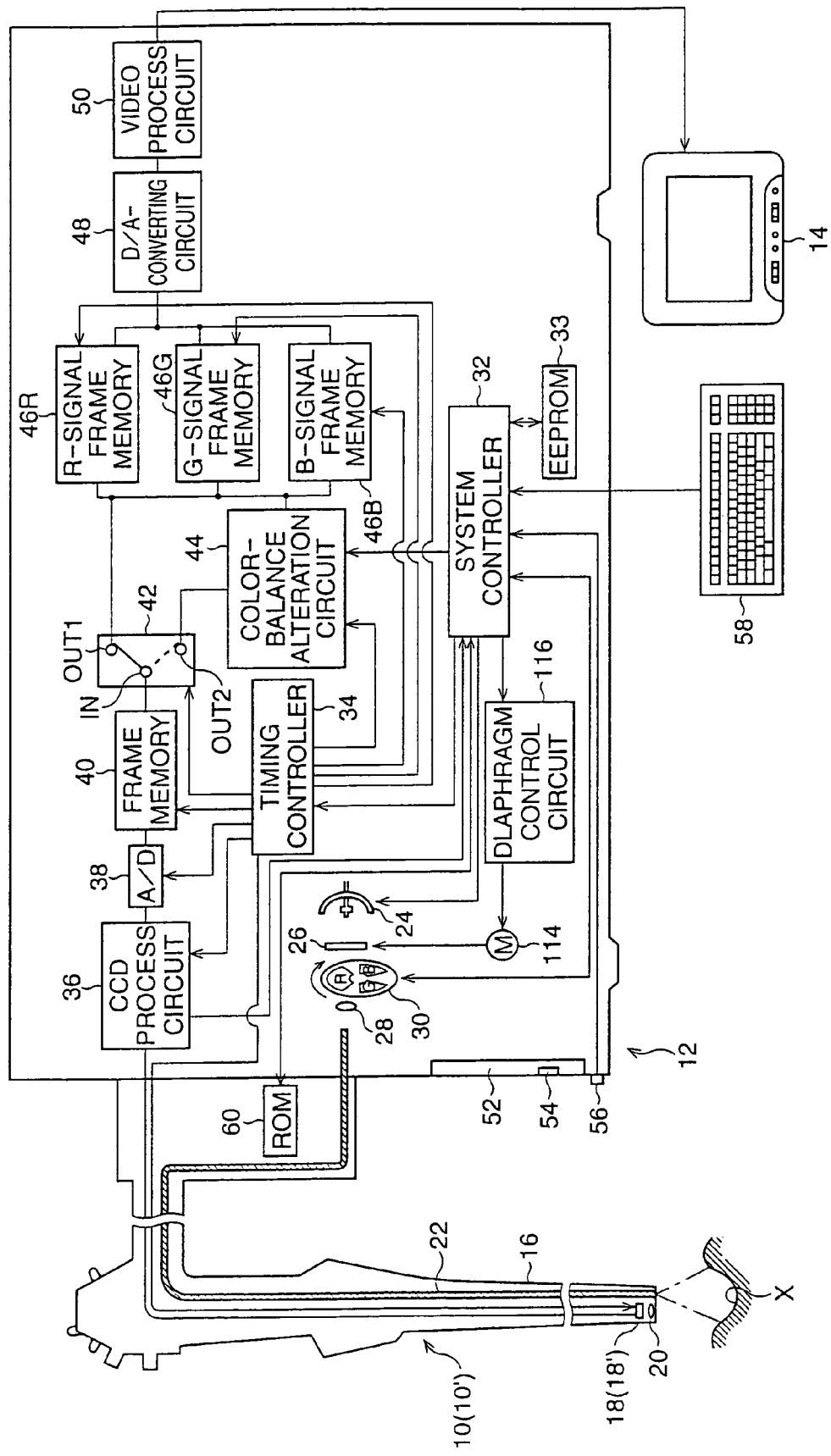
FIG. 29 is a schematic block diagram of a seventh embodiment of an electronic endoscope system according to the present invention.

Referring to FIG. 29, a seventh embodiment of an electronic endoscope system according to the present invention is shown as a block diagram. As is apparent from this drawing, the seventh embodiment is generally identical to the first embodiment shown in FIG. 1. In FIG. 29, the features similar to those of FIG. 1 are indicated by the same references. According to the seventh embodiment, the electronic endoscope system is constituted such that an endoscope image to be reproduced on a TV monitor 14 is subjected to a specific color-balance alteration process rather than a simulated dye-spraying process, if necessary.

A mucous membrane surface in a human's body does not necessarily feature a reddish orange tone as a whole. For example, here is a case where veins, having a bluish tone, appear on the mucous membrane surface. In this case, when an area of the mucous membrane surface, in which the veins are included, is subjected to the aforesaid simulated dye-spraying process, and when that area is reproduced as an endoscope image on the TV monitor 14, it is very difficult to discriminate the existence of the veins on the reproduced endoscope image. The seventh embodiment is directed to resolution of this problem. Namely, according to the seventh embodiment, it is possible to clearly observe and examine a subtle unevenness of the mucous membrane surface even if it features any tone of color.

Similar to the first embodiment, frames of red, green, and blue image-pixel signals are cyclically and successively read from a CCD image sensor 18 of a video scope 10, and the read image-pixel signals are successively converted into digital image-pixel signals. Then, the converted digital image-pixel signals are written and stored in a frame memory 40.

In the seventh embodiment, the frame memory 40 has sufficient memory capacity for the storage of the three frames of digital image-pixel signals ($R_{ij}$, $G_{ij}$ and $B_{ij}$), and the red, green, and blue digital image-pixel signals ($R_{ij}$, $G_{ij}$ and $B_{ij}$) are simultaneously read from the frame memory 40. The read red, green, and blue digital image-pixel signals ($R_{ij}$, $G_{ij}$ and $B_{ij}$) are then fed to a color-balance alteration processor 132.

In the seventh embodiment, either a usual display mode or a color-balance alteration (CBA) display mode is selected by manually operating a display-mode selection switch 54 on a front panel 52. Similar to the first embodiment, a function, pertaining to the display-mode selection switch 54, may be allocated to a function key on the keyboard 58.

While the usual display mode is selected, the red, green, and blue digital image-pixel signals ($R_{ij}$, $G_{ij}$, and $B_{ij}$) pass through the color-balance alteration processor 132 as they stand, as stated in detail hereinafter. Namely, the red, green, and blue digital image-pixel signals ($R_{ij}$, $G_{ij}$ and $B_{ij}$) are fed to a digital-to-analog (D/A) converting circuit 48, without any color-balance alteration process by the color-balance alteration processor 132.

Similar to the first embodiment, the D/A converting circuit 48 includes three digital-to-analog (D/A) converters. The read red, green, and blue digital image-pixel signals ($R_{ij}$, $G_{ij}$, and $B_{ij}$) are respectively converted into red, green, and blue analog image signals by the three D/A converters of the D/A converting circuit 48, and the red, green, and blue analog image signals are output from the D/A converting circuit 48 to a video process circuit 50. On the other hand, the timing controller 34 produces a composite synchronizing signal, and the composite synchronizing signal is output from the timing controller 34 to the video process circuit 50. Similar to the first embodiment, the video process circuit 50 produces a component type video signal based on the red, green, and blue analog image signals output from the D/A converting circuit 48, and the synchronizing signal output from the timing controller 34. Thus, during the selection of the usual display mode, an endoscope image, sensed by the CCD image sensor 18, is reproduced as a full color motion picture on the TV monitor 14 with a given proper color balance in accordance with the component type video signal.

As shown in FIG. 29, the color-balance alteration processor 132 includes a comparator circuit 133, which is arranged as shown in FIG. 30. Namely, the comparator circuit 133 includes a delay circuit 134, a first set of comparators 136$_{RG}$ and 136$_{RB}$, a first AND-gate 138$_1$ associated with the comparators 136$_{RG}$ and 136$_{RB}$, a first NOT-gate 140$_1$ associated with the first AND-gate 138$_1$, a second set of comparators 136$_{GR}$ and 136$_{GB}$, a second AND-gate 138$_2$ associated with the comparators 136$_{GR}$ and 136$_{GB}$, a second NOT-gate 140$_2$ associated with the second AND-gate 138$_2$, a third set of comparators 136$_{BR}$ and 136$_{DG}$, a third AND-gate 138$_3$ associated with the comparators 136$_{BR}$ and 136$_{BG}$, and a third NOT-gate 140$_3$ associated with the third AND-gate 138$_3$.

The red, green, and blue digital image-pixel signals ($R_{ij}$, $G_{ij}$, and $B_{ij}$) simultaneously read from the frame memory 40, are input to the delay circuit 134, and are output from the delay circuit 134 after a lapse of a predetermined delay-time.

The red and green digital image-pixel signals ($R_{ij}$ and $G_{ij}$) are input to the comparator 136$_{RG}$, and the red and blue digital image-pixel signals ($R_{ij}$ and $B_{ij}$) are input to the comparator 136$_{RB}$. When a value of the red signal ($R_{ij}$) is equal to or more than a value of the green signal ($G_{ij}$), the comparator 136$_{RG}$ outputs a high-level signal (i.e., "1") to the first AND-gate 138$_1$. When the value of the red signal ($R_{ij}$) is less than a value of the green signal ($G_{ij}$), the comparator 136$_{RG}$ outputs a low-level signal (i.e., "0") to the first AND-gate 138$_1$. On the other hand, when the value of the red signal ($R_{ij}$) is equal to or more than a value of the blue signal ($B_{ij}$), the comparator 136$_{RB}$ outputs a high-level signal (i.e., "1") to the first AND-gate 138$_1$. When the value of the red signal ($R_{ij}$) is less than a value of the blue signal ($B_{ij}$), the comparator 136$_{RB}$ outputs a low-level signal (i.e., "0") to the first AND-gate 138$_1$.

Thus, only when the value of the red signal ($R_{ij}$) is more than the value of the green and blue ($G_{ij}$ and $B_{ij}$), i.e. only when the value of the red signal ($R_{ij}$) is maximum, does the first AND-gate 138$_1$ output a high-level signal (i.e., "1"). Unless the value of the red signal ($R_{ij}$) is maximum, the first AND-gate 138$_1$, outputs a low-level signal (i.e., "0"). The first NOT-gate 140$_1$, outputs a low-level signal (i.e., "0") when the output of the first AND-gate 138$_1$ is high level, and outputs a high-level signal (i.e., "1") when the output of the first AND-gate 138$_1$ is low level. Namely, only when the value of the red signal ($R_{ij}$) is maximum, is the low-level signal (i.e., "0") output from the first NOT-gate 140$_1$.

Also, the green and red digital image-pixel signals ($G_{ij}$ and $R_{ij}$) are input to the comparator 136$_{GR}$, and the green and blue digital image-pixel signals ($G_{ij}$ and $B_{ij}$) are input to the comparator 136$_{GB}$. When the value of the green signal ($G_{ij}$) is equal to or more than the value of the red signal ($R_{ij}$), the comparator 136$_{GR}$ outputs a high-level signal (i.e., "1") to the second AND-gate 138$_2$. When the value of the green signal ($G_{ij}$) is less than the value of the red signal ($R_{ij}$), the comparator 136$_{GR}$ outputs a low-level signal (i.e., "0") to the second AND-gate 138$_2$. On the other hand, when the value of the green signal ($G_{ij}$) is equal to or more than the value of the blue signal ($B_{ij}$), the comparator 136$_{GB}$ outputs a high-level signal (i.e., "1") to the second AND-gate 138$_2$. When the value of the green signal ($G_{ij}$) is less than the value of the blue signal ($B_{ij}$), the comparator 136$_{GB}$ outputs a low-level signal (i.e., "0") to the second AND-gate 138$_2$.

Thus, only when the value of the green signal ($G_{ij}$) is more than the value of the red and blue ($R_{ij}$ and $B_{ij}$), i.e. only when the value of the green signal ($G_{ij}$) is maximum, does the second AND-gate 138$_2$ output a high-level signal (i.e., "1"). Unless the value of the green signal ($G_{ij}$) is maximum, the second AND-gate 138$_2$ outputs a low-level signal (i.e., "0"). The second NOT-gate 140$_2$ outputs a low-level signal (i.e., "0") when the output of the second AND-gate 138$_2$ is high level, and outputs a high-level signal (i.e., "1") when the output of the second AND-gate 138$_2$ is low level. Namely, only when the value of the green signal ($G_{ij}$) is maximum, is the low-level signal (i.e., "0") output from the second NOT-gate 140$_2$.

Similarly, the blue and red digital image-pixel signals ($B_{ij}$ and $R_{ij}$) are input to the comparator 136$_{BR}$, and the blue and green digital image-pixel signals ($B_{ij}$ and $G_{ij}$) are input to the comparator 136$_{BG}$. When the value of the blue signal ($B_{ij}$) is equal to or more than the value of the red signal ($R_{ij}$), the comparator 136$_{BR}$ outputs a high-level signal (i.e., "1") to the third AND-gate $138_3$. When the value of the blue signal ($B_{ij}$) is less than the value of the red signal ($R_{ij}$), the comparator $136_{BR}$ outputs a low-level signal (i.e., "0") to the third AND-gate $138_3$. On the other hand, when the value of the blue signal ($B_{ij}$) is equal to or more than the value of the green signal ($G_{ij}$), the comparator $136_{BG}$ outputs a high-level signal (i.e., "1") to the third AND-gate $138_3$. When the value of the blue signal ($B_{ij}$) is less than the value of the green signal ($G_{ij}$), the comparator $136_{BG}$ outputs a low-level signal (i.e., "0") to the third AND-gate $138_3$.

Thus, only when the value of the blue signal ($B_{ij}$) is more than the value of the red and green ($R_{ij}$ and $G_{ij}$) i.e. only when the value of the blue signal ($B_{ij}$) is maximum, does the third AND-gate $138_3$ output a high-level signal (i.e., "1"). Unless the value of the blue signal ($B_{ij}$) is maximum, the third AND-gate $138_3$ outputs a low-level signal (i.e., "0"). The third NOT-gate $140_3$ outputs a low-level signal (i.e., "0") when the output of the third AND-gate $138_3$ is high level, and outputs a high-level signal (i.e., "1") when the output of the third AND-gate $138_3$ is low level. Namely, only when the value of the blue signal ($B_{ij}$) is maximum, is the low-level signal (i.e., "0") output from the third NOT-gate $140_3$.

The color-balance alteration processor 132 also includes a first color-balance alteration circuit $142_1$, a second color-balance alteration circuit $142_2$, and a third color-balance alteration circuit $142_3$, which are identical to each other. The red, green, and blue digital image-pixel signals ($R_{ij}$, $G_{ij}$, and $B_{ij}$), simultaneously read from the frame memory 40, are respectively input to the first, second, and third color-balance alteration circuits $142_1$, $142_2$, and $142_3$.

Figure 31:
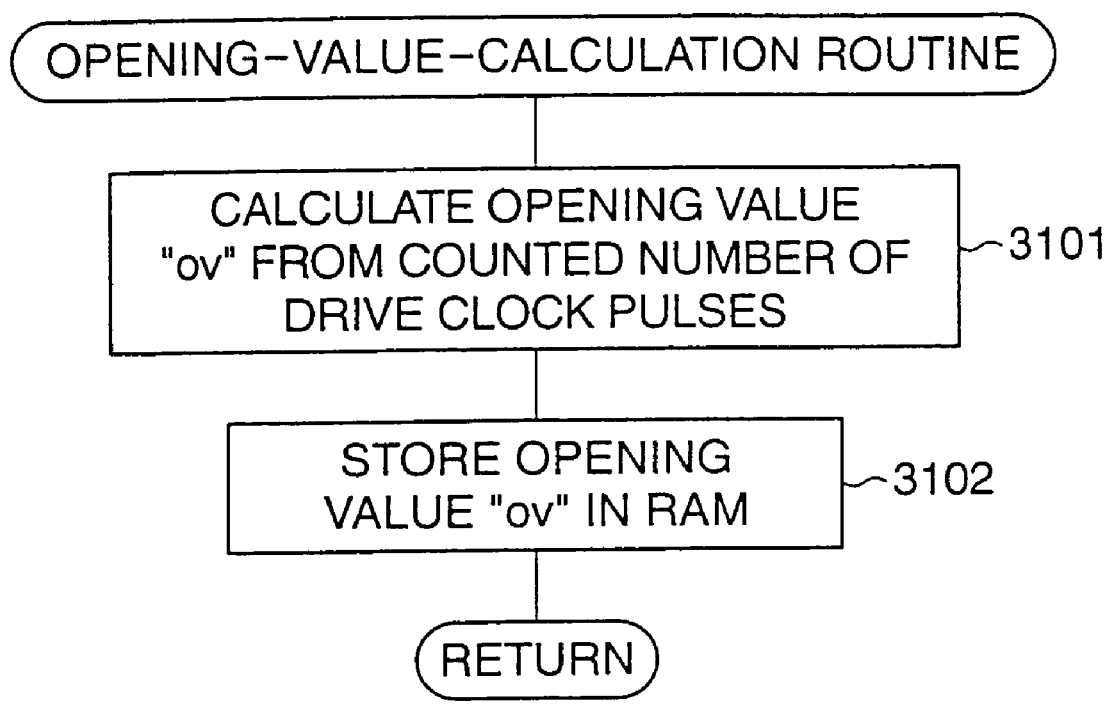
FIG. 31 is a schematic block diagram of a first color-balance alteration circuit included in the color-balance alteration processor shown in FIG. 29.

Referring to FIG. 31, the first color-balance alteration circuit $142_1$ is representatively shown, and is essentially identical to the color-balance alteration circuit (102R, 102G), shown in FIG. 25, which is used in the seventh embodiment. In FIG. 31, the elements similar to those of FIG. 25 are indicated by the same references.

While the usual display mode is selected, a setting of "0" is given to a density factor "df" set in a multiplier 80 of each color-balance alteration circuit ($142_1$, $142_2$, $142_3$), and thus the digital image-pixel signal ($R_{ij}$, $G_{ij}$, $B_{ij}$) passes through each color-balance alteration circuit ($142_1$, $142_2$, $142_3$) as it stands. Thus, as already stated above, during the selection of the usual display mode, the endoscope image is reproduced on the TV monitor 14 with the given proper color balance.

While the CRA display mode is selected, a setting of a suitable value, for example, "20", is given to the density factor "df" in the multiplier 80 of each color-balance alteration circuit ($142_1$, $142_2$, $142_3$). Thus, only when a value of the central digital image-pixel signal ($R_{ij}$, $G_{ij}$, $B_{ij}$) is lower than an average of values of the eight surrounding circumferential image-pixel-signals, is a digital signal (df*$\Delta R_{ij}$, df*$\Delta G_{ij}$, df*$\Delta B_{ij}$) output as a minus signal from the multiplier 80 to an AND-logic circuit 128 in each color-balance alteration circuit ($142_1$, $142_2$, $142_3$).

As is apparent from FIGS. 30 and 31, when the value of the red digital image-pixel signal ($R_{ij}$) is more than the values of the green and blue digital image-pixel signals ($G_{ij}$ and $B_{ij}$), i.e. when the value of the red digital image-pixel signal ($R_{ij}$) is maximum, the low-level signal (i.e., "0") is input from the first NOT-gate $140_1$ of the comparator circuit 133 to the AND-logic circuit 128, and thus the digital signal (df*$\Delta R_{ij}$) is output as a zero signal from the AND-logic circuit 128. In other words, the red digital image-pixel signal ($R_{ij}$) passes through the first color-balance alteration circuit $142_1$ as it stands, without being subjected to any color-balance alteration process by the first color-balance alteration circuit $142_1$.

On the other hand, when the value of the red digital image-pixel signal ($R_{ij}$) is maximum, the second NOT-gate $140_2$ outputs the high-level signal (i.e., "1") to the AND-logic circuit 128 in the second color-balance alteration circuit $142_2$, and thus the digital signal (df*$\Delta G_{ij}$) is output from the AND-logic circuit 128 to an adder circuit 72, as it stands. In other words, the absolute value of the signal (df*$\Delta G_{ij}$) is subtracted from the value of the green image-pixel signal ($G_{ij}$) in the adder circuit 72 in the second color-balance alteration circuit $142_2$.

Similarly, when the value of the red digital image-pixel signal ($R_{ij}$) is maximum, the third NOT-gate $140_3$ outputs the high-level signal (i.e., "1") to the AND-logic circuit 128 in the third color-balance alteration circuit $142_3$, and thus the digital signal (df*$\Delta B_{ij}$) is output from the AND-logic circuit 128 to an adder circuit 72, as it stands. In other words, the absolute value of the signal (df*$\Delta B_{ij}$) is subtracted from the value of the blue image-pixel signal ($G_{ij}$) in the adder circuit 72.

The same is true for either the case where the value of the green digital image-pixel signal ($G_{ij}$) is maximum or the case where the value of the blue digital image-pixel signal ($B_{ij}$) is maximum.

Note, in each color-balance alteration circuit ($140_1$, $140_2$, $140_2$), the outputting of the digital signals (df*$\Delta R_{ij}$, df*$\Delta G_{ij}$, df*$\Delta B_{ij}$) from the multiplier 80 to the AND-logic circuit 128 is synchronized with the outputting of the high-level or low-level signal from the NOT-gate ($140_1$, $140_2$, $140_2$) to the AND-logic circuit 128, due to the existence of the delay circuit 134 in the comparator circuit 133. Namely, the time necessary to process the digital image-pixel signal ($R_{ij}$, $G_{ij}$, $B_{ij}$) in the difference-calculation circuit 60 of each color-balance alteration circuit ($142_1$, $142_1$, $142_1$) is longer than the time necessary to process the digital image-pixel signal ($R_{ij}$, $G_{ij}$, $B_{ij}$) in the comparators of the comparator circuit 133, and a delay time is set in the delay circuit 134, so that the outputting of the digital signals (df*$\Delta R_{ij}$, df*$\Delta G_{ij}$, df*$\Delta B_{ij}$) from the multiplier 80 to the AND-logic circuit 128 and the outputting of the high-level or low-level signal from the NOT-gate ($140_1$, $140_2$, $140_2$) to the AND-logic circuit 128 is synchronized with each other.

According to the seventh embodiment, when a set of red, green, and blue digital image-pixel signals ($R_{ij}$, $R_{ij}$, and $B_{ij}$) derives from a fine recess area X on a mucous membrane surface featuring a reddish orange tone, as conceptually shown in FIG. 29, a value of the red signal ($R_{ij}$) is unchanged, but the values of the green and blue signals ($G_{ij}$ and $B_{ij}$) is reduced in proportion to an absolute value of a digital signal (df*$\Delta G_{ij}$, df*$\Delta B_{ij}$). Thus, the fine recess area X is reproduced on the TV monitor 14 with a lower brightness than a circumferential area surrounding the fine recess area X, whereby it is possible to clearly observe and examine the subtle unevenness of the mucous membrane surface. In this case, although veins, having a bluish tone, are in the vicinity of the fine recess area, it is possible to easily discriminate the existence of the veins, because the values of the blue signals ($B_{ij}$), derived from the veins, are not reduced, as is apparent form the foregoing.

Note, in the seventh embodiment, it is possible to perform the change in the density factor "df" of the multiplier 80 by executing a display-mode-selection-monitoring routine similar to that of FIG. 21.

Eighth Embodiment

Figure 32:
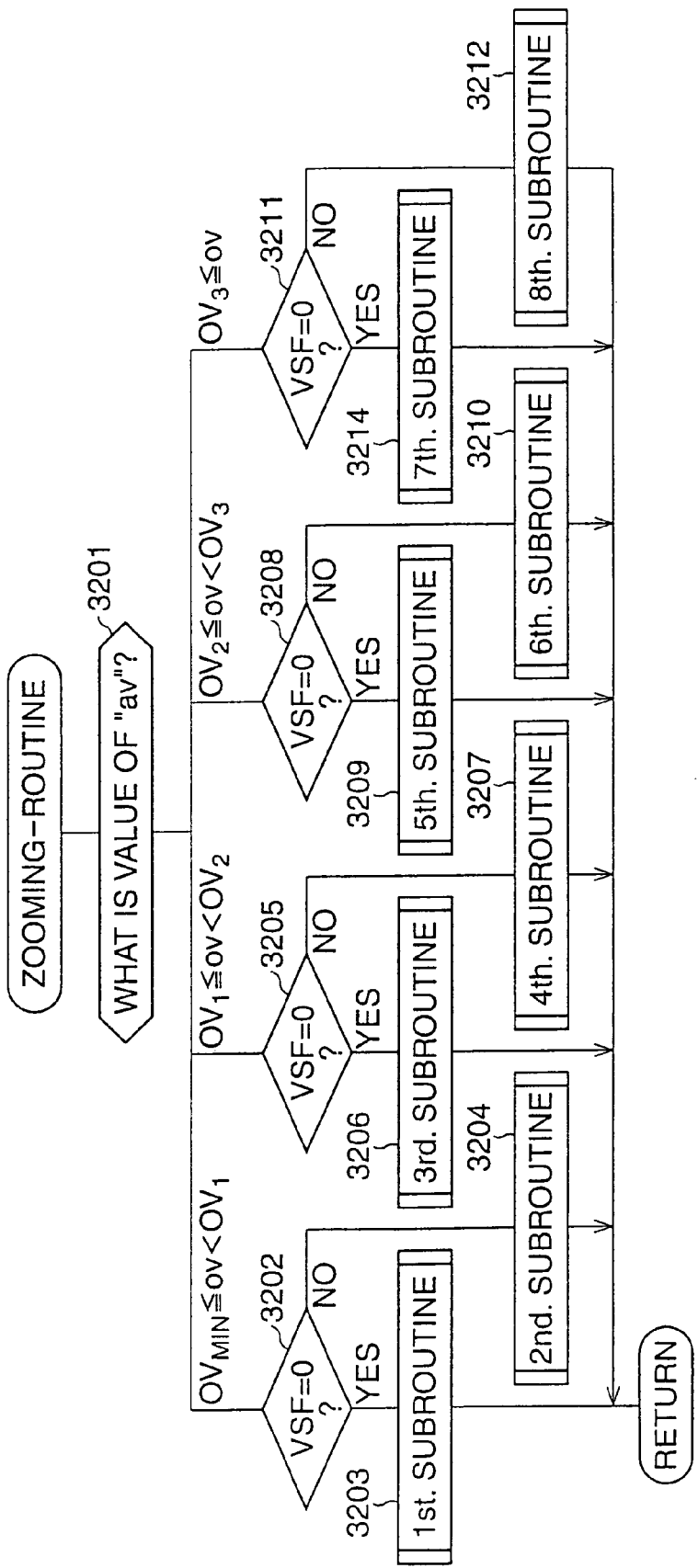
FIG. 32 is a schematic block diagram of an eighth embodiment of an electronic endoscope system according to the present invention.

Referring to FIG. 32, An eighth embodiment of an electronic endoscope system according to the present invention is shown as a block diagram. In this drawing, the features similar to those of FIG. 29 are indicated by the same references.

In the eight embodiment, the on-chip color filter method is used to reproduce an endoscope image as a full color image on a TV monitor 14, and a video scope 10 and an image-signal processing unit 12 are modified so as to conform to the on-chip color filter method.

In the eighth embodiment, similar to the second embodiment (FIG. 8) and the fourth embodiment (FIG. 17), a CCD image sensor 18 has a complementary color filter (not shown) provided on a light-receiving surface thereof. Also, a light source device, provided in the image-signal processing unit 12, is formed by a white light lamp 24, a diaphragm 26, and a condenser lens 28. Namely, the rotary color-filter 30 is eliminated from the light source device. Thus, white light is irradiated as an illuminating-light from a distal end face of an optical light guide 22. An illuminated object is focussed as an optical endoscope image on the light-receiving surface of the CCD image sensor 18 through the complementary color filter by an objective lens system 20, and the focussed endoscope image is converted into a frame of analog color image-pixel signals due to the existence of the complementary color filter.

In the eighth embodiment, the frame of analog color image-pixel signals, successively read from the CCD image sensor 18, is processed by a CCD process circuit 36, and each analog color image-pixel signal is converted into a digital color image-pixel signal by an analog-to-digital (A/D) converter 38. Then, the converted digital color image pixel signals are successively fed from the A/D converter 38 to an RGB-converting circuit 74, in which the digital color image-pixel signals are processed to thereby produce a red digital image-pixel signal, a green digital image-pixel signal, and a blue digital image-pixel signal, and the red, green, and blue digital image-pixel signals are temporarily stored in a frame memory 40 having sufficient memory capacity for the storage of the three frames of digital image-pixel signals ($R_{ij}$, $G_{ij}$ and $B_{ij}$).

Similar to the seventh embodiment, the red, green, and blue digital image-pixel signals ($R_{ij}$, $G_{ij}$ and $B_{ij}$) are simultaneously read from the frame memory 40, and are then fed to a color-balance alteration processor 132, which is essentially identical to that of the seventh embodiment. Also, in the eighth embodiment, similar to the seventh embodiment, either a usual display mode or a color-balance alteration display mode is selected by manually operating a display-mode selection switch 54 on a front panel 52.

Accordingly, while the usual display mode is selected, the red, green, and blue digital image-pixel signals ($R_{ij}$, $G_{ij}$ and $B_{ij}$) pass through the color-balance alteration processor 132 as they stand, and thus an endoscope image, sensed by the CCD image sensor 18, is reproduced as a full color motion picture on the TV monitor 14 with a given proper color balance in substantially the same manner as in the seventh embodiment. On the other hand, while the color-balance alteration display mode is selected, the endoscope image to be reproduced on a TV monitor 14 is subjected to a color-balance alteration process by the color-balance alteration processor 132 in substantially the same manner as in the seventh embodiment.

Finally, it will be understood by those skilled in the art that the foregoing descriptions are of preferred embodiments of the systems, and that various changes and modifications may be made to the present invention without departing from the spirit and scope thereof.

The present disclosure relates to subject matters contained in Japanese Patent Applications No. 2001-193134 (filed on Jun. 26, 2001), No. 2001-198584 (filed on Jun. 29, 2001), No. 2001-198274 (filed on Jun. 29, 2001), No. 2001-333880 (filed on Oct. 31, 2001),which are expressly incorporated herein, by reference, in their entirety.

The invention claimed is:

1. An electronic endoscope system including a video scope having a solid-state image sensor that successively produces a frame of color image-pixel signals composed of two frames of first-type-single-color image-pixel signals and second-type-single-color image-pixel signals, said electronic endoscope system comprising:
    a calculation system that calculates a first difference value between a first value of a central first-type-single-color image-pixel signal for a central first-type-single-color image-pixel and a first average of values of circumferential first-type-single-color image-pixel signals for pixels surrounding said central first-type-single-color image-pixel, and a second difference value between a second value of a corresponding central second-type-single-color image-pixel signal for a central second-type-single-color image-pixel and a second average of values of circumferential second-type-single-color image-pixel signals for pixels surrounding said central second-type-single-color image-pixel; and
    a color-balance alteration system that alters said first value when it is smaller than said first average of values, and that alters said second value when it is smaller than said second average of values, such that one of said first and second values is increased in proportion to an absolute value of a corresponding one of said first and second difference values, and such that the remaining one of said first and second values is decreased in proportion to an absolute value of the remaining corresponding one of said first and second difference values.

2. An electronic endoscope system as set forth in claim 1, further comprising:
    a first video signal production system that produces a first type of video signal based on the frame of color image-pixel signals;
    a second video signal production system that produces a second type of video signal based on the frame of color image-pixel signals processed by said color-balance alteration system; and
    a monitor system configured to selectively display a first image and a second image based on said first and second types of video signals, respectively.

3. An electronic endoscope system as set forth in claim 2, further comprising:
    a display-mode selection system that selects either a first display mode or a second display mode; and
    a display control system that displays said first image on said monitor system based on said first type of video signal when the first display mode is selected by said display-mode selection system, and that displays said second image on said monitor system based on said second type of video signal when the second display mode is selected by said display-mode selection system.

4. An electronic endoscope system as set forth in claim 3, further comprising:
a disablement system that disables said color-balance alteration system when the first display mode is selected by said display-mode selection system; and
an enablement system that enables said color-balance alteration system when the second display mode is selected by said display-mode selection system.

5. An electronic endoscope system including a video scope having a solid-state image sensor that successively produces a frame of color image-pixel signals composed of three frames of first-type-single-color image-pixel signals, second-type-single-color image-pixel signals, and third-type-single-color image-pixel signals, said electronic endoscope system comprising:
a calculation system that calculates a first difference value between a first value of a central first-type-single-color image-pixel signal for a central first-type-single-color image-pixel and a first average of values of circumferential first-type-single-color image-pixel signals for pixels surrounding said central first-type-single-color image-pixel, a second difference value between a second value of a corresponding central second-type-single-color image-pixel signal for a central second-type-signal-color image-pixel and a second average of values of circumferential second-type-single-color image-pixel signals for pixels surrounding said central second-type-single-color image-pixel, and a third difference value between a third value of a corresponding central third-type-single-color image-pixel signal for a central third-type-signal-color image-pixel and a third average of values of circumferential third-type-single-color image-pixel signals for pixels surrounding said central third-type-single-color image-pixel; and
a color-balance alteration system that alters said first value when it is smaller than said first average of values, that alters said second value when it is smaller than said second average of values, and that alters said third value when it is smaller than said third average of values, such that two of said first, second, and third values are respectively increased in proportion to absolute values of corresponding ones of said first, second, and third difference values, and such that the remaining one of said first, second, and third values is decreased in proportion to absolute values of the remaining corresponding one of said first, second, and third difference values.

6. An electronic endoscope system as set forth in claim 5, further comprising:
a first video signal production system that produces a first type of video signal based on the frame of color image-pixel signals;
a second video signal production system that produces a second type of video signal based on the frame of color image-pixel signals processed by said color-balance alteration system; and
a monitor system configured to selectively display a first image and a second image based on said first and second types of video signals, respectively.

7. An electronic endoscope system as set forth in claim 6, further comprising:
a display-mode selection system that selects either a first display mode or a second display mode; and
a display control system that displays said first image on said monitor system based on said first type of video signal when the first display mode is selected by said display-mode selection system, and that displays said second image on said monitor system based on said second type of video signal when the second display mode is selected by said display-mode selection system.

8. An electronic endoscope system as set forth in claim 7, further comprising:
a disablement system that disables said color-balance alteration system when the first display mode is selected by said display-mode selection system; and
an enablement system that enables said color-balance alteration system when the second display mode is selected by said display-mode selection system.

9. An electronic endoscope system comprising: a video scope having a solid-state image sensor that successively produces a first type frame of color image-pixel signals;
an image-signal processing unit including a first video signal production system that produces a first type of video signal based on the first type frame of color image-pixel signals;
a first monitor system that displays a first image based on said first type of video signal;
a color-balance alteration process unit including a color image-pixel-signal production system that successively produces a second type frame of color image-pixel signals based on said first type of video signal, a calculation system that calculates a difference value between a value of a central color image-pixel signal for a central color image-pixel, included in said second type frame, and an average of values of circumferential color image pixel signals for pixels surrounding said central color image-pixel, a color-balance alteration system that alters the value of said central color image-pixel signal in accordance with the difference value calculated by said calculation system, whereby said second type of color image-pixel signals is subjected to a color-balance alteration process by said color-balance alteration system, and a second video signal production system that produces a second type of video signal based on the second type frame of color image-pixel signals subjected to said color-balance alteration process; and
a second monitor system that displays a second image based on said second type of video signals,
wherein said color-balance alteration process unit further includes a third video signal production system that produces a third type of video signal based on the second type frame of color image-pixel signals not subjected to said color-balance alteration process, and said second monitor system is configured to selectively display a third image based on said third type of video signals.

10. An electronic endoscope system as set forth in claim 9, wherein said color-balance alteration unit further includes a display-mode selection system that selects either a first display mode or a second display mode; and
a display control system that displays said second image on said second monitor system based on said second type of video signal when the first display mode is selected by said display-mode selection system, and that displays said third image on said second monitor system based on said third type of video signal when the second display mode is selected by said display-mode selection system.

11. An electronic endoscope system as set forth in claim 10, wherein said color-balance alteration unit further includes a disablement system that disables said color-balance alteration system when the first display mode is selected by said display-mode selection system; and
an enablement system that enables said color-balance alteration system when the second display mode is selected by said display-mode selection system.

12. An electronic endoscope system comprising:
a video scone having a solid-state image sensor that successively produces a first type frame of color image-pixel signals;
an image-signal processing unit including a first video signal production system that produces a first type of video signal based on the first type frame of color image-pixel signals;
a first monitor system that displays a first image based on said first type of video signal;
a color-balance alteration process unit including a color image-pixel-signal production system that successively produces a second type frame of color image-pixel signals based on said first type of video signal, a calculation system that calculates a difference value between a value of a central color image-pixel signal for a central color image-pixel, included in said second type frame, and an average of values of circumferential color image-pixel signals for pixels surrounding said central color image-pixel, a color-balance alteration system that alters the value of said central color image-pixel signal in accordance with the difference value calculated by said calculation system, whereby said second type of color image-pixel signals is subjected to a color-balance alteration process by said color-balance alteration system, and a second video signal production system that produces a second type of video signal based on the second type frame of color image-pixel signals subjected to said color-balance alteration process; and
a second monitor system that displays a second image based on said second type of video signals,
wherein said color-balance alteration unit further includes a clock-pulse generator that produces a series of clock pulses, the successive production of said second type frame of color image-pixel signals by said color image-pixel-signal production system, the calculation of said difference value by said calculation system, and the alteration of said central color image-pixel signal by said color-balance alteration system being performed based on said clock pulses, and a clock-pulse-frequency change system that changes a frequency of said clock pulses in accordance with a variation in a spatial frequency of said first image.

13. An electronic endoscope system comprising:
a video scope having a solid-state image sensor that successively produces a first type frame of color image-pixel signals;
an image-signal processing unit including a first video signal production system that produces a first type of video signal based on the first type frame of color image-pixel signals;
a first monitor system that displays a first image based on said first type of video signal;
a color-balance alteration process unit including a color image-pixel-signal production system that successively produces a second type frame of color image-pixel signals based on said first type of video signal, a calculation system that calculates a difference value between a value of a central color image-pixel signal for a central color image-pixel, included in said second type frame, and an average of values of circumferential color image-pixel signals for pixels surrounding said central color image-pixel, a color-balance alteration system that alters the value of said central color image-pixel signal in accordance with the difference value calculated by said calculation system, whereby said second type of color image-pixel signals is subjected to a color-balance alteration process by said color-balance alteration system, and a second video signal production system that produces a second type of video signal based on the second type frame of color image-pixel signals subjected to said color-balance alteration process; and
a second monitor system that displays a second image based on said second type of video signals,
wherein said color-balance alteration unit further includes a restriction system that restricts an area, to be subjected to said color-balance alteration process, on a display area of said second monitor system, such that character information, displayed on the display area of said second monitor system, is prevented from being subjected to said color-balance alteration process.

14. An electronic endoscope system as set forth in claim 13, wherein said color-balance alteration unit further includes a restriction-area change system that changes the area restricted by said restriction system.

15. An electronic endoscope system including a video scope having a solid-state image sensor that successively produces a frame of color image-pixel signals composed of two frames of first-type-single-color image-pixel signals and second-type-single-color image-pixel signals, said electronic endoscope system comprising:
a calculation system that calculates a difference value between a first value of a central first-type-single-color image-pixel signal for a central first-type-single-color image-pixel and an average of values of circumferential first-type-single-color image-pixel signals for pixels surrounding said central first-type-single-color image-pixel, and a difference value between a value of a corresponding central second-type-single-color image-pixel signal for a central second-type-single-color image-pixel and an average of values of circumferential second-type-single-color image-pixel signals for pixels surrounding said central second-type-single-color image-pixel;
a comparison system that compares the value of said central first-type-single-color image-pixel signal and the value of said central second-type-single-color image-pixel signal with each other, to thereby determine which values value is smaller; and
a color-balance alteration system that decreases only a smaller one of said two values in proportion to an absolute value of the corresponding difference value when the smaller one of said two values is smaller than the corresponding average of values.

16. An electronic endoscope system as set forth in claim 15, further comprising:
a first video signal production system that produces a first type of video signal based on the frame of color image-pixel signals;
a second video signal production system that produces a second type of video signal based on the frame of color image-pixel signals processed by said color-balance alteration system; and
a monitor system configured to selectively display a first image and a second image based on said first and second types of video signals, respectively.

17. An electronic endoscope system as set forth in claim 16, further comprising:
- a display-mode selection system that selects either a first display mode or a second display mode; and
- a display control system that displays said first image on said monitor system based on said first type of video signal when the first display mode is selected by said display-mode selection system, and that displays said second image on said monitor system based on said second type of video signal when the second display mode is selected by said display-mode selection system.

18. An electronic endoscope system as set forth in claim 17, further comprising:
- a disablement system that disables said color-balance alteration system when the first display mode is selected by said display-mode selection system; and
- an enablement system that enables said color-balance alteration system when the second display mode is selected by said display-mode selection system.

19. An electronic endoscope system including a video scope having a solid-state image sensor that successively produces a frame of color image-pixel signals composed of three frames of first-type-single-color image-pixel signals, second-type-single-color image-pixel signals and third-type-single-color image-pixel signals, the electronic endoscope system comprising:
- a calculation system that calculates a difference value between a first value of a central first-type-single-color image-pixel signal for a central first-type-single-color image-pixel and an average of values of circumferential first-type-single-color image-pixel signals for pixels surrounding said central first-type-single-color image-pixel, that calculates a difference value between a value of a corresponding central second-type-single-color image-pixel signal for a central second-type-single-color image-pixel and an average of values of circumferential second-type-single-color image-pixel signals for pixels surrounding said central second-type-single-color image-pixel, and that calculates a difference value between a value of a corresponding central third type-single-color image-pixel signal for a central third-type-single-color image-pixel and an average of values of circumferential third-type-single-color image-pixel signals for pixels surrounding said central third-type-single-color image-pixel;
- a comparison system that compares the value of said central first-type-single-color image-pixel signal, that compares the value of said central second-type-single-color image-pixel signals, and that compares the value of said central third-type-single-color image-pixel signals with each other, to thereby determine a maximum one of said three values; and
- a color-balance alteration system that decreases the respective two values, except for the maximum value, in proportion to absolute values of the corresponding difference values when each of said two values is smaller than the corresponding average of values.

20. An electronic endoscope system as set forth in claim 19 further comprising:
- a first video signal production system that produces a first type of video signal based on the frame of color image-pixel signals;
- a second video signal production system that produces a second type of video signal based on the frame of color image-pixel signals processed by said color-balance alteration system; and
- a monitor system configured to selectively display a first image and a second image based on said first and second types of video signals, respectively.

21. An electronic endoscope system as set forth in claim 20, further comprising:
- a display-mode selection system that selects either a first display mode or a second display mode; and
- a display control system that displays said first image on said monitor system based on said first type of video signal when the first display mode is selected by said display-mode selection system, and that displays said second image on said monitor system based on said second type of video signal when the second display mode is selected by said display-mode selection system.

22. An electronic endoscope system as set forth in claim 21, further comprising:
- a disablement system that disables said color-balance alteration system when the first display mode is selected by said display-mode selection system; and
- an enablement system that enables said color-balance alteration system when the
- second display mode is selected by said display-mode selection system.

* * * * *